US007690173B2

(12) United States Patent
Luciano, Jr. et al.

(10) Patent No.: US 7,690,173 B2
(45) Date of Patent: Apr. 6, 2010

(54) MULTIPLE PRESCRIPTION PRODUCTION FACILITY

(75) Inventors: Robert A. Luciano, Jr., Reno, NV (US);
Lawrence Luciano, Sommerville, NJ (US)

(73) Assignee: Edge Medical, Inc., Reno, NV (US)

( * ) Notice: Subject to any disclaimer, the term of this patent is extended or adjusted under 35 U.S.C. 154(b) by 65 days.

(21) Appl. No.: 11/796,123

(22) Filed: Apr. 25, 2007

(65) Prior Publication Data

US 2007/0270998 A1    Nov. 22, 2007

Related U.S. Application Data

(63) Continuation-in-part of application No. 11/241,783, filed on Sep. 30, 2005.

(60) Provisional application No. 60/795,370, filed on Apr. 26, 2006, provisional application No. 60/795,446, filed on Apr. 26, 2006, provisional application No. 60/795,413, filed on Apr. 26, 2006.

(51) Int. Cl.
| | |
|---|---|
| *B65B 57/00* | (2006.01) |
| *B65B 59/00* | (2006.01) |
| *B65B 7/28* | (2006.01) |
| *B65B 5/10* | (2006.01) |

(52) U.S. Cl. ............... 53/396; 53/411; 53/420; 53/471; 53/474; 700/216; 700/219; 700/244

(58) Field of Classification Search ............ 53/396, 53/411, 420, 445, 443, 471, 485, 474; 700/216, 700/219, 244

See application file for complete search history.

(56) References Cited

U.S. PATENT DOCUMENTS 3,780,856 A * 12/1973 Braverman ............... 53/471

(Continued)

FOREIGN PATENT DOCUMENTS

WO    WO 2004/082561 A1    9/2004

*Primary Examiner*—Stephen F Gerrity
(74) *Attorney, Agent, or Firm*—Kerr IP Group, LLC

(57) ABSTRACT

A production facility configured to fill a multiple prescription order having different medications is described. The production facility comprises a means for processing a multiple prescription order, a plurality of multiple prescription containers, a first labeling component, a first inspection module, a second labeling component and a second inspection module. The means for processing the multiple prescription order is associated with a particular patient, and the multiple prescription order comprises at least two different tablets that are consumed at prescribed intervals determined by a prescription. Each of the plurality of multiple prescription containers is associated with a prescribed time interval determined by the multiple prescription order, and each multiple prescription container is configured to receive the different medications. The first labeling component is configured to generate a detailed label that provides a plurality of medical information regarding the different tablets. The first inspection module is configured to inspect an open multiple prescription container having the different tablets. The second labeling component is configured to print a date and a time on a lidstock for the patient to consume the tablets, and the second labeling component is configured to fixedly couple the lidstock to each multiple prescription container thereby sealing the multiple prescription containers. The second inspection module is configured to inspect the sealed multiple prescription containers.

16 Claims, 40 Drawing Sheets

U.S. PATENT DOCUMENTS

| | | | |
|---|---|---|---|
| 4,535,890 A * | 8/1985 | Artusi ........................ 206/530 |
| 4,546,901 A | 10/1985 | Buttarazzi |
| 4,655,026 A * | 4/1987 | Wigoda ......................... 53/55 |
| 4,867,315 A * | 9/1989 | Baldwin ...................... 53/471 |
| 4,953,745 A | 9/1990 | Rowlett, Jr. |
| 6,115,996 A * | 9/2000 | Yuyama et al. ............... 53/411 |
| 6,308,494 B1 * | 10/2001 | Yuyama et al. ............ 53/131.3 |
| 6,324,253 B1 | 11/2001 | Yuyama et al. |
| 6,681,935 B1 * | 1/2004 | Lewis ........................ 206/534 |
| 6,735,497 B2 * | 5/2004 | Wallace et al. ............. 700/231 |
| 6,771,369 B2 * | 8/2004 | Rzasa et al. ................. 356/326 |
| 6,892,512 B2 | 5/2005 | Rice et al. |
| 7,010,899 B2 | 3/2006 | McErlean et al. |
| 7,028,723 B1 * | 4/2006 | Alouani et al. ................. 141/83 |
| 7,185,476 B1 * | 3/2007 | Siegel et al. ................... 53/443 |
| 2004/0069674 A1 * | 4/2004 | Siegel ........................ 206/538 |
| 2004/0162634 A1 * | 8/2004 | Rice et al. .................... 700/235 |
| 2004/0256277 A1 * | 12/2004 | Gedanke ..................... 206/538 |
| 2005/0061825 A1 | 3/2005 | Willoughby et al. |
| 2005/0171813 A1 * | 8/2005 | Jordan .......................... 705/2 |
| 2005/0209879 A1 | 9/2005 | Chalmers |
| 2005/0218152 A1 * | 10/2005 | Simon ........................ 221/203 |
| 2006/0122729 A1 * | 6/2006 | Murphy et al. .............. 700/222 |

* cited by examiner

*FIG. 4*

Form fields shown (labeled with reference numerals):
- 102 First Name
- 102 Last Name
- 104 Address
- 112 Height
- 114 Weight
- 116 Sex
- 110 DOB
- 106 Telephone
- 120 Medical Conditions
- 108 E-mail
- 122 Doctor Information
- 124 Drug Allergies
- 126 Current Medications
- 128 ○ Single Package
- 130 ○ Multi-Script Package
- Type of Package: ○ Sleeved  ○ Circular  ○ Grid  ○ Plastic Bag
- Size: ○ Travel  ○ Notebook  ○ Companion
- 132 / 134 / 136 / 138 / 140
- Child Resistant: ○ Yes  ○ No
- 142 Requested Medications (Prescription Required and Must be Scanned or Faxed)

| Product: | Dosage: | Quantity: | Type | Price |
|---|---|---|---|---|
| 1. |  |  | ○ Generic  ○ Name Brand |  |
| 2. |  |  | ○ Generic  ○ Name Brand |  |
| 3. |  |  | ○ Generic  ○ Name Brand |  |

Recommended Time(s) for taking Product 1: ___
Recommended Time(s) for taking Product 2: ___
Recommended Time(s) for taking Product 3: ___

- 144 Sub-Total
- 146 Shipping
- 148 Order Total

150 Credit Card Information
- Name:
- Number:
- Type of Card:
- Expiration Date:

|  | — 162 |  |  |
|---|---|---|---|
|  | — 164 | — 160 | — 166 |

Thomas Goodall
1234 Tahoe Ct.
Reno, NV 89502
(775) 555-1212

GP: George Carver, MD
Spec: Jake Long, MD
Ins.: Hometown Health
No: POE 12357-111317

168 — Name: Zocor
Daily Dosage: 80 mg/day
Administer: 2X per day
one 40 mg. pill after breakfast,
one 40 mg. pill after dinner 170 — Description: Zocor is a cholesterol-lowering drug. In people with high cholesterol and heart disease, Zocor reduces the risk of heart attack, and stroke.
172 — Side effects may include abdominal pain, headache, constipation, diarrhea, gas, muscle weakness with rash, nausea, upper respiratory infection, upset stomach.
174 — Interaction(s): Many food and drug interactions including grapefruit juice. Consult Doctor and see detailed list or go to website to identify drug interactions.

Name: Norvasc
Daily Dosage: 5 mg/day
Administer: 2X per day
one 2.5 mg. pill after breakfast,
one 2.5 mg. pill after dinner

Description: Norvasc is a calcium channel blocker that controls high blood pressure (HBP). HBP reduction helps prevent strokes, heart attacks and kidney problems.
Side effects may include nausea, fatigue, weakness, stomach pain, drowsiness, muscle cramp, headache or flushing.
CONTACT YOUR DOCTOR IMMEDIATELY you experience swelling of your feet or legs; tender, bleeding, or swollen gums; worsening chest pain; yellowing of the eyes or skin; dark urine; a fast or irregular heartbeat; or difficulty breathing.

Name: Pravachol
Daily Dosage: 40 mg/day
Administer: 2X per day
one 20 mg. pill after breakfast,
one 20 mg. pill after dinner

Description: Pravachol is a cholesterol-lowering drug that improves chances of avoiding a heart attack by helping to reduce LDL cholesterol in the blood.
Side effects may include abdominal pain, chest pain, headache, constipation, diarrhea, gas, nausea, muscle aching, urinary problems, vomiting.
Drug Interaction: Many drug interactions. Consult Doctor and see detailed list or go to website to identify drug interactions.

Name: Plavix
Daily Dosage: 150 mg/day
Administer: 2X per day
one 75 mg. pill after breakfast,
one 75 mg. pill after dinner

Description: Plavix is an antiplatelet drug that prevents the clumping of platelets, which reduces the chances of blood clots that cause strokes and heart attacks.
Side effects may include rashes and/or itching, diarrhea, abdominal pain, indigestion, heartburn, constipation, bleeding in stomach, liver and bile disorders.
Drug Interaction: St. John's wort, aspirin. Consult Doctor and see detailed list or go to website to identify other drug interactions.

FIG. 5

MULTIPLE PRESCRIPTION PRODUCTION FACILITY

CROSS-REFERENCE TO RELATED APPLICATIONS

This application claims the benefit under 35 U.S.C. 119(e) of U.S. Provisional Application No. 60/795,370, filed Apr. 26, 2006, which is incorporated herein by reference in its entirety. This application claims the benefit under 35 U.S.C. 119(e) of U.S. Provisional Application No. 60/795,446, filed Apr. 26, 2006, which is incorporated herein by reference in its entirety. This application claims the benefit under 35 U.S.C. 119(e) of U.S. Provisional Application No. 60/795,413, filed Apr. 26, 2006, which is incorporated herein by reference in its entirety. This application is a continuation-in-part of patent application of patent application Ser. No. 11/241,783, filed Sep. 30, 2005, which is incorporated herein by reference in its entirety.

BACKGROUND

1. Field

The description relates to the field of tablet packaging and delivery systems. More particularly, the description relates to ordering and filling a prescription comprising a plurality of different medications.

2. Description of Related Art

One of the major problems in the taking of prescribed daily medications emanates from the fact that, in many instances the patient has to take more than one medication in the form of pills or tablets. A principal concern is determining whether all medications have been taken in compliance with the prescribed daily regimen. Many times this concern is compounded by the requirement that portions of the various medications must be taken at different times during the day.

The fear of taking improper dosages of prescribed medication can be particularly acute in the elderly, many of whom have some degree of mental dementia and can easily be confused as to whether they have taken all of their medications at the correct time. Some patients, with curtailed mental capabilities, have difficulty just in sorting out the medications preparatory to taking them, let alone taking the medication in a timely manner. Providing medications to disabled and/or incapacitated individuals can also be a problem for caregivers, particularly those in hospitals and assisted living facilities where one caregiver may oversee the medication of many patients.

Thus, there is a need for a positive delivery system and tablet package assembly for the delivery of multi-prescription dosages. A tablet packaging and delivery system that could decrease the possibility of human error and provide an easy to use set-up for the correct selection and delivery of multi-tablet/multi-time medications would be welcomed by the pharmaceutical and medical communities.

There is also a need for a tablet delivery system that provides evidence that the prescriptions were actually taken or administered as prescribed. Such a system would be an efficient way for any patient to take such multi-dosages but it would be especially beneficial for a patient of limited mental capacity as well as to caregivers in the hospital setting.

There is also a need for a tablet assembly and delivery system for vitamin supplements. Vitamin supplements are also often used in the same manner as many prescribed drug regiments with many of the same problems and inconveniences. Therefore a delivery system that addresses the needs of multi-prescription administration also contains many benefits for, and can be applied to, the vitamin and herbal supplement market.

One solution to the problem of taking multiple medications is to pre-package the multiple medications so that users can take the pre-packaged medications at a predetermined time. Generally, these methods of pre-packaging medications are targeted to patients that may lack maturity and/or mental capacity to take the correct medications at the correct time. For example, young children in a school or campground, and elderly individuals in elder care centers, or nursing homes are target groups for the pre-packaging of medications. Some of the pre-packaged medications are placed in a small plastic bag, which may be easily misplaced and is not child proof. Other pre-packaged medications are placed in sealed cups that are difficult to open and that can not be made child proof.

Additionally, the pre-packaging of multiple medications is also limited by distributing pre-packaged medications to a limited geographical location. For example, the pre-packaging of multiple medications is only provided in hospitals, medical institutions, campgrounds, or schools. Thus, the geographic limitation makes it difficult to effectively distribute the pre-packaged medications to a broad group of people over a broad geographic area.

Furthermore, pre-packaged multiple medications are difficult to order because the pre-packaging of multiple medications is a specialty service that has not been automated. The manual processing of prescription orders is expensive because the process lacks automation. Therefore, there is a need for an automated ordering system and process that is simple and cost effective for a patient or a pharmacist to use. An automated system and method for receiving orders would make it substantially easier to process a multiple prescription order, which would in turn make the process much more cost effective.

Further still, the current pre-packaging of multiple medications does not provide a simplified labeling technique that permits a caregiver to efficiently monitor the dispensing of different medications at pre-determined intervals. For example, the current techniques for dispensing medications do not provide summaries of the medications being taken by a patient. Additionally, although a pharmacist may provide information about drug interactions, there is no simple and clear record that describes drug interactions in a patient-friendly manner.

Further yet, there is a need for an efficient production facility that efficiently processes and inspects the pre-packaged multiple prescription containers. Automated processing and inspection techniques can dramatically improve efficiencies and minimize improper packaging or labeling. Thus, by automating the tablet processing and inspection process a more cost effective solution for the pre-packaging of multiple prescriptions can be obtained.

The following description provides a convenient and efficient way for patients, pharmacists, and physicians to order multi-drug prescriptions from a pharmaceutical dispensing system which produces multi-dose prescriptions. This description allows for prescriptions to be placed from a computer, telephone, facsimile, mail, or any combination thereof.

SUMMARY

A production facility configured to fill a multiple prescription order having different medications is described. The production facility comprises a means for processing a multiple prescription order, a plurality of multiple prescription containers, a first labeling component, a first inspection module, a second labeling component and a second inspection module. The means for processing the multiple prescription order is associated with a particular patient, and the multiple prescription order comprises at least two different tablets that are consumed at prescribed intervals determined by a prescription. The plurality of multiple prescription containers where each of the multiple prescription containers is associated with a prescribed time interval determined by the multiple prescription order and each multiple prescription container is configured to receive the different medications that are consumed at the prescribed time interval. The first labeling component is configured to generate a detailed label that provides a plurality of medical information regarding the different tablets. The first inspection module is configured to inspect an open multiple prescription container having the different tablets. The second labeling component is within the production facility and the second labeling component is configured to print a date and a time on a lidstock for the patient to consume the tablets, the second labeling component configured to fixedly couple the lidstock to each multiple prescription container thereby sealing the multiple prescription containers. The second inspection module configured to inspect the sealed multiple prescription containers.

A method for operating the production facility that is configured to fill the multiple prescription order having different medications is also described. The method comprises processing the multiple prescription order that is associated with a particular patient. The method then proceeds to retrieve the plurality of multiple prescription containers and fills each multiple prescription container with the different tablets. An inspection of each open multiple prescription container having the different tablets is performed. The lidstock is labeled with a date and a time for having the particular patient consume the different tablets. The open multiple prescription container with the lidstock are sealed, and the sealed multiple prescription container having the tablets are inspected. A detailed label that provides a plurality of medical information regarding the tablets for the patient is associated with the sealed multiple prescription containers.

DRAWINGS

The present invention will be more fully understood by reference to the following drawings which are for illustrative, not limiting, purposes.

FIG. 4 shows an illustrative graphical user interface (GUI) for receiving a prescription order.

FIG. 5 shows an illustrative detailed label that is generated at the production facility.

Figure 24A:
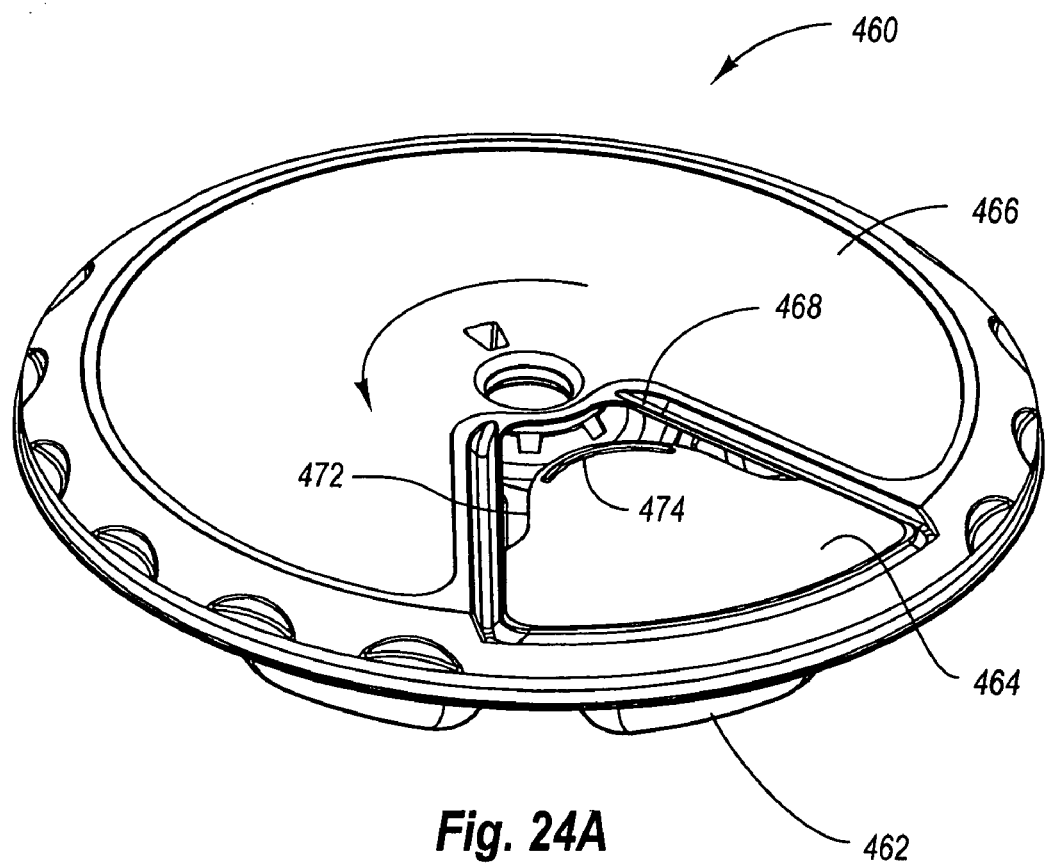
FIG. 24A is a perspective view of a third embodiment of a multiple prescription container assembly that is circular.
Figure 24B:
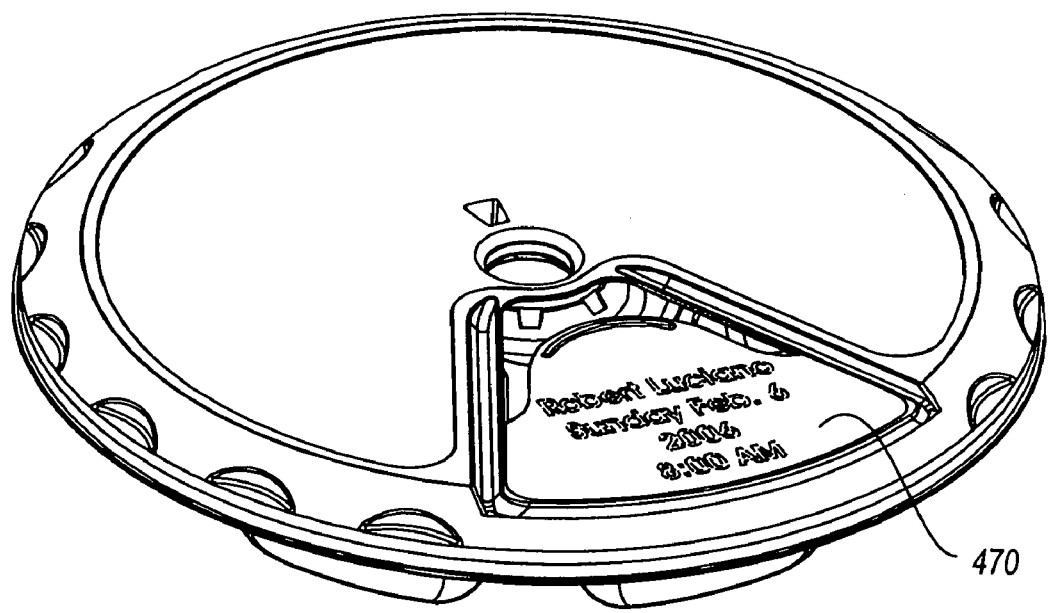
FIG. 24B shows the container of FIG. 24A with the having markings of printed information thereon.
Figure 25:
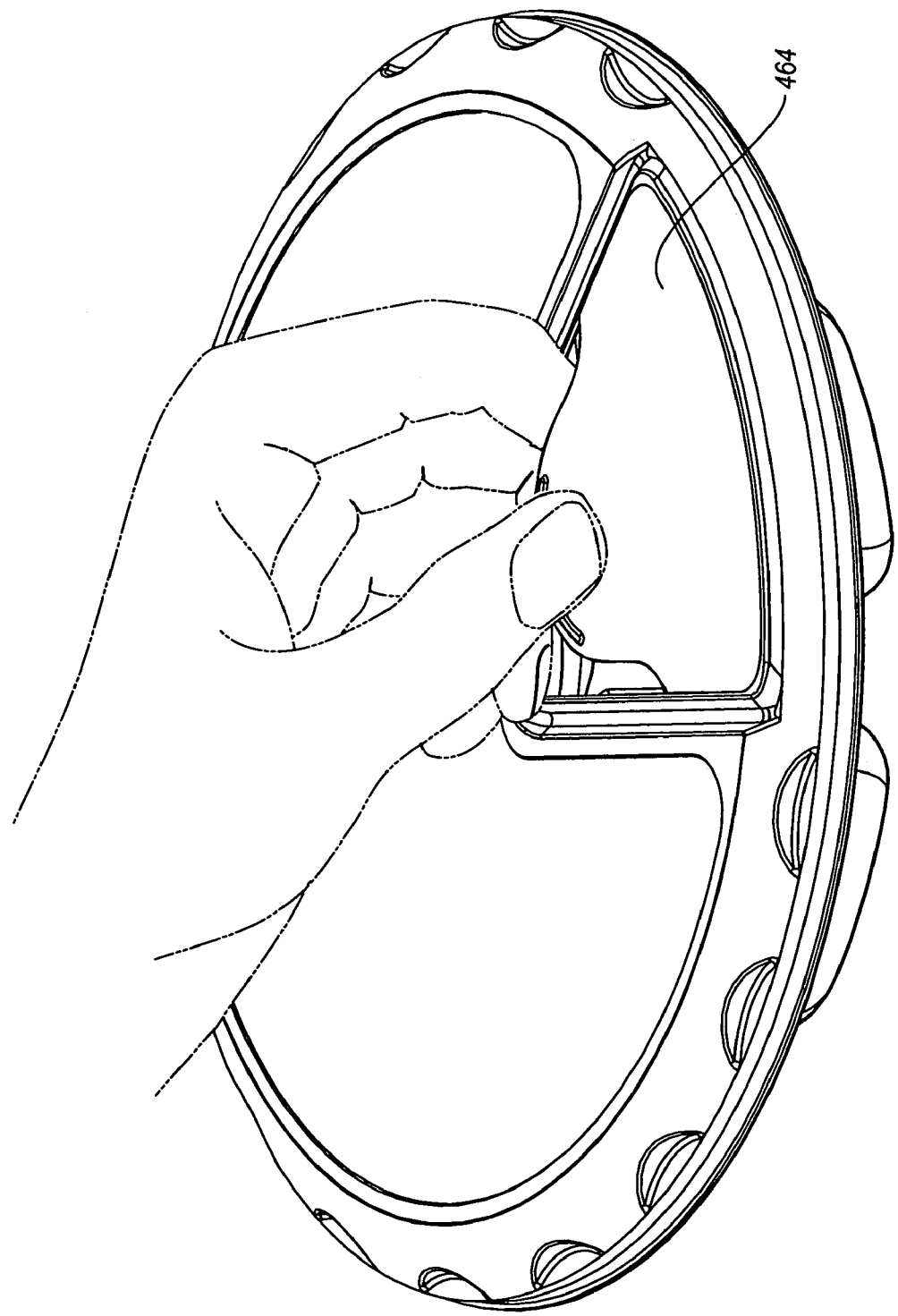

FIG. 25 provides a more detailed view of a patient or caregiver removing the lid from the circular multiple prescription container in FIGS. 24A and 24B.

Figure 26:
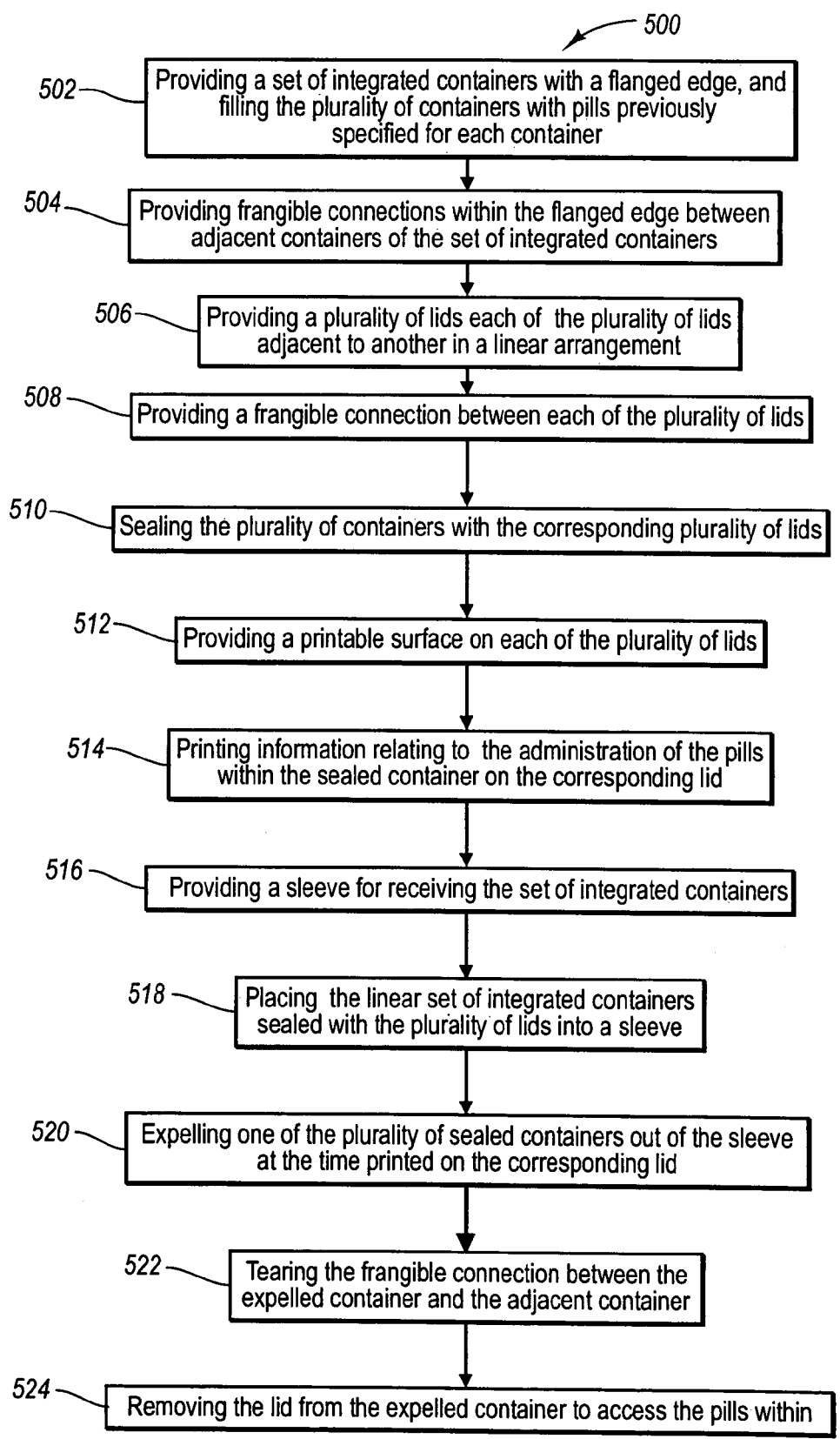

FIG. 26 is a flowchart showing a method for dispensing tablets which utilizes a secondary package or sleeve for housing the primary package or sealed multiple prescription container.

Figure 27:
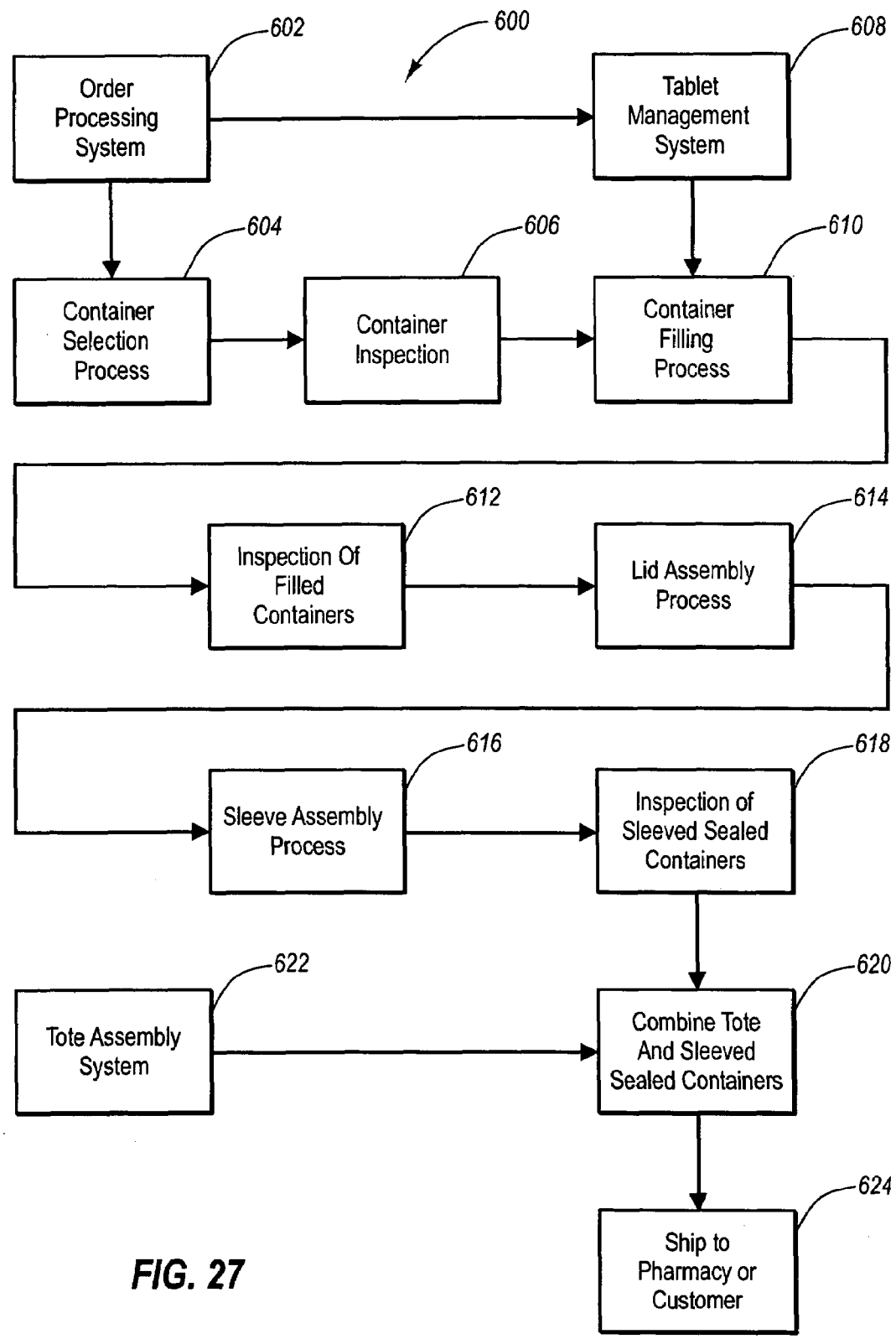

FIG. 27 is a flowchart showing the processes and systems used by a production facility to fill a prescription order.

Figure 28:
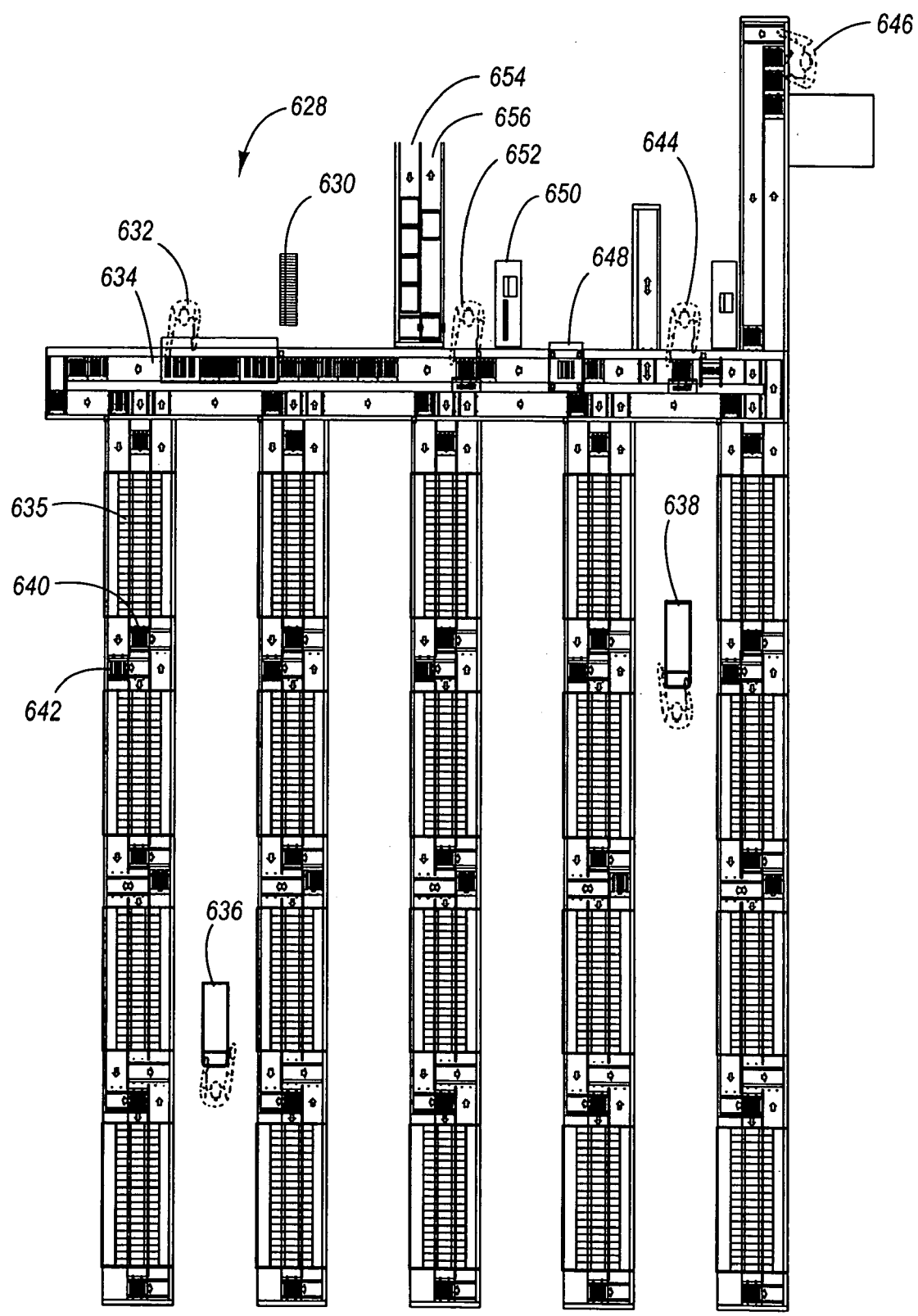

FIG. 28 is a top view of an illustrative manufacturing floor that fills the prescription order.

Figure 29:
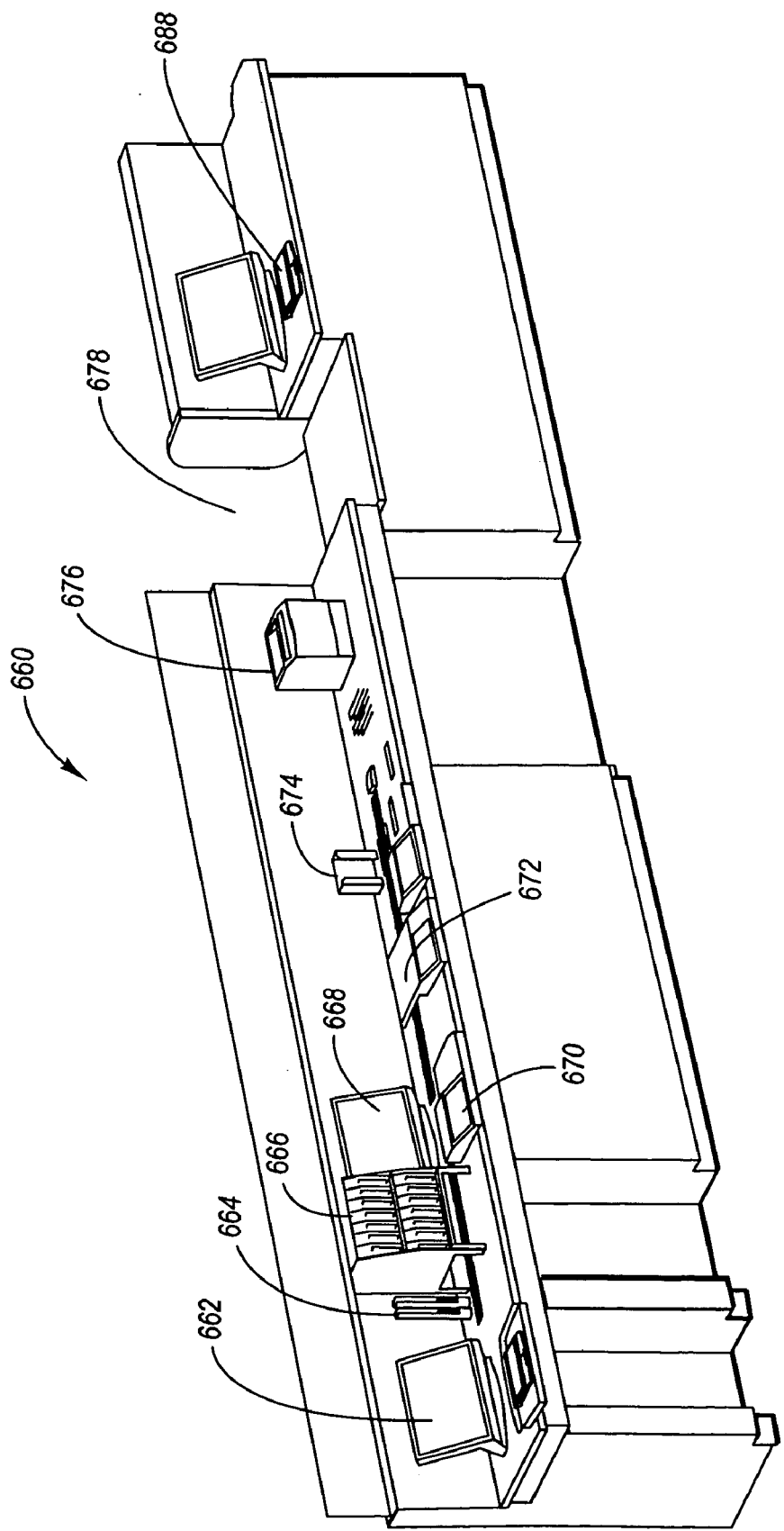

FIG. 29 is an isometric view of an illustrative tabletop system that can also fill the prescription order.

Figure 30:
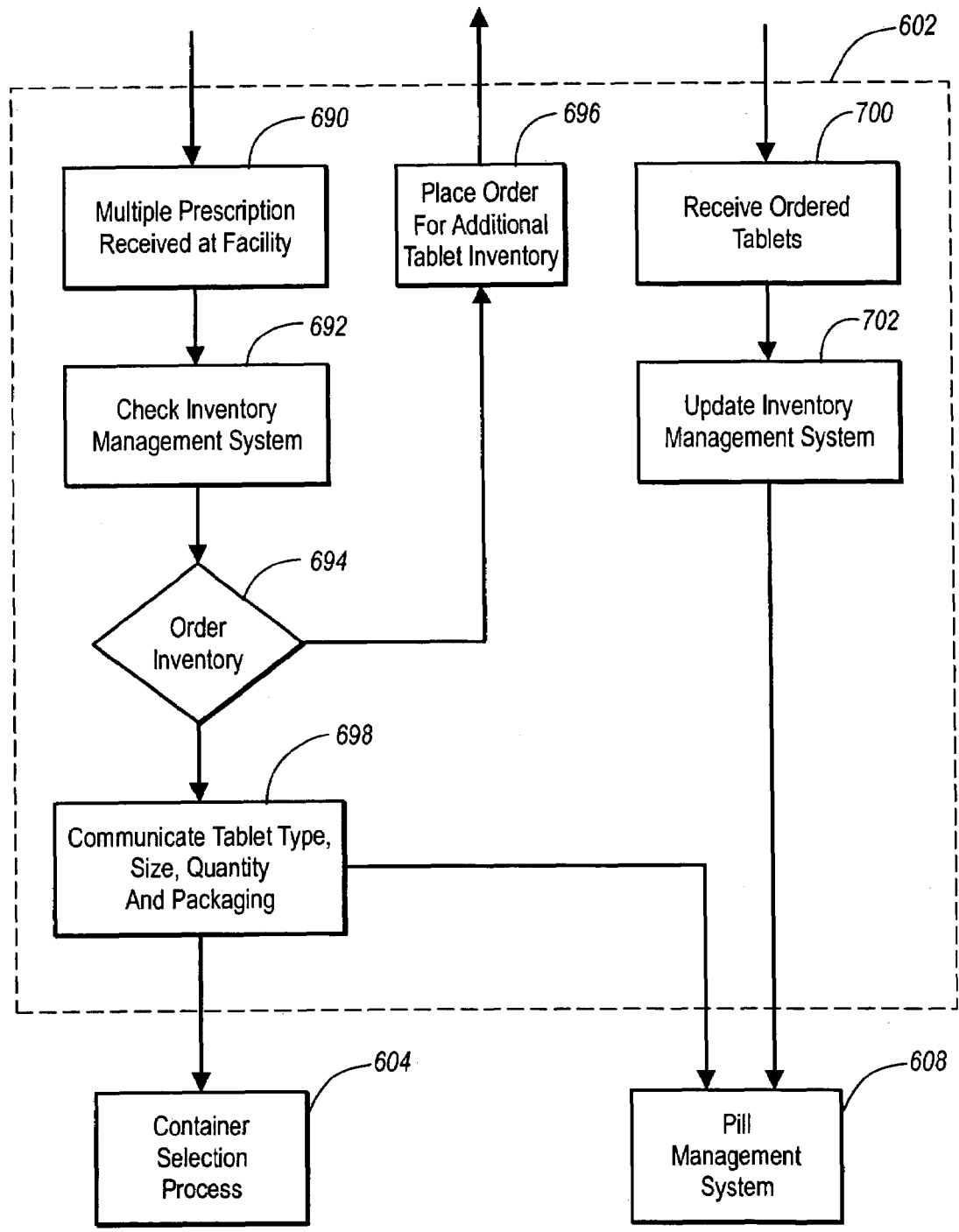

FIG. 30 is a block diagram of an illustrative order processing system.

Figure 31:
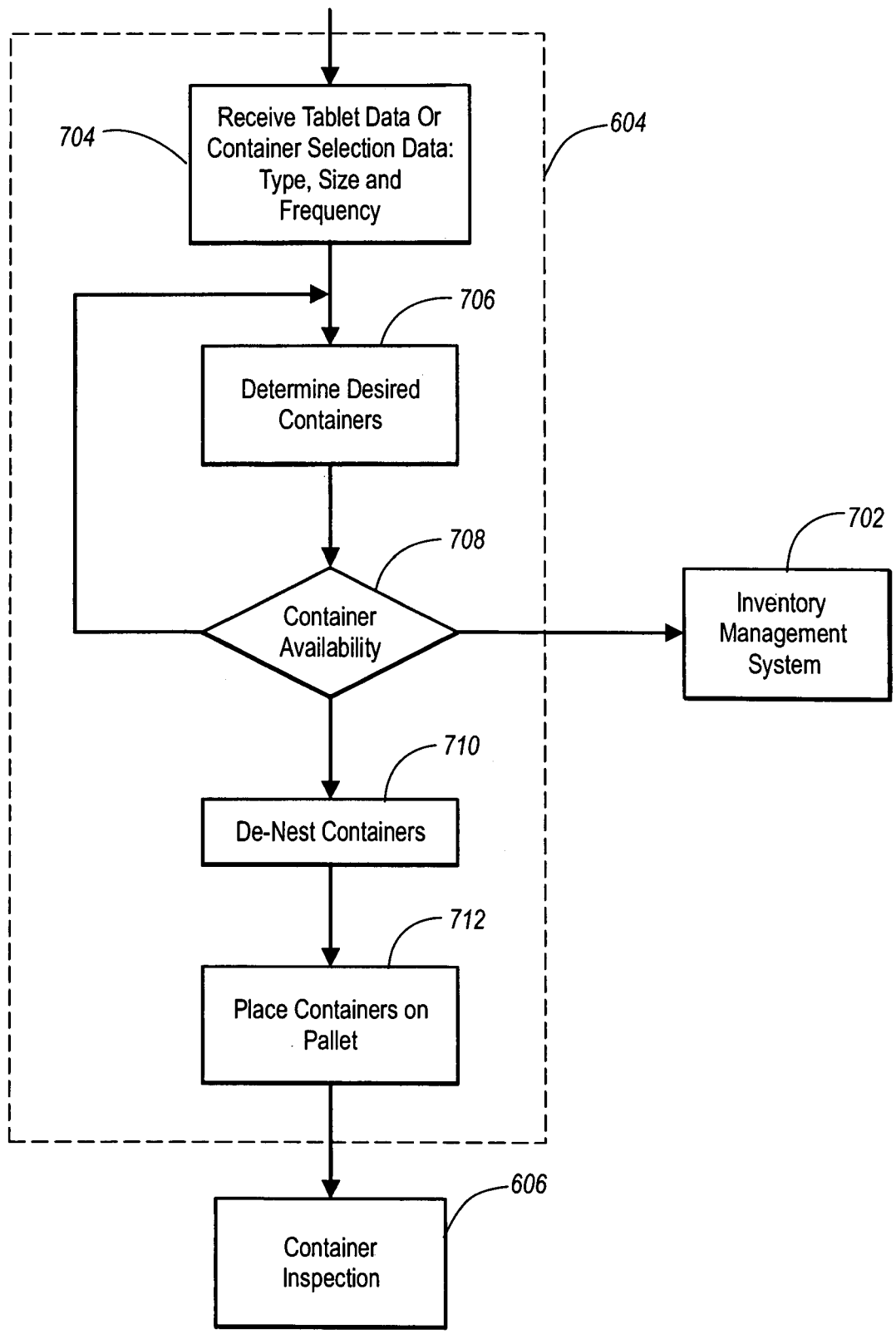

FIG. 31 is a flowchart of an illustrative container selection process.

Figure 32:
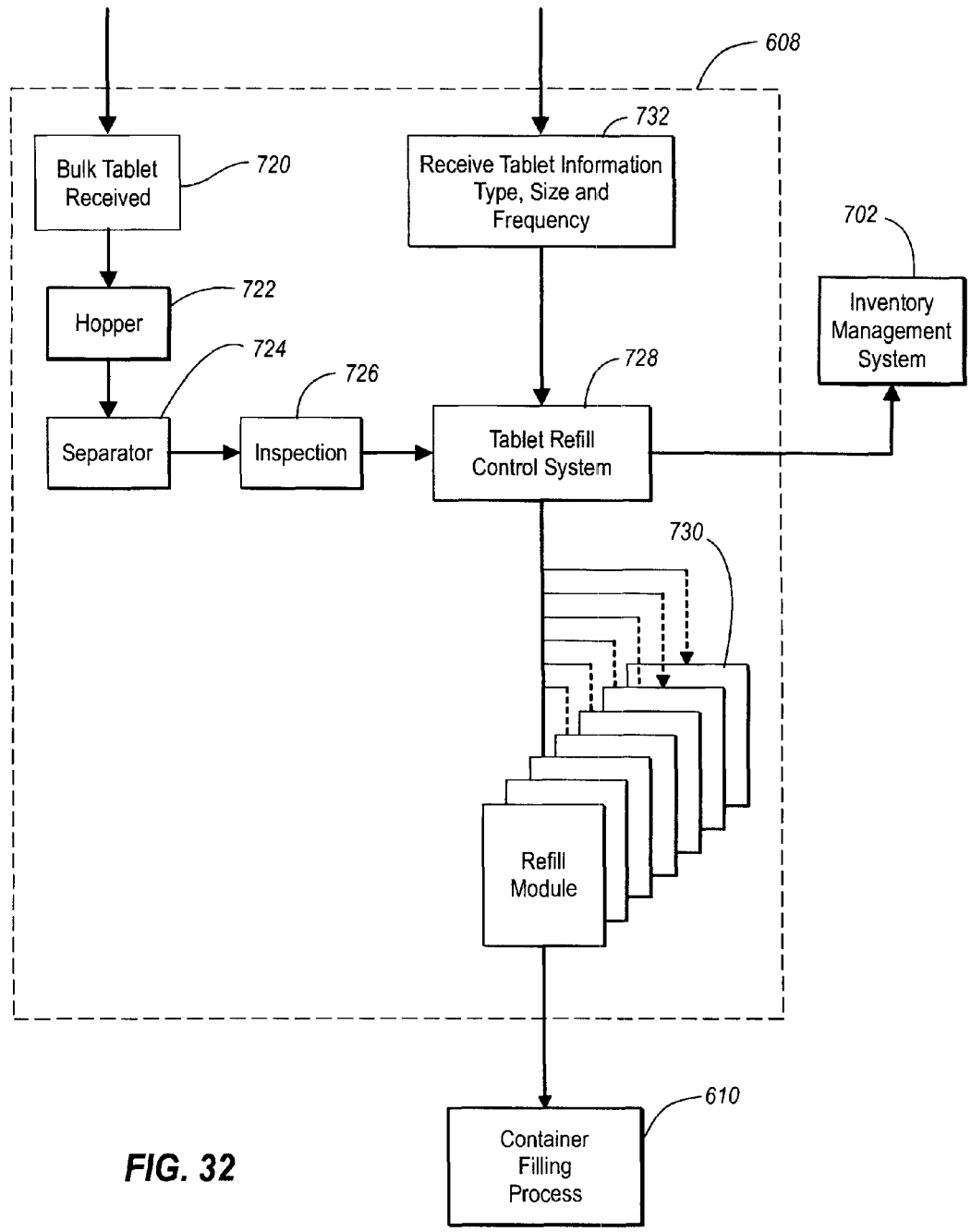

FIG. 32 is a block diagram of an illustrative pill management system.

Figure 33:
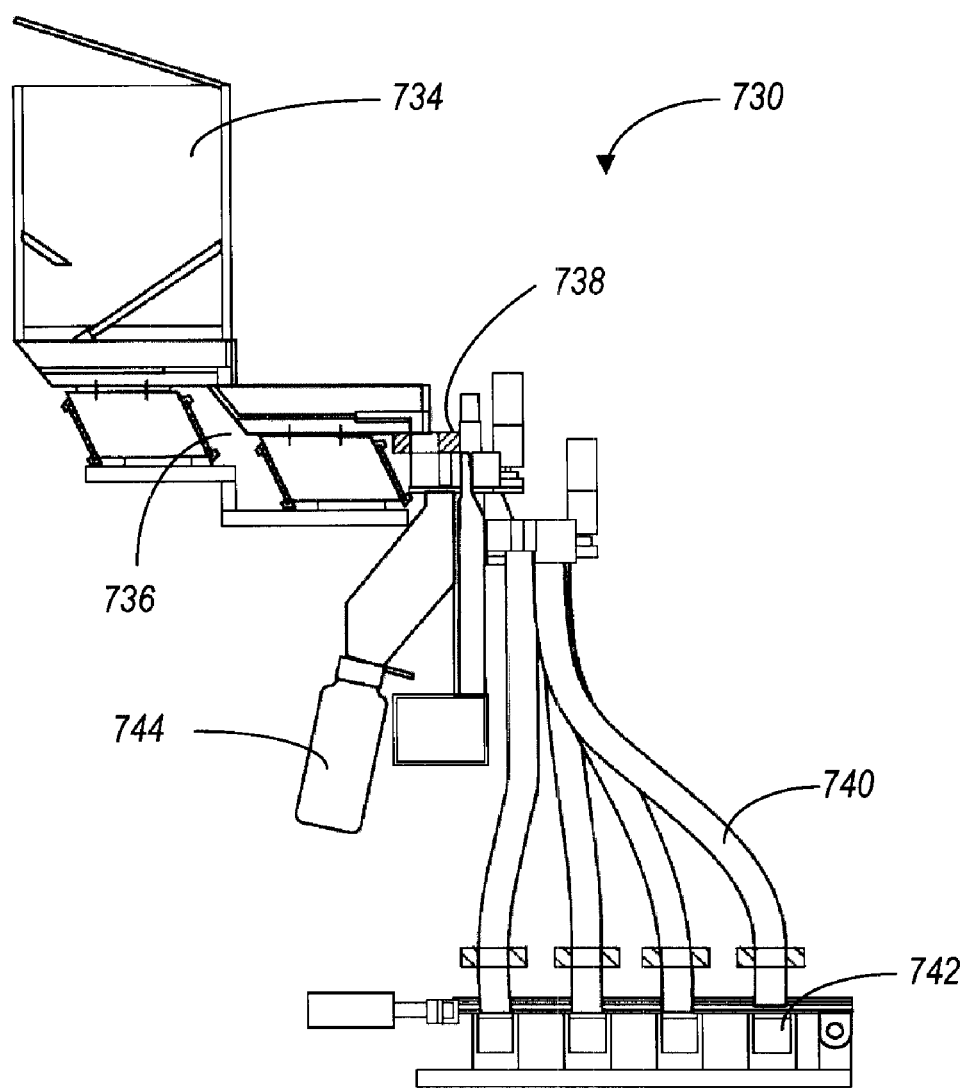

FIG. 33 is a side view of an illustrative refill module.

Figure 34:
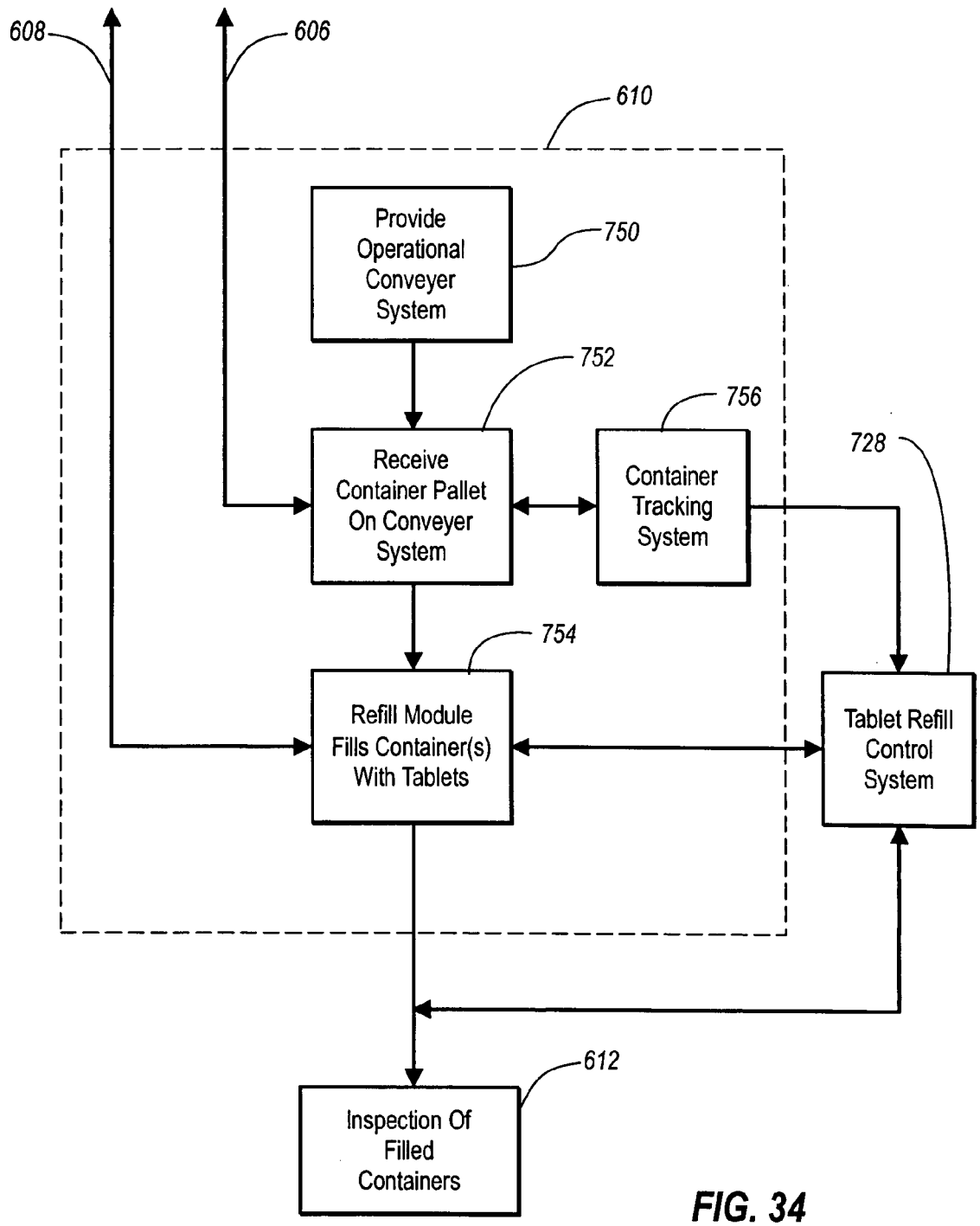

FIG. 34 is a flowchart of an illustrative container filling process.

Figure 35:
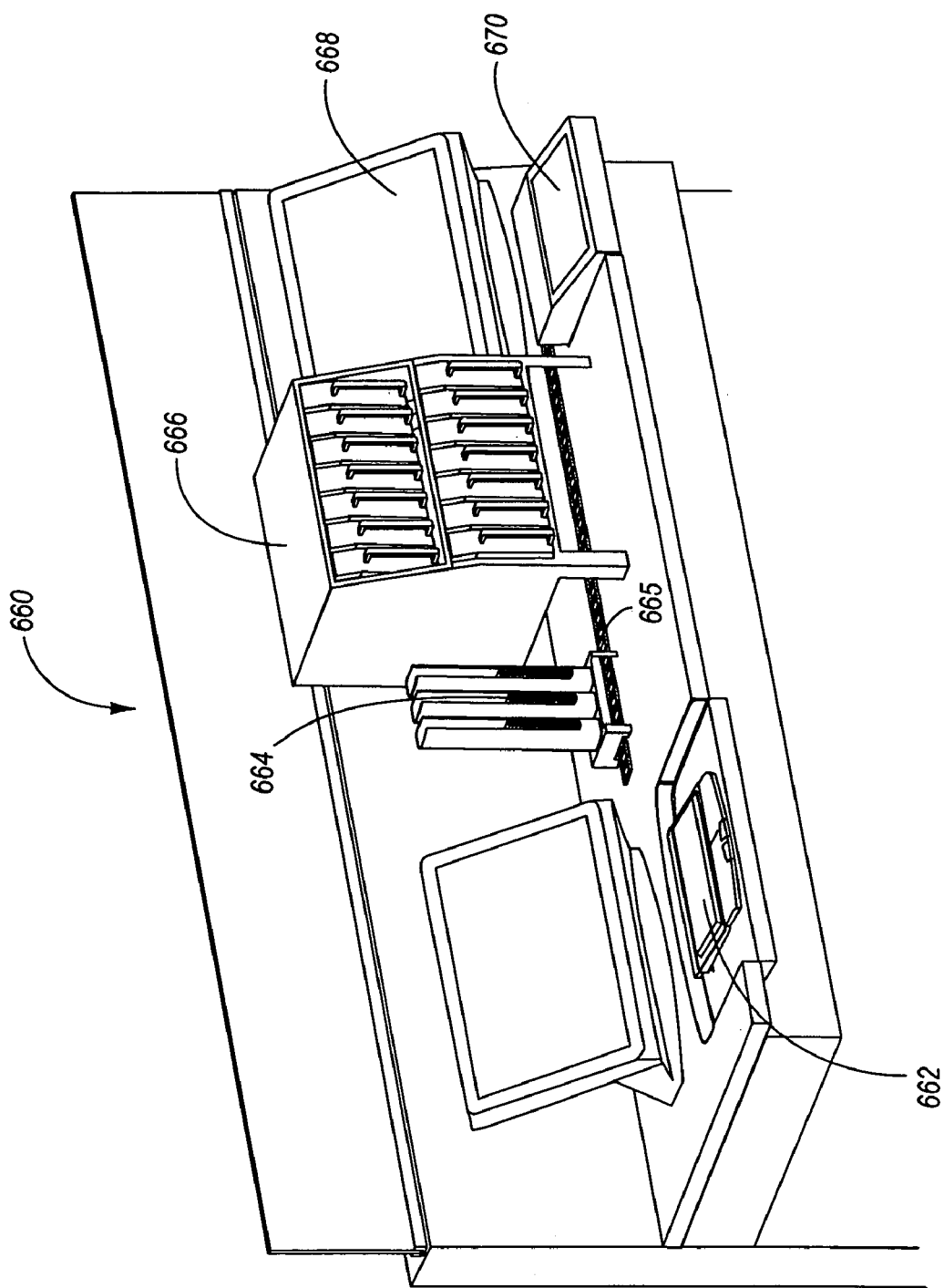

FIG. 35 is an isometric view of an illustrative tabletop system including order processing, pill management, container selection, container inspection, and container filling.

Figure 36:
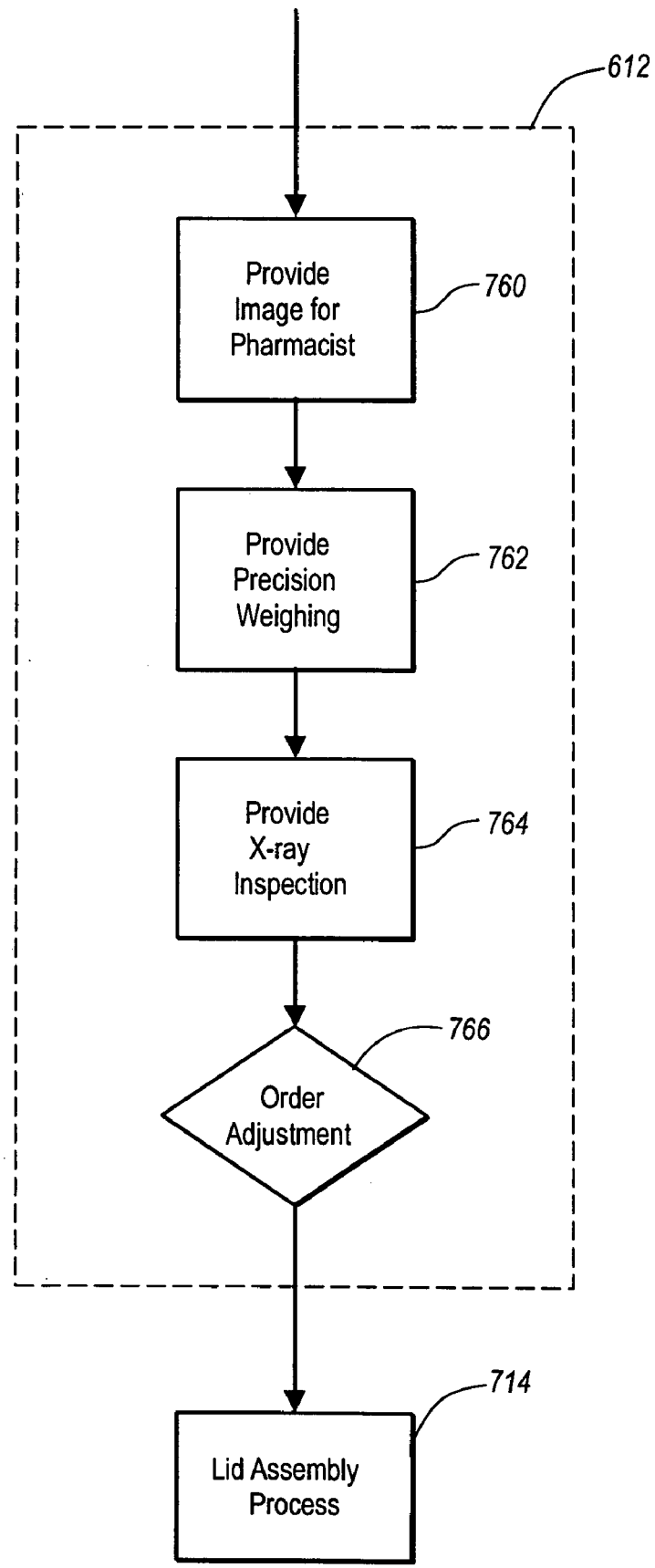

FIG. 36 is a flowchart showing the inspection of filled multiple prescription containers.

Figure 37:
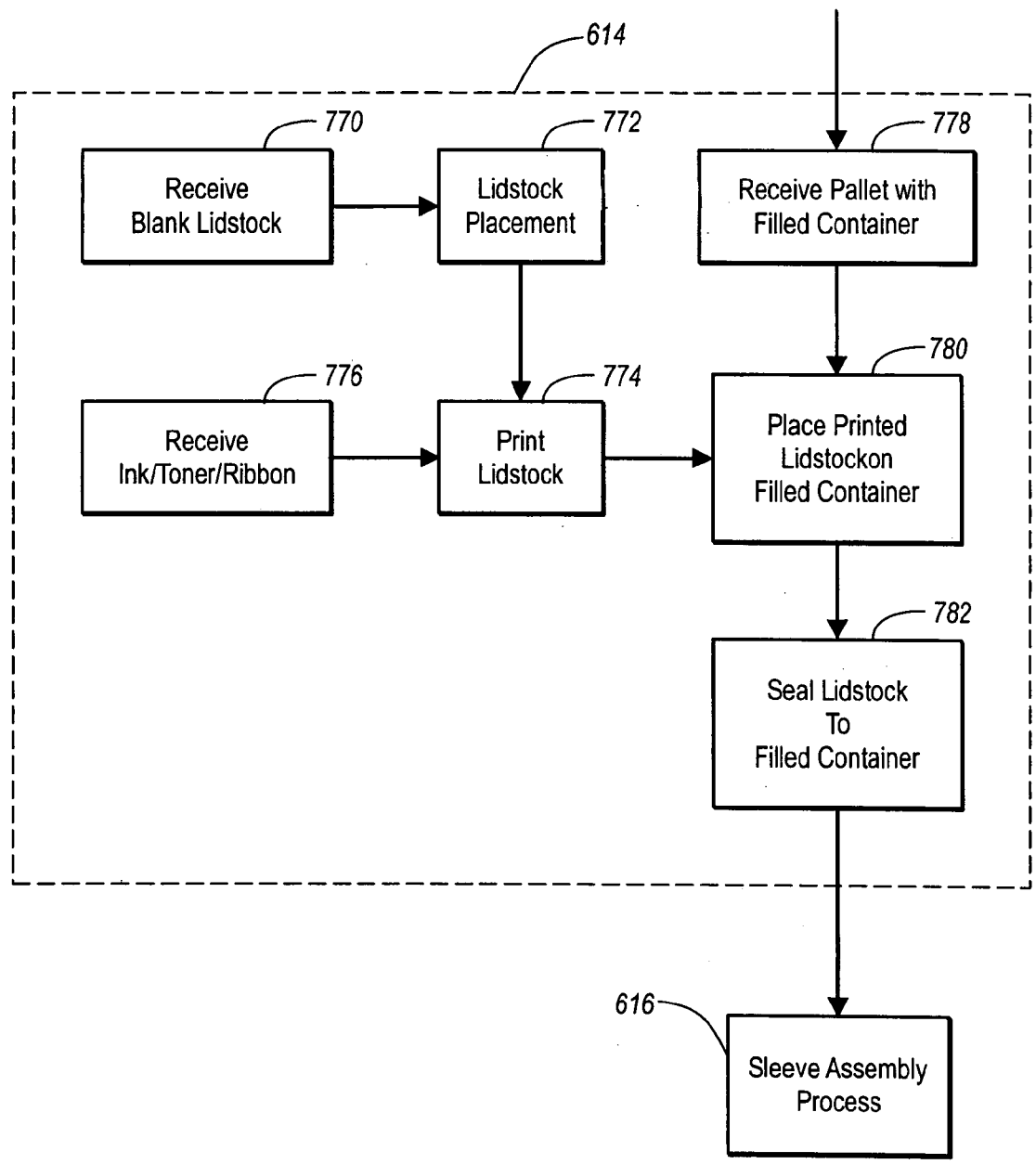

FIG. 37 is a flowchart showing an illustrative lid assembly process.

Figure 38:
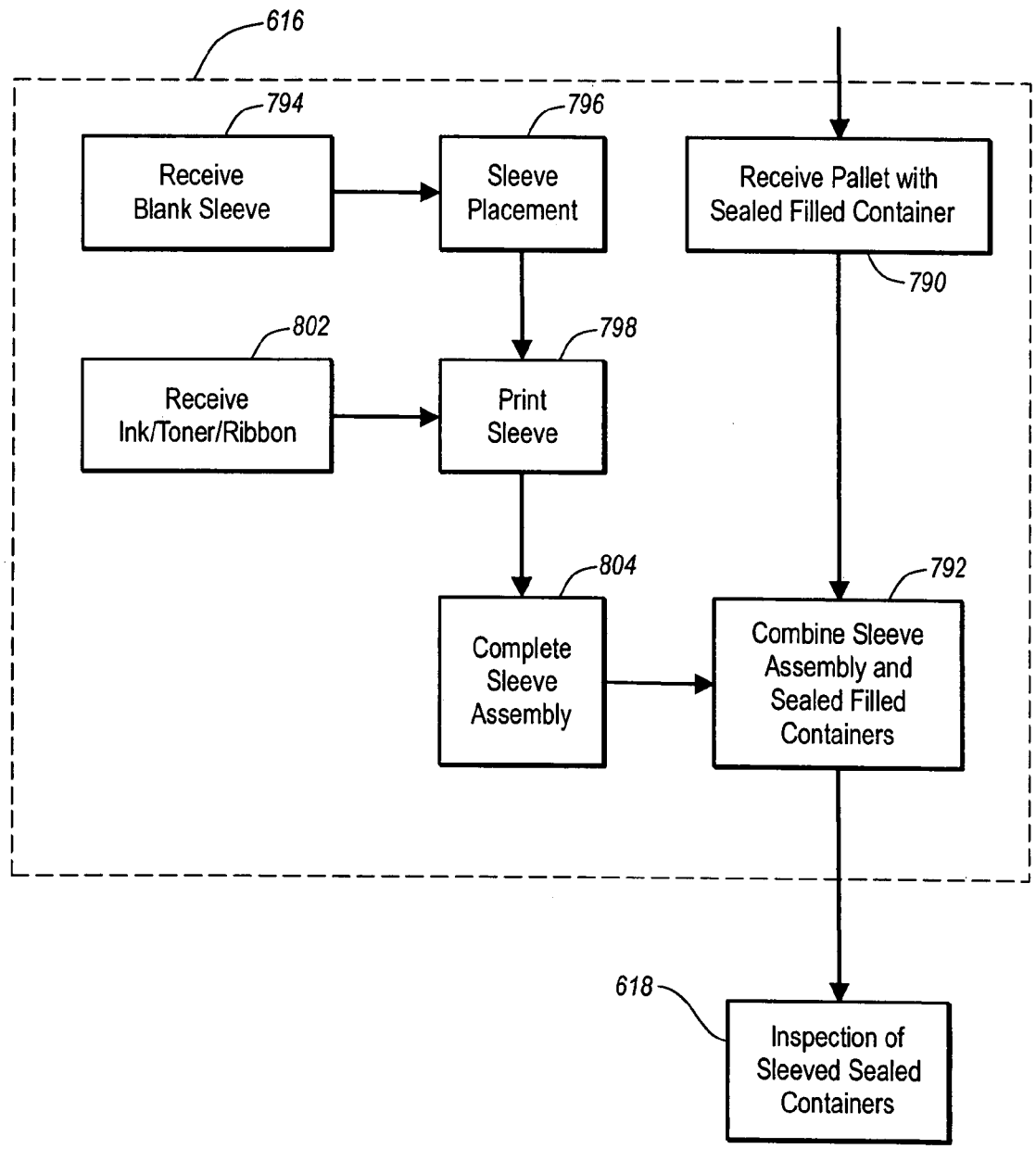

FIG. 38 is a flowchart of an illustrative sleeve or secondary package assembly process.

Figure 39:
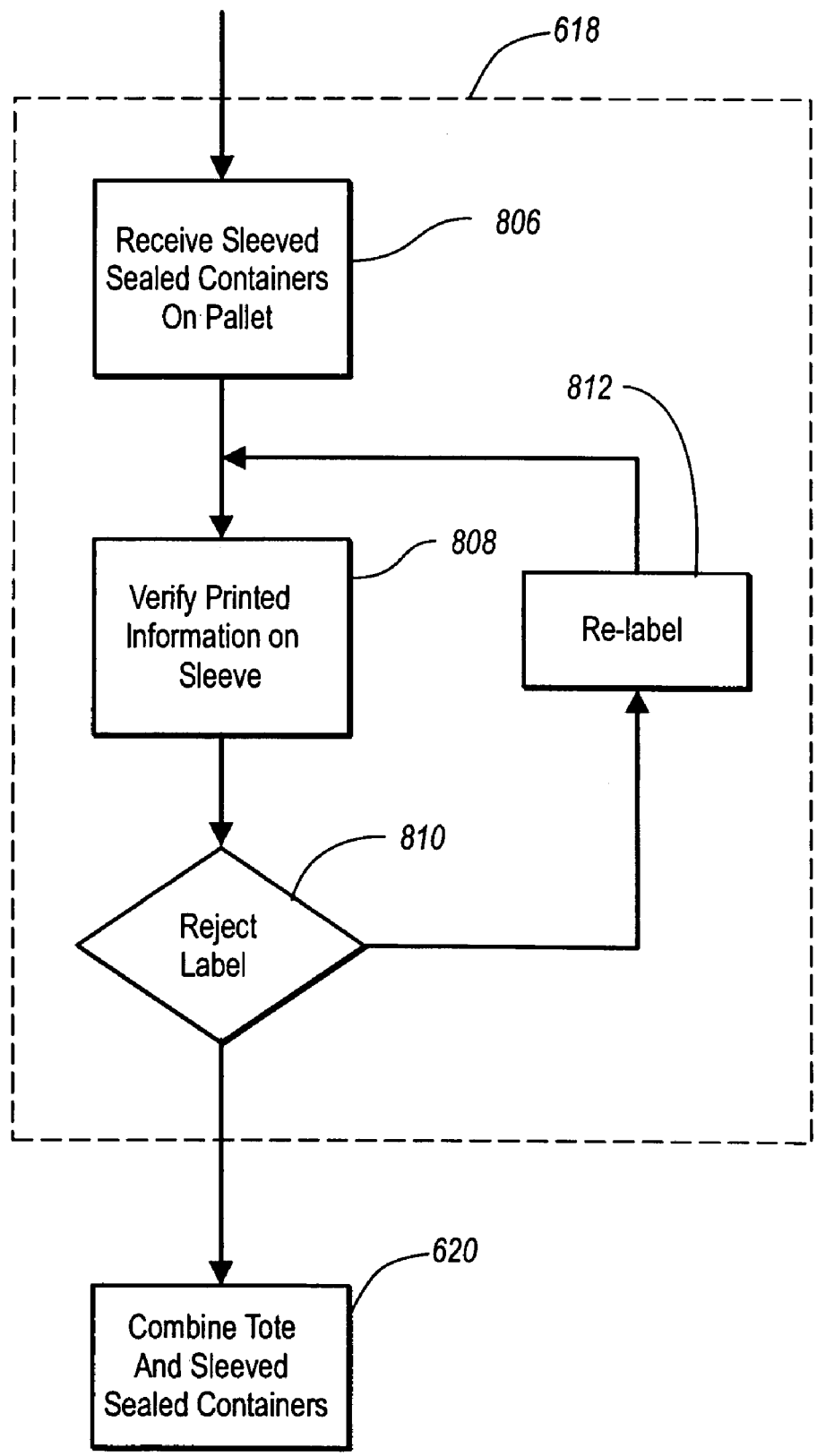

FIG. 39 is a flowchart of an illustrative inspection for of the sleeve or secondary package assembly process.

Figure 40:
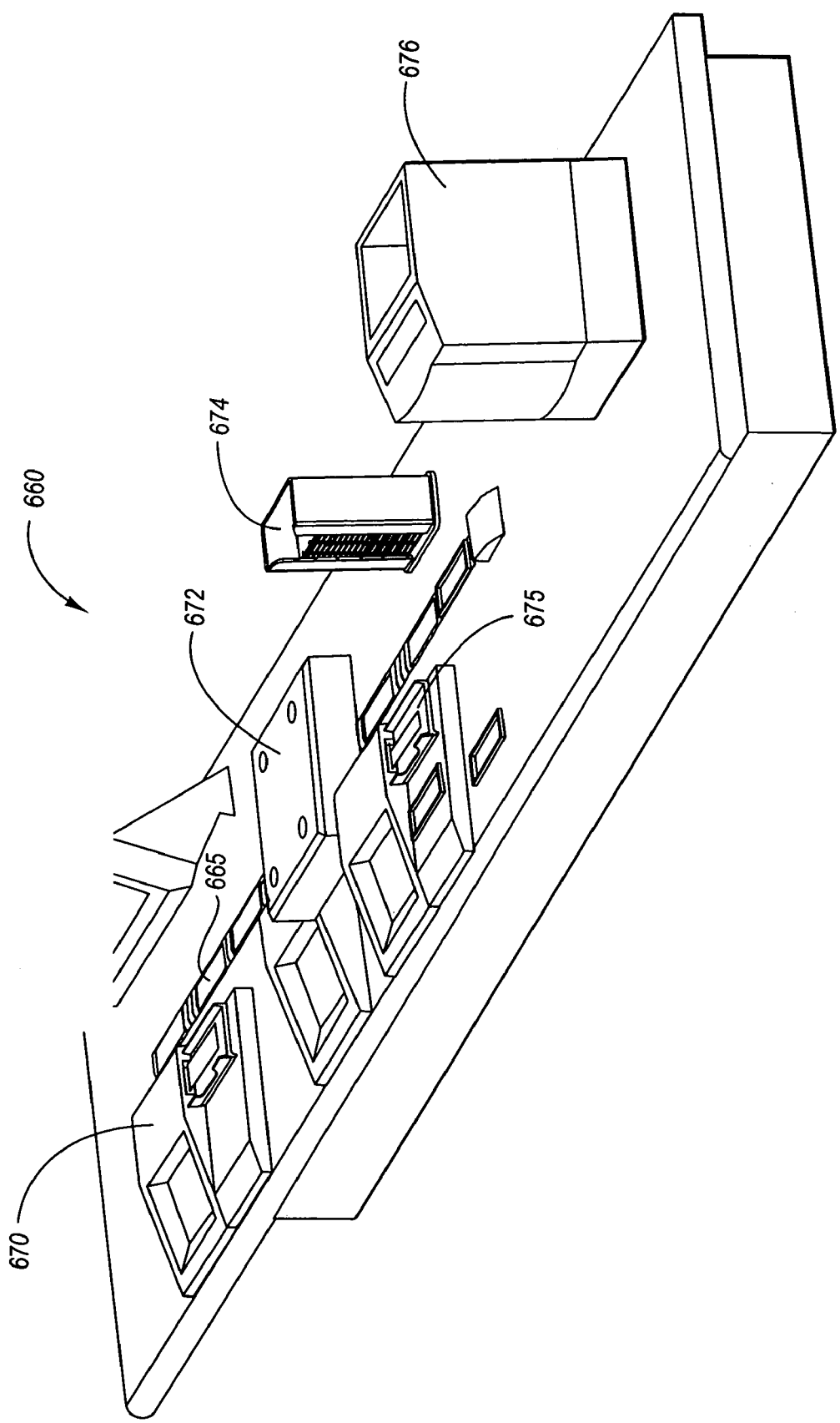

FIG. 40 is an isometric view of the illustrative tabletop system with filled container inspection, lid assembly, sleeve assembly, and inspection of sealed containers.

Figure 41:
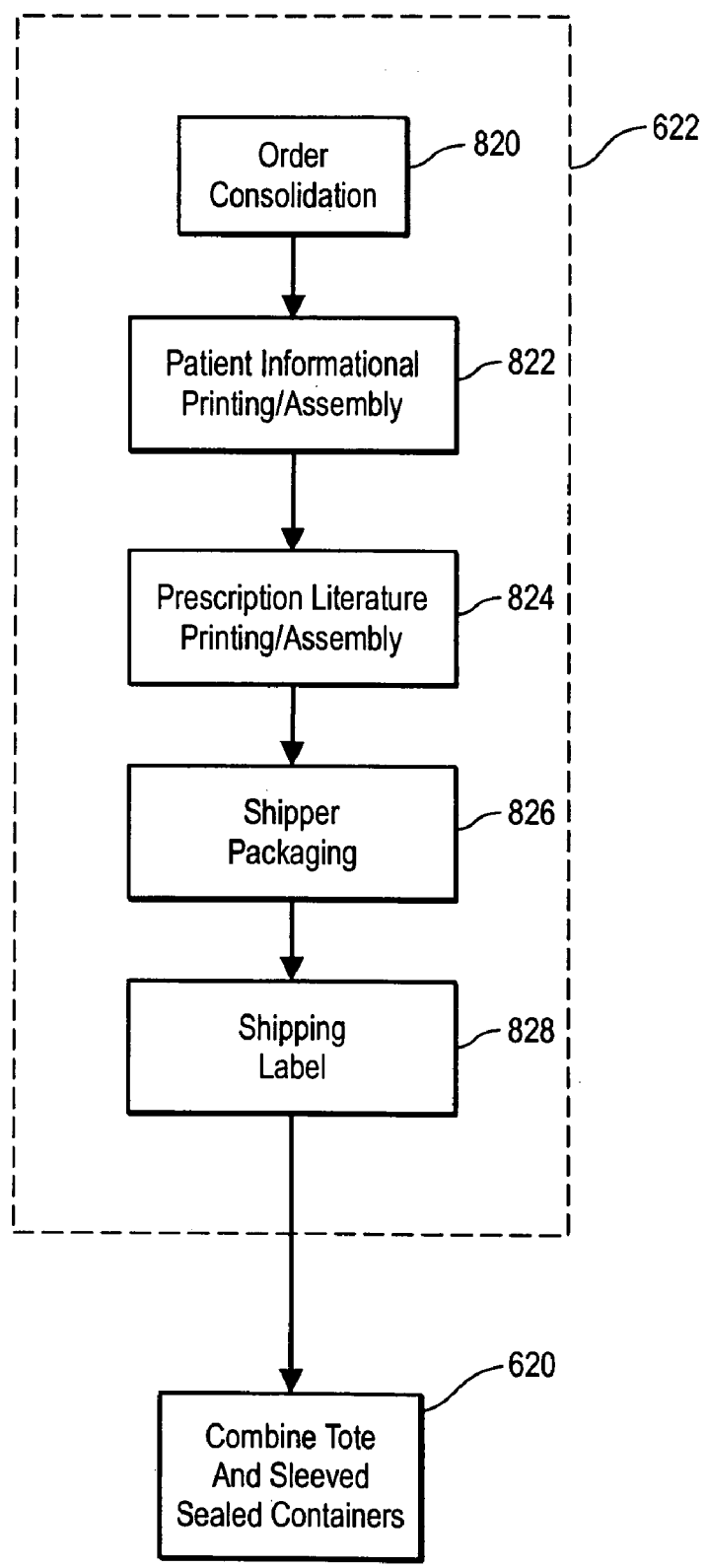

FIG. 41 is a block diagram of a tote assembly system.

Figure 42:
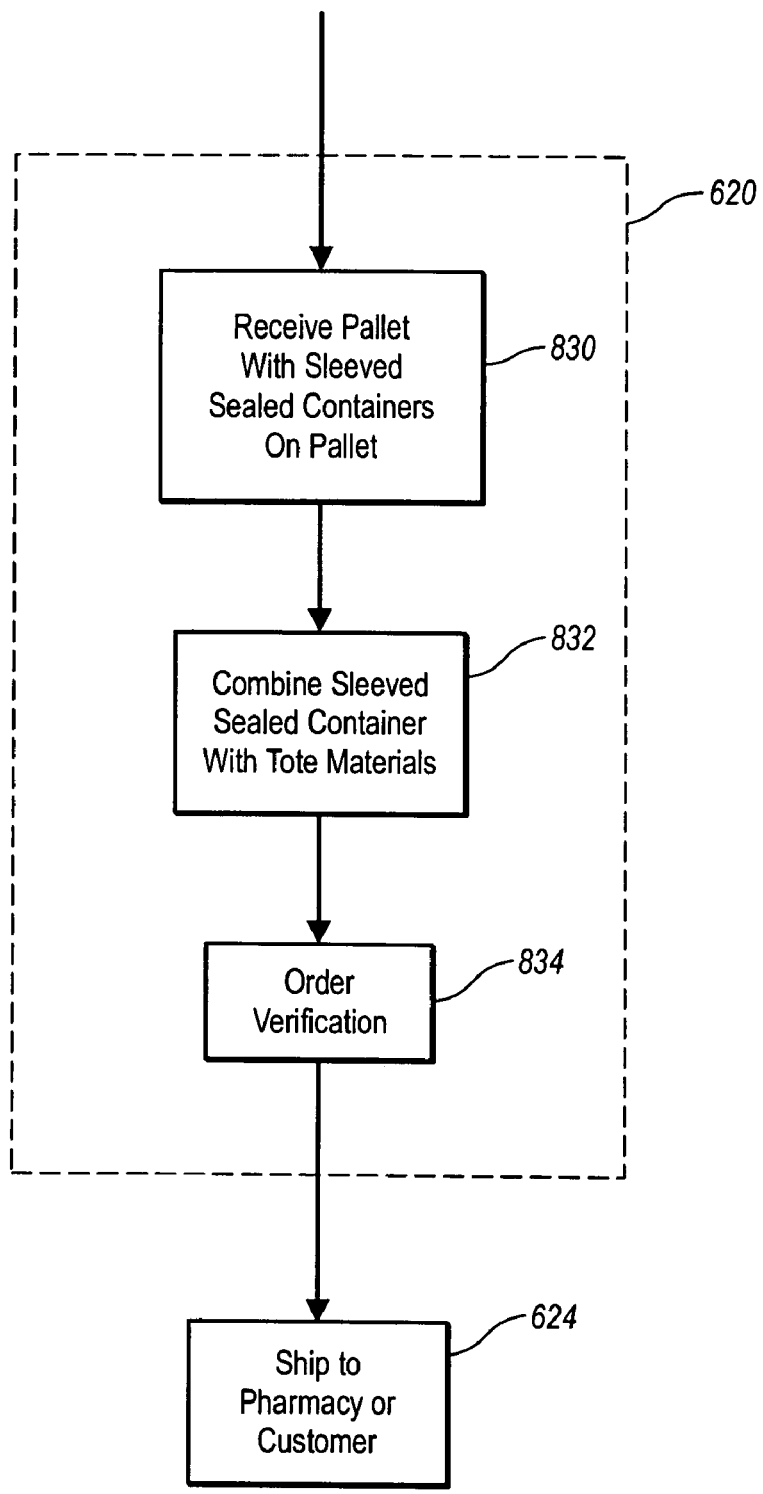

FIG. 42 is a block diagram showing the combining of the tote and sealed multiple prescription containers.

DESCRIPTION

Before the present assembly, apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. Unless defined otherwise, all technical and scientific terms used herein have the same meaning as commonly understood by one of ordinary skill in the art to which this invention belongs.

Figure 1:
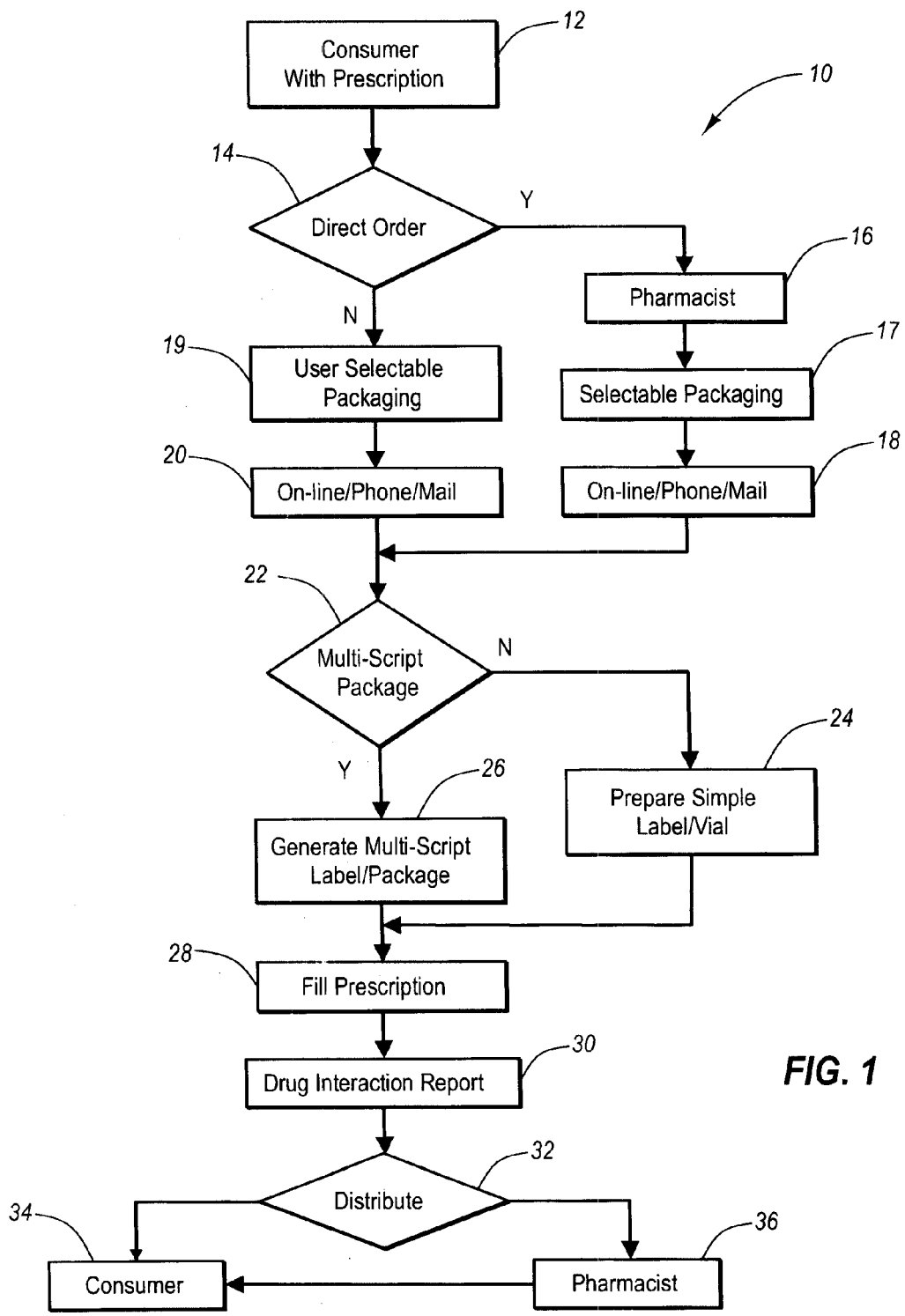
FIG. 1 is an illustrative flowchart showing a method for receiving and processing at least one prescription order.

Referring to FIG. 1 there is shown an illustrative flowchart showing a general method for receiving and processing at least one prescription order. A prescription generally comprises at least one medication that is dispensed as a tablet. The method may be initiated with a consumer having a doctor's prescription at block 12. By way of example and not of limitation, a consumer may be a patient or caregiver. A consumer may also be a person or entity authorized to conduct a transaction for at least one product that includes prescription medication, over-the-counter medication, vitamins, supplements, herbs, oils, or any other such substances. A prescription may not be required for processing a prescription order. For example, a prescription may not required for dispensing certain tablets such as vitamins, herbs, oils, over-the-counter medications, supplements, and other such products. Additionally, in some jurisdictions a prescription for dispensing medications may not be required.

A direct order may then be placed at decision diamond 14. A "direct order" is an order that is placed by a medical professional such as a medical doctor or pharmacist. By way of example and not of limitation, the order is placed using a graphical user interface (GUI) resident on a browser running on a computer that is in communication with the Internet by a pharmacist, patient or caregiver.

If the direct order requires a pharmacist, the method proceeds to block 16 where a pharmacist places the order for the appropriate medications. After block 16, the method proceeds to block 17 where the pharmacist may be prompted for at least one packaging option. A variety of different packaging options may be provided to the pharmacist. The packaging options comprise multiple prescription containers as described in further detail below. Alternatively, as described by block 18, the order may also be placed by telephone, fax, mail, scanned order, or any other such means for placing an order that does not employ a graphical user interface.

If the prescription order can be placed without the need for a pharmacist, the method proceeds to block 19 where the user may be prompted to select at least one packaging option. Generally, the user is either a patient or a caregiver. A variety of packaging options may be provided to the caregiver or consumer, and illustrative packaging options are described herein. As described above, the order may also be placed on-line, by telephone, fax, mail, or other such means for communicating the order.

After receiving an order, the method proceeds to decision diamond 22 where a decision about how to process a multiple prescription order is made. A multiple prescription order or "Multi-Script" order is an order that comprises at least two tablets or medications comprising a first tablet or medication that is different from a second tablet or medication. Generally, a multiple prescription order requires taking multiple tablets or medications at approximately the same time as prescribed, which is also referred to as a prescribed time interval. If the order is not a multiple prescription order, the method proceeds to block 24, in which a single vial is prepared with a simple label. However, if the order is a multiple prescription order, the method proceeds to block 26 where a multiple prescription container is selected and the appropriate label is generated. At block 28, either the simple vial or each of the multiple prescription containers is filled.

At block 30, a detailed label comprising a plurality of written information may also be generated. This plurality of information may include information related to each medication, summary information about each medication, appropriate container labeling, some summary information about the patient, a drug interaction report, or any such combination thereof. The drug interaction report may provide information to help individuals properly take the prescribed medication. The drug interaction report includes information about the various drug interactions that may be associated with each prescription. For example, certain foods may interact with a particular prescription. Additionally, there may be a group of particular drugs that may interact with the prescription, and this information may not be readily available to the patient or the patient's caregiver. The drug interaction report may be used to help identify foods, medications, vitamins, supplements, or any combination thereof that may interact with the patient's filled prescription. The written information may also include a summary of the medications being taken as described in further detail below.

The method then proceeds to decision diamond 32 where a decision is made about how to distribute the combined filled prescription order and detailed label. If the filled order is to be distributed to a pharmacist 36, the pharmacist 36 provides the filled prescription to the consumer 34 that may be a patient or caregiver. Alternatively, the filled prescription may be distributed directly to the particular consumer 34 by shipping to the consumer or having the consumer pick-up the filled prescription order.

Figure 2:
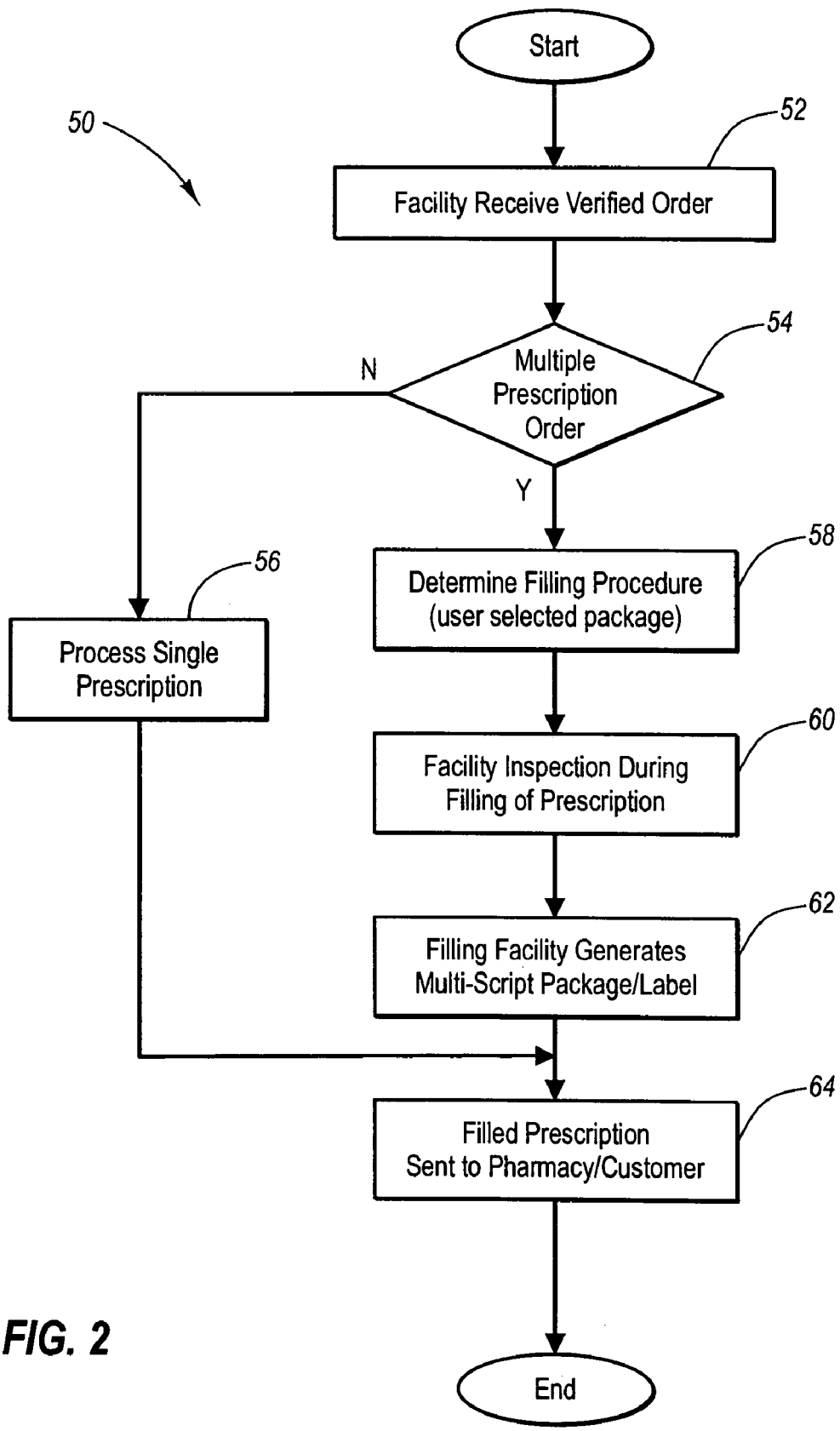
FIG. 2 is an illustrative high-level flowchart of a production facility processing a prescription order.

Referring to FIG. 2 there is shown an illustrative high-level flowchart of a production facility processing a prescription order. Recall, FIG. 1 describes a general method for receiving and processing a prescription order. FIG. 2 provides an illustrative flowchart from the perspective of a production facility processing a verified prescription order. The method is initiated at block 52 where the production facility receives a verified prescription order. A verified prescription order is an order that has been "verified" according to local jurisdictional requirements, insurance requirements, co-pay requirements, transactional requirements, or a combination thereof. For example, in certain jurisdictions a verified prescription order may require a medical doctor's signature, and may have to be processed by a pharmacist. Additionally, a verified order may require approval from an insurance company, Medicare or any such entity. In other jurisdictions, the only form of verification may include confirming that funds are available from the particular individual or organization charged, which satisfies transactional requirements. By way of example and not of limitation, verification of the availability of funds may include simply receiving authorization to charge a credit card and confirming that the credit card is a valid card.

The method then proceeds to decision diamond 54 where a determination is made if the verified order was a multiple prescription order. If the order is not a multiple prescription order, the method proceeds to block 56 where a single prescription order is processed, and then subsequently the filled prescription is sent or provided to a pharmacy or customer as shown in block 64, and described herein.

If the verified prescription order is a multiple prescription order, the method proceeds to block 58 where the facility determines the filling procedure to use. The filling procedure will depend on a host of variables such as the type of user selectable packaging. The method then proceeds to block 60 where the production facility inspects the tablets that have been placed in the multiple prescription containers. The type of inspection depends on the particular design of the production facility. For example, the inspection may be conducted by tablet counters, RFID counters, by using X-ray or near IR technology, visual robotic inspection, weighing the containers or other such technology capable of inspecting the multiple prescription containers that is described herein and that would readily suggest themselves to those of ordinary skill in the art.

After completing the inspection, the production facility generates the detailed label and other labels having the plurality of written information shown in block 62. The written information may also comprise packaging information. The written information may comprise information about each substance, appropriate labeling, summary information, a drug interaction report, or a combination thereof. At block 64, the filled prescription order and the detailed label are combined and this patient-specific combination is then sent or distributed to a designated entity or individual including, but not limited to, the patient, the caregiver, the pharmacist, the user, the customer, or the consumer.

Figure 3:
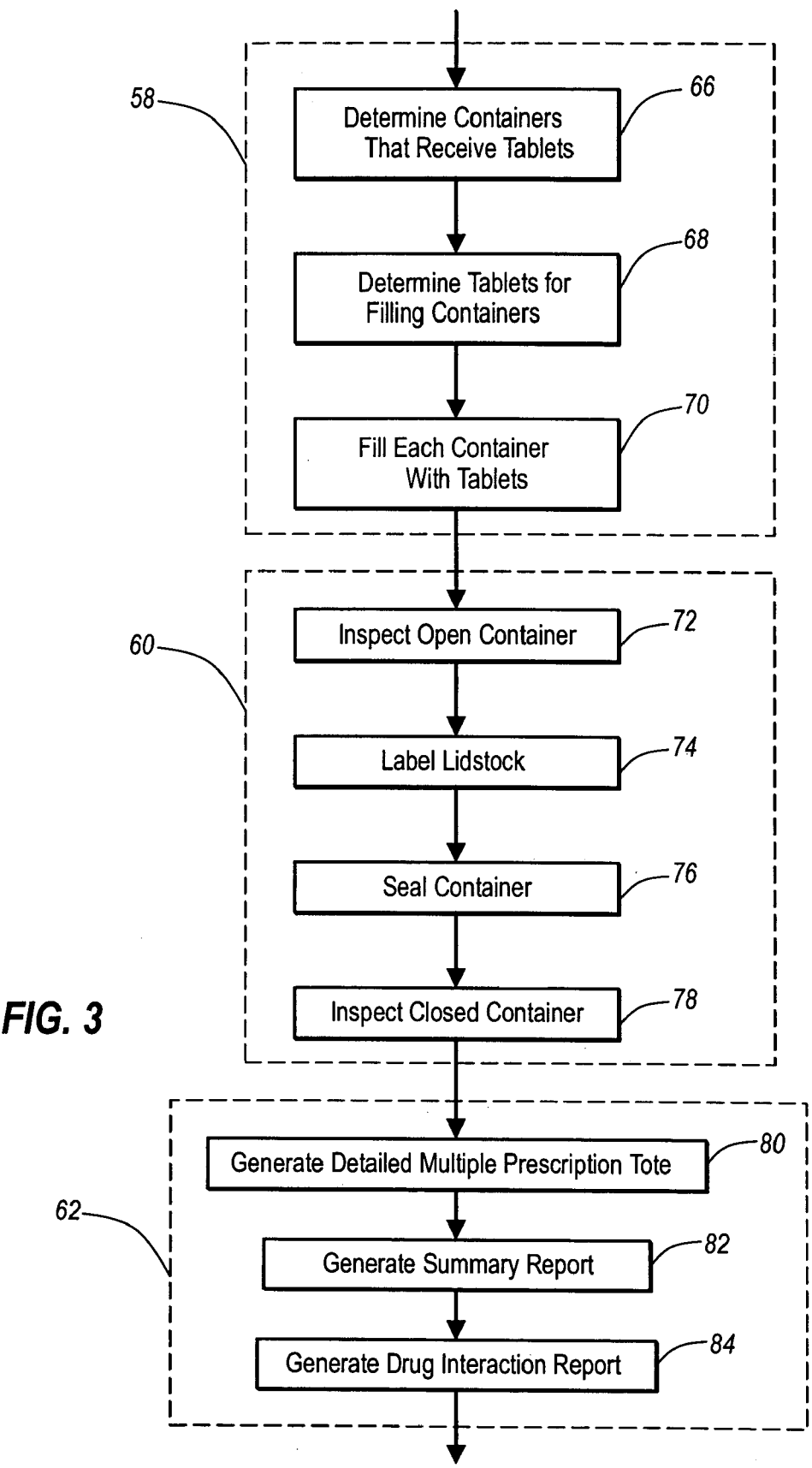
FIG. 3 is a more detailed flowchart showing how a prescription order is processed within the production facility.

Referring to FIG. 3 there is shown a more detailed flowchart of a multiple prescription order being processed within the production facility. A more detailed view of block 58 is shown in FIG. 3, which includes a description of the user selectable packaging that may be determined by the user, consumer, patient, caregiver, or pharmacist. In the illustrative embodiment, a variety of different packaging options are presented. By way of example and not of limitation, the verified prescription order may include 10 tablets taken three times per day, which requires mid-size multiple prescription containers. In another example, the patient and/or user may desire a package design that may be easily used by a caregiver. In yet another illustrative example, the patient may want a package design that is small and portable such as the plastic pouches that are filled with the McKesson PACMED automated packaging system. Based on the patients needs, the appropriate user selectable options may be provided. Thus, an individual requesting the filling of a multiple prescription order will provide sufficient information so that appropriately sized containers or packages are identified as represented by block 66. The containers may be stacked. In certain embodiments, the containers may be placed on a conveyer belt system which allows the containers to travel along the conveyor system to the designated filler module containing the correct medications. The containers may also be placed on trays configured to hold a plurality of containers and situated on a conveyor system which allows the filling facility to track the position of each container within the filling facility.

Additionally, sufficient information is provided so that the appropriate tablets can be associated with the appropriate multiple prescription containers at the appropriate dosing times as represented by block 68. The method then proceeds to block 70 where each of the multiple prescription containers is filled with the appropriate tablets. A more detailed explanation of the method for filling each of the multiple prescription containers is described in further detail below.

A more detailed view of block 60 where the production facility inspects the containers is also described. The inspection may be conducted either before the multiple prescription containers are sealed as represented by block 72. A label may then be printed on lidstock 74 and the multiple prescription container may then be sealed 76 with the labeled lidstock. Additionally, the medications within the multiple prescription container may be inspected after the multiple prescription containers are sealed as represented by block 78. Thus, the filled multiple prescription container may be inspected either before the multiple prescription containers is sealed, after the multiple prescription container is sealed, or both.

A more detailed view of block 62 is also presented in FIG. 3 where after the inspection 60, the production facility generates the detailed labels having the plurality of written information that is patient specific. Additional labeling written information may include packaging information. The detailed label having the written information may comprise information about each substance or medication that is described in the multiple prescription tote 80. The written information may also include summary information about the various medications and is represented by block 82. A drug interaction report may also be generated at block 84.

Referring to FIG. 4 there is shown an illustrative graphical user interface (GUI) for receiving on-line orders that include at least one prescription order that is associated with a particular patient. The illustrative GUI 100 embodiment is configured to receive a prescription order, a direct order, or any such order related to medications, vitamins, supplements, herbs, oils, or any such substance that are associated with a particular patient. The illustrative GUI 100 includes fields for the name of the patient 102 and the patient's address 104. Additional information about the individual placing the order may also be requested, such as the individual's telephone number 106 and e-mail address 108. Information about the patient such as date of birth 110, height 112, weight 114, and sex 116 can also provided to the illustrative GUI 100. The user can input information about the patient's particular medical condition 120, information about the patient's doctor 122, allergies 124, and current medications 126 being taken by the patient.

Furthermore, the user may provide specific ordering options such as instructing about the type of user selectable packaging. For example, a plurality of single packages 128 may be requested for multiple medications. Also, a multiple prescription package 130 or "multi-script" package may be requested. The multiple prescription package may include a variety of user selectable options such as type of package, size of package, and child resistant packaging. The type of package may include a sleeved package or a circular package as described below. Alternatively, the packaging may employ other packaging techniques such as grid packaging or the use of plastic bags also referred to a "pouches." The size of package may also vary and may come in three different sizes: travel (small), notebook (medium), and companion (large).

Data fields are also provided for identifying the requested medications 132 that include a description of the product 134, the dosage 136, the quantity 138, and the type of drug 140. The type of drug 140 may include information about whether the drug is generic or name brand. If the product is available, the on-line ordering system may then provide a price 142 for the product. A sub-total 144 is then provided, and shipping costs 146 are identified if applicable. Note, the GUI may also support customer pick-up at a local pharmacy. A final order total 148 is then presented to the user.

A transactional component that charges for processing the prescription is also provided. By way of example and not of limitation, the patient may then provide a card 150 such as a credit card, a debit card or any other such information for conducting an on-line transaction; the name, the card number, the type of card and the expiration date of the card are requested in the illustrative embodiment.

Referring to FIG. 5 there is shown an illustrative detailed label that is generated by the production facility and combined with the multiple prescription containers. By way of example and not of limitation, the illustrative label 160 may contain printed information that is related to each medication such as summary information about each medication, summary information about the patient, the name of the patient, a picture of the patient, pictures of the first tablet and the second tablet that are to scale, a drug interaction description, or any combination thereof. The illustrative label may be folded and conveniently coupled to a multiple prescription container. For example, the illustrative label 160 can be coupled to a dispensing sleeve, which is described in further detail below.

The illustrative label 160 includes a picture or image 162 of the particular patient, and the patient specific information 164 such as name, address, and telephone number of the patient. Furthermore, there may be additional unique information about the patient printed on the label, such as the doctor's name 166 and telephone number, and health insurance information. The label 160 also includes pictures 168 of the tablets that have been prescribed. Additionally, there may be a particular description 170 about each tablet on the folded label that may include manufacturer's latest labeling information, a summary of expected side effects 172, and a short description of possible drug interactions 174. This information may be presented in a manner similar to the Physician's Desk Reference, which includes a color picture of the pill with summary information about each pill. Additionally, information about how to administer the medication may be provided; this information may be used by a caregiver, to help in dispensing the appropriate medications.

Figure 6:
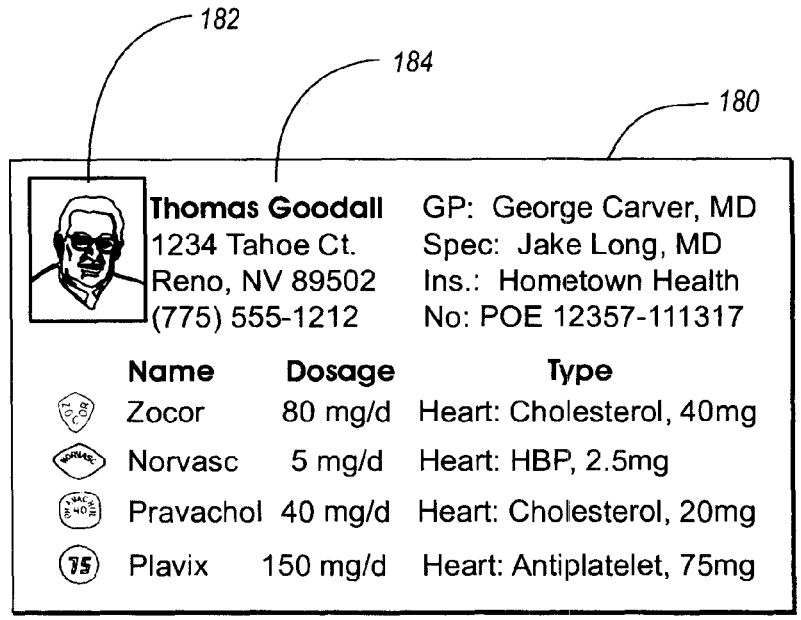
FIG. 6 is an illustrative summary label that may be generated at the production facility.
Figure 7:
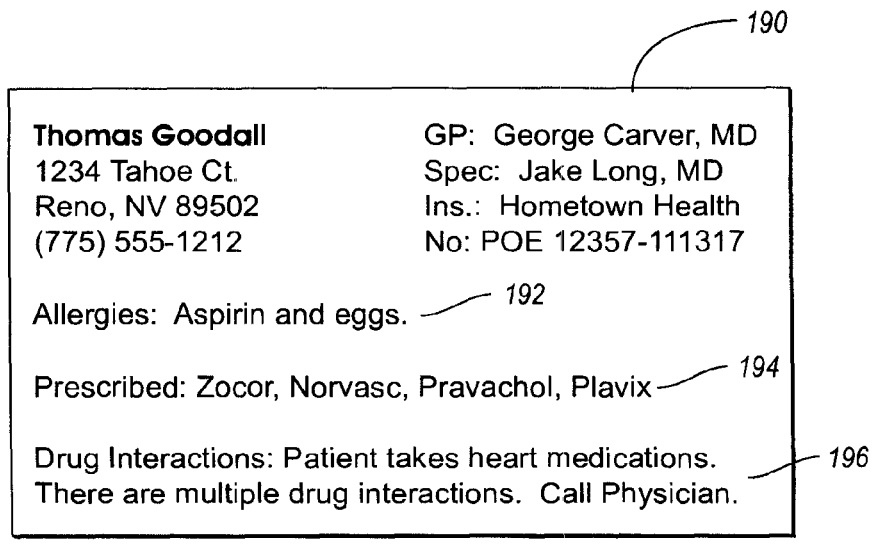
FIG. 7 is an alternative summary label that may be generated at the production facility.

Referring to FIG. 6 and FIG. 7 there are shown two different summary labels that may also be generated at the production facility. In FIG. 6, the summary label 180 may be conveniently configured to fit into a wallet, or may be configured to be attached to the back of an insurance card or driver's license. The illustrative label 180 comprises a picture 182 of the patient, pictures of the first tablet and the second tablet that are to scale, his name and address 184, and other such information. Information about the prescriptions and dosages may be provided with information about the patient's doctors and other health information.

In FIG. 7 an alternative summary label 190 is shown that includes the patient's name, name of the patient's doctors, insurance, and insurance number. Additionally, summary label 190 includes information about the patient's allergies 192, the patient's prescriptions 194, and a warning about possible drug interactions 196. The particular summary label may be dependent on the patient's condition, the patient's caregiver, a physician's recommendation, statutory requirements, or any other such entity charged with assisting the patient.

FIG. 1 through FIG. 7 provide an overview of the systems and methods for processing a multiple prescription order. In the illustrative embodiment an emphasis was placed on performing an on-line transaction. The on-line systems and methods for processing the prescription order are described in further detail in FIG. 8 to FIG. 12.

Figure 8:
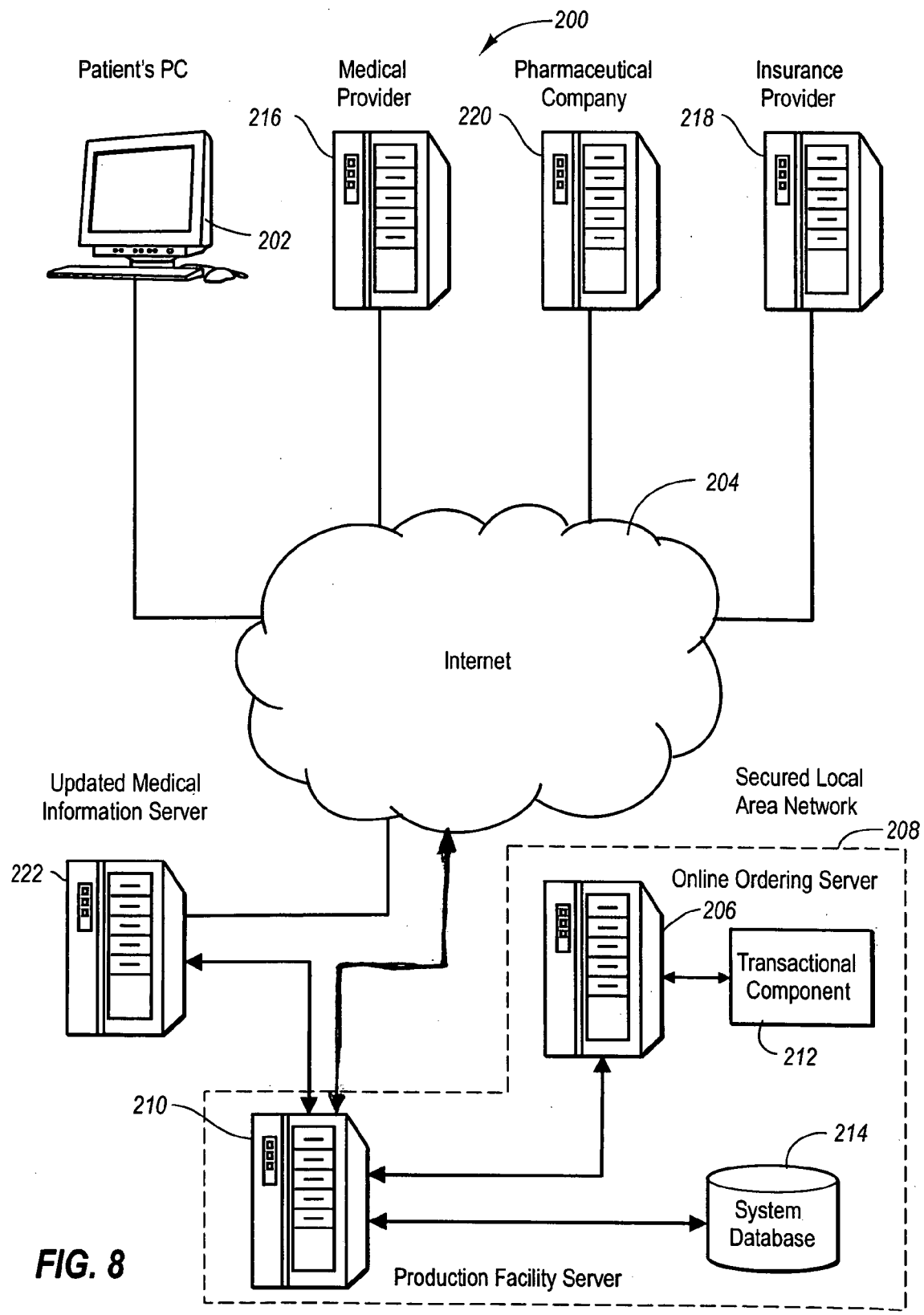
FIG. 8 is a block diagram of an illustrative system that receives a prescription order via the Internet.

Referring to FIG. 8 there is shown a block diagram of an illustrative system 200 configured to receive a prescription order via the Internet. The illustrative patient's personal computer (PC) or "client" 202 displays the illustrative GUI 100. The illustrative client 202 is communicatively coupled to the Internet 204. By way of example and not of limitation, a standard off-the-shelf personal computer and operating system would operate as a client.

The PC 202 is configured to remotely communicate with an online ordering server 206. By way of example and not of limitation, the online server 206 is behind a firewall and is part of a secure local area network (LAN) 208 located at a production facility. Generally, the production facility is configured to generate a filled multiple prescription order. The secure LAN also comprises a production server 210. In the illustrative example of FIG. 8, the production server 210 and online server 206 are both housed in the production facility. An alternative embodiment in which the online server is located in a separate location is described below in FIG. 9.

The online ordering server 206 is communicatively coupled to the production server 210. The online ordering server 206 is configured to communicate with the user and/or clients that are placing the on-line order. The ordering server 206 also contains the hardware and software necessary for addressing queries about inventory in the production facility. The online server 206 may be configured to query the user about a particular prescription, about health insurance, and other pertinent information. The online server 206 may comprise software and hardware that permits the client 202 to pull up notes, research the prescribed medication(s), research side effects and drug interactions with other medications, vitamins, foods, and other such information that would help the patient properly consume the products ordered by the patient.

The production server 210 controls the processing of the multiple prescription orders at the production facility that generates containers having a plurality of different tablets in each container. The illustrative production server 210 comprises a system database 214 that stores information about the products available at the production facility such as prescription medication, over-the-counter medication, vitamins, supplements, herbs, oils, or other such substances. Additionally, the system database 214 may include historical prescription information that is associated with the patient, so that the user may access the multiple prescription order at a later time for ordering refills. In one illustrative example, the production server contains and maintains all the information to control the production facility. The production server 210 may be configured with management software that manages all the filling, inspection, printing, sealing, order tracking, and tablet assembly traffic control functions.

While placing an order, the online ordering server 206 may request information from a medical provider server 216 or provide information to the medical provider. For example, a medical provider such as a medical doctor or nurse can confirm that a specific medication has been ordered and will be administered in a particular manner. Additionally, the medical provider may also include notes for the patient on how the medicine should be taken, and this information may be printed by the production facility and associated with the patient's on-line order. Additionally, historical prescription order information may also be stored on the medical provider server 216.

The online ordering server 206 may also request information on the accuracy or changes in the end user's medical insurance from the insurance provider server 218. The online ordering server 216 may also request information from the pharmaceutical company server 220 about certain prescribed medications and updated information that pertains to the prescribed medications. These queries to the pharmaceutical company server 220 may occur during the online ordering process initiated by the end user or at various times when updating the system database. Additional queries may be made to government agencies, private medical facilities, on-line search engines, websites, databases, or any combination thereof.

The online ordering server 206 and/or the production facility server 210 may also be communicatively connected to an updated medical information server 222 via the Internet or a secure wide area network connection. The updated medical information server 222 may be a private or government maintained server with compiled updated information on the various drugs stored in the production facility. The updated information may comprise new warnings on drug interactions, updated expiration dates, toxicity information and the like. The updated information is communicated to the second labeling component. This information is valuable in assuring the multi-drug prescriptions are effective and safe.

Additionally, the online ordering server 206 comprises a transactional component 212 that processes the user's financial information. The transactional component enables the online ordering server 206 to obtain pertinent information from the user, healthcare provider and the user's insurance company to verify the prescription. The transactional component is also configured to carry out the payment of the order and informs the user if the prescription has been processed or if the financial transaction has failed.

Figure 9:
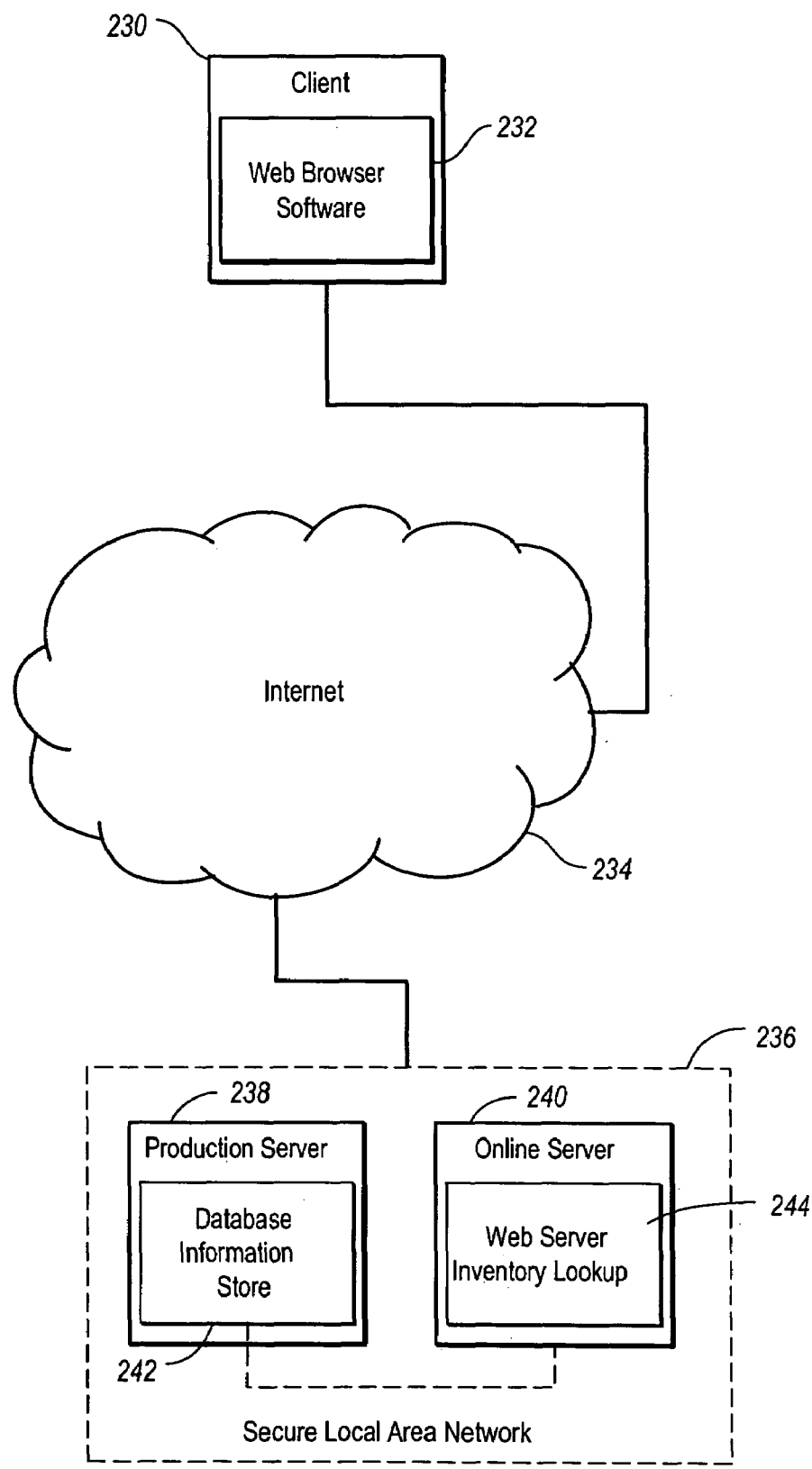
FIG. 9 is a block diagram of a client server architecture that communicates the filling of the multiple prescription order to a production facility.

Referring to FIG. 9 there is shown a block diagram of a simplified client server architecture in which the multiple prescription packaging is sourced to the production facility. In this embodiment, the user requests a prescription refill from a client 230 computer that displays a GUI viewed using a standard web browser 232, and the client 230 is communicatively connected to a wide area network (WAN) such as the Internet 234. The client 230 then proceeds to access the web site that displays the illustrative GUI 100. The client 230 computer may be a portable terminal, a notebook computer, a hand-held personal digital assistant, or other such device that can be networked and can process browser software. It shall be appreciated by those skilled in the art that the end user of the GUI may be a patient, parent, caregiver, physician, hospital personnel, or any other person that has permission from the patient to access their prescription data.

The client 232 then proceeds to communicate with the secure LAN 236 that comprises a production server 238 and an online server 240. The production server 238 is associated with managing the inventory in the production facility and comprises an inventory database module 242 that determines if the production facility can satisfy the client's prescription order.

The online server 240 may be located in a variety of different places such as a separate on-line pharmacy, a physician's website, a healthcare provider's website, a health insurance website, a school, a university, or any other such entity that out-sources the multiple prescription packaging to the production facility described herein. In the illustrative embodiment, the online server 240 comprises a web server inventory lookup module 244 that is operatively coupled to the inventory database module 242 and receives updates regarding the production facility's ability to satisfy the client's request.

In operation, the client 230 may access the production server 238 directly or through the illustrative online server 240 that may be associated with a separate on-line pharmacy, a physician, a health care provider, a health insurance provider, a school, a university or any other such entity. Additionally, physicians involved in the patient's care may utilize the Internet to generate a new prescription for the patient, or modify a previous prescription that may be stored on the production server 238.

Patient confidentiality may be preserved by using encryption technology and by requiring strong authentication. Using encryption technology such as Secure Sockets Layer (SSL) and Public Key Infrastructure (PKI), communications across the Internet are kept secure. Illustrative embodiments may use available encryption tools such as Pretty Good Privacy (PGP), OpenPGP (the IETF's RFC 2440) and other available PKI encryption standards. Information stored on databases and servers may also be encrypted. Strong authentication may be obtained by asking the user for one or more unique identifiers such as date of birth (DOB), unique IP address, last 4 digits of a social security number, username, password, or any other such unique identifier.

Once the client 230 has been authenticated, the client is able to place a multiple prescription order using the illustrative graphic user interface (GUI) 100. In one illustrative example, a local pharmacist's on-line server communicates with the production server 238 and the inventory database 242. The pharmacist's on-line server makes a request to determine whether the production facility can satisfy the pharmacist's order. The inventory database 242 is accessed to determine if the prescription order may be filled. Once the pharmacist's online server has received confirmation that the prescription order can be filled, the online server relays this information back to the clients computer via the Internet.

By way of example and not of limitation, the illustrative production server 238 comprises software to access the drug interaction database to determine if there may be possible interactions between the prescribed tablets stored. The production server 238 also communicates the order to production facility computers which control the various systems and subsystems involved in producing the multiple prescription containers, including printers for labeling the lidstock on each individually sealed container with medication instructions such as date and time to take the tablets in each individual container. The production server 238 may also communicate to production facility computers which are connected to a printer for generating labels with patient specific information, drug information and expiration date(s) for the medication stored within the individual containers. It should be noted that vitamins and herbal supplements may also be stored together with prescription drugs.

Figure 10:
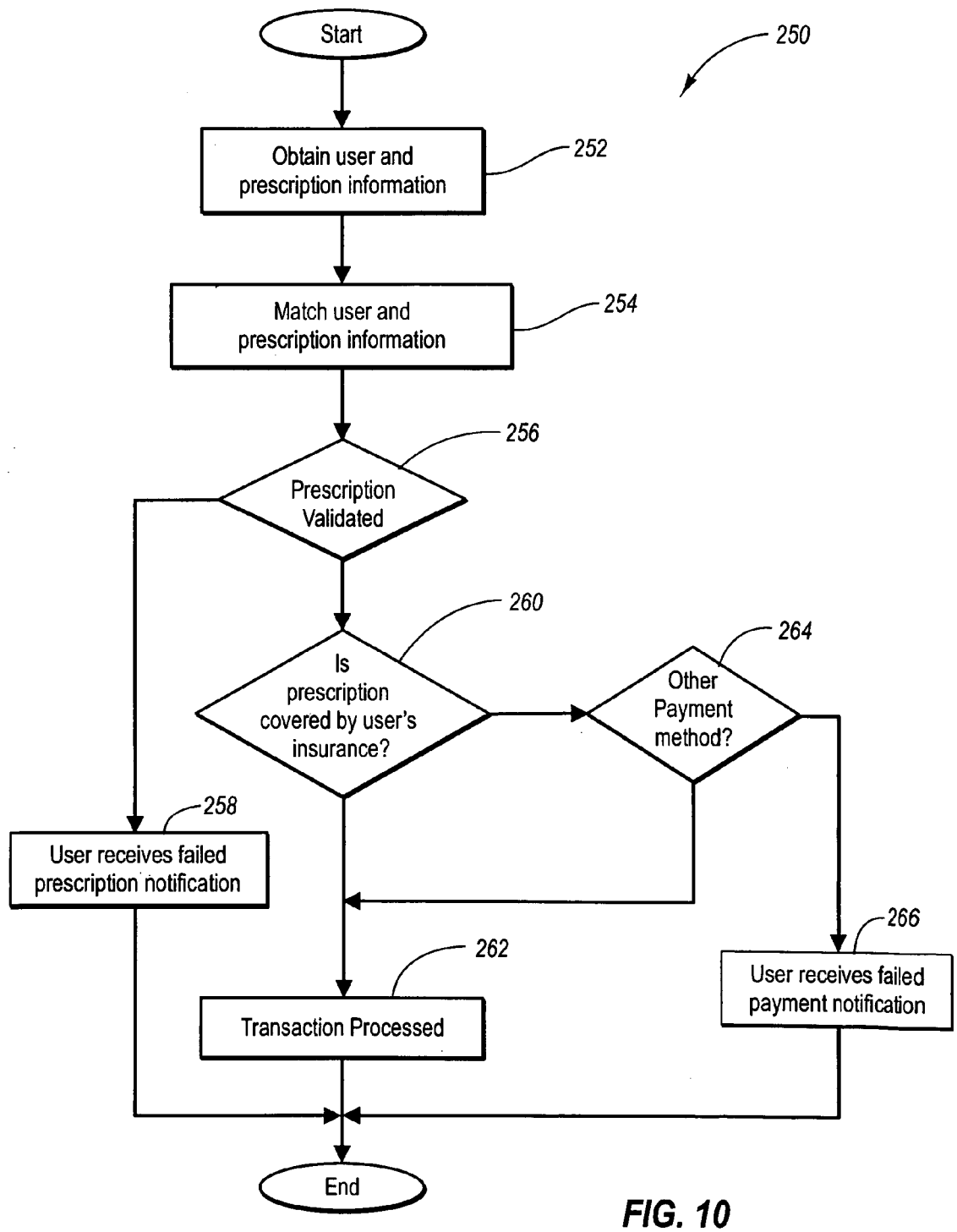
FIG. 10 is a flowchart showing a prescription validation process.

Referring now to FIG. 10 there is shown a flow chart of an illustrative prescription validation process 250. The prescription validation process is initiated at block 252 where user information and prescription order information is provided to either illustrative online server 206 or illustrative online server 240. The method then proceeds to block 254 where user information is matched against the prescription order information.

At decision diamond 256, the prescription order is validated if user information and prescription information also match information stored on the online server. Additionally, the prescription may be validated after the online server communicates with another server such as the medical provider's server. Alternatively, the prescription order may be simply validated if the user information matches the prescription information. For example, if either the patient information or the prescription order information does not match the information stored on the online server, then the method proceeds to block 258 where the user receives a failed prescription notification. By way of example and not of limitation, an explanation may be provided by the online server such as the patient's personal information is incorrect, or the prescription has expired, or a physician's examination is required before filling the order, or the patient needs to wait a couple more days before the prescription order may be filled. Those skilled in the art shall appreciate that the user information and prescription information may require being input more than once before a failed notification is provided to the user.

If the prescription order is validated by having the patient information match the prescription order information, the method proceeds to decision diamond 260 and determines if the prescription order is covered by the user's health insurance. As with prescription information, the insurance information for a specific user may be stored on a database associated with the online server of the production facility or the health insurance company's server may be queried by the online server via secured network about the accuracy of the user's insurance policy such as determining if the insured's policy is up-to-date. Additionally, information about the medications covered by the specific insurer may be queried, co-payment information, prescription drug policy, secondary insurance information, or any other such pertinent insurance information.

If the prescription order is paid for partially or fully by the user's health insurance, the method proceeds to process the transaction at block 262. A more detailed view of the transaction process 262 is provided below in FIG. 11.

The prescription order may not be covered, or may only be partially covered by the user's insurance and so the method proceeds to decision diamond 264 where alternative payment methods can be provided. By way of example and not of limitation, alternative payment methods include VISA transactions, debit card transactions, ATM transactions, PayPal transactions, Electronic Fund Transfers, and other such methods for performing on-line transactions. If the alternative payment method can be processed, the method proceeds to block 262 where the transaction is processed. However, if the alternative payment method can not be effectively processed, the method proceeds to block 266 where the user receives a failed payment notification.

Figure 11:
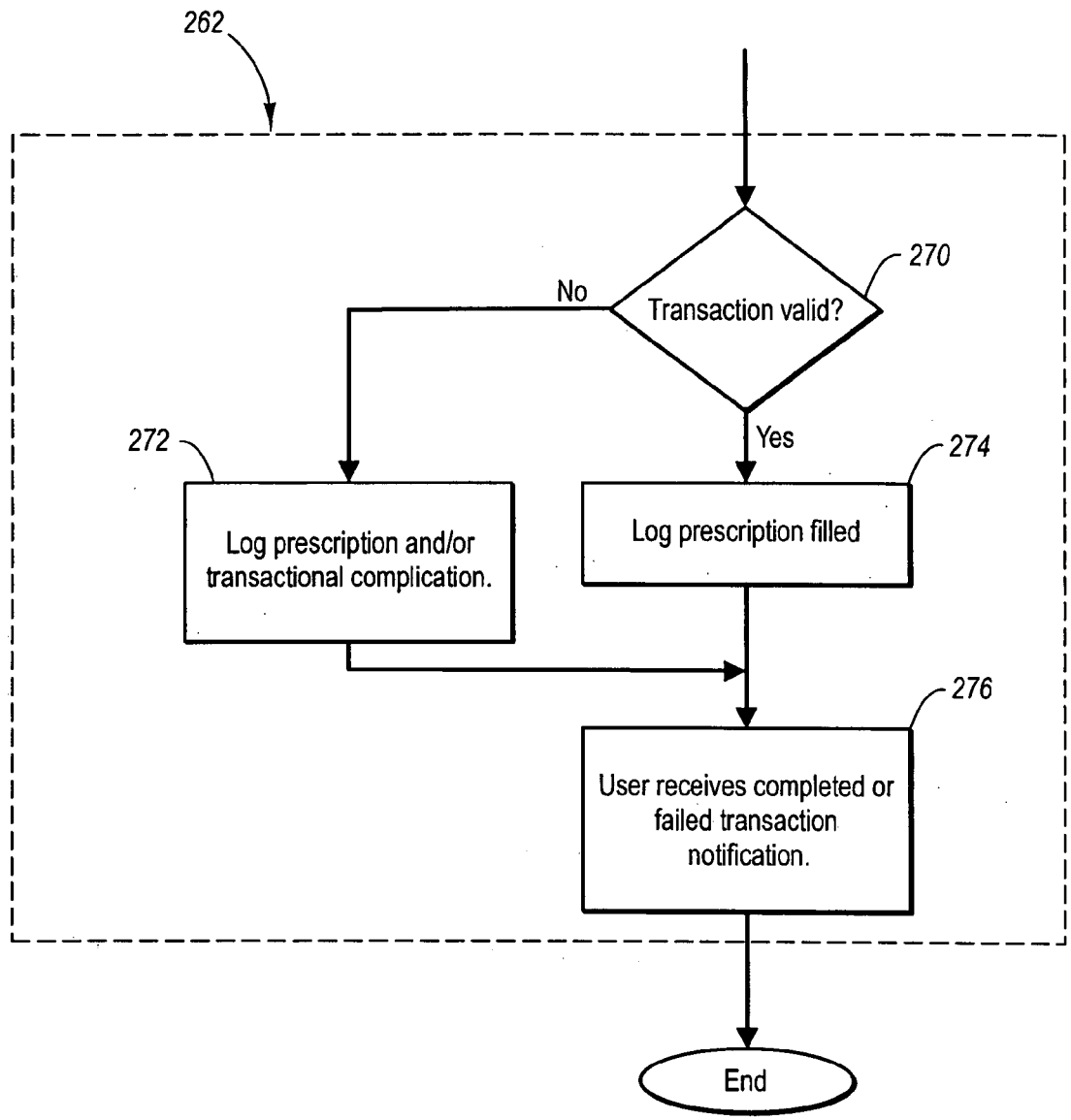
FIG. 11 is a flowchart showing a transaction being processed.

Referring to FIG. 11 there is shown an illustrative method for processing an illustrative transaction in block 262. At block 262, the online transaction is processed, which enables the online server to send confirmation that the prescription order has been filled. The method is initiated at decision diamond 270 where a determination is made concerning whether the transaction is valid. A transaction is valid when the information for payment of the multiple prescription order has been authenticated.

If a determination is made that the transaction is not a valid transaction, the method proceeds to block 272 where a log of either the prescription complication, transaction complication, or both is recorded. The prescription complication may arise because the production facility can not satisfy the order. The transactional complication may be caused by the payment method not being authenticated.

If the transaction is valid, the method proceeds to block 274 where the log indicates that prescription has been filled. The processing of the online transaction may also comprise confirming that the drugs requested are in the production facility's inventory and ready for dispensing. Inventory information may be stored on either the online server or the production server or on any other communicatively connected database or computer associated to the transaction component of the online server.

After determining whether the transaction is valid, the method proceeds to block 276 where the user receives a completed or failed transaction notification. In the illustrative example, the failed transaction notification comprises information explaining to the user that the transaction failed because an invalid credit card number was provided. If the transaction is determined to be valid, the prescription is logged as filled and the user receives a prescription completed notification via the network connection between the online server and the user's computer.

A multiple prescription container assembly comprises a plurality of containers that are configured to receive a plurality of medications, even though a single prescription may reside within an individual container. The multiple prescription container assembly is configured to dispense a plurality of different tablets to a particular individual. The illustrative multiple prescription container assembly comprises a plurality of containers made from a single piece of moldable material wherein the containers are ordered to permit sequential dispensing. At least one of the containers is configured to receive a first tablet associated with a first medication, and a second tablet associated with a second medication that is different from the first medication; the first tablet and the second tablet to be taken at approximately the same time by the particular patient, which is also referred to as a prescribed interval. By way of example and not of limitation, there is a flange on the top surface of each of the containers. The multiple prescription container assembly also comprises a plurality of lids, the lidstock configured to interface with the flange of each integrated container. Each lid seals each of the containers and has a surface that receives a printable indicia with specific information regarding the particular individual. Additionally, the multiple prescription assembly comprises a sleeve or "secondary package" that is coupled to the plurality of sealed containers wherein the sleeve is configured to permit sequential dispensing for each of the sealed containers.

Figure 12:
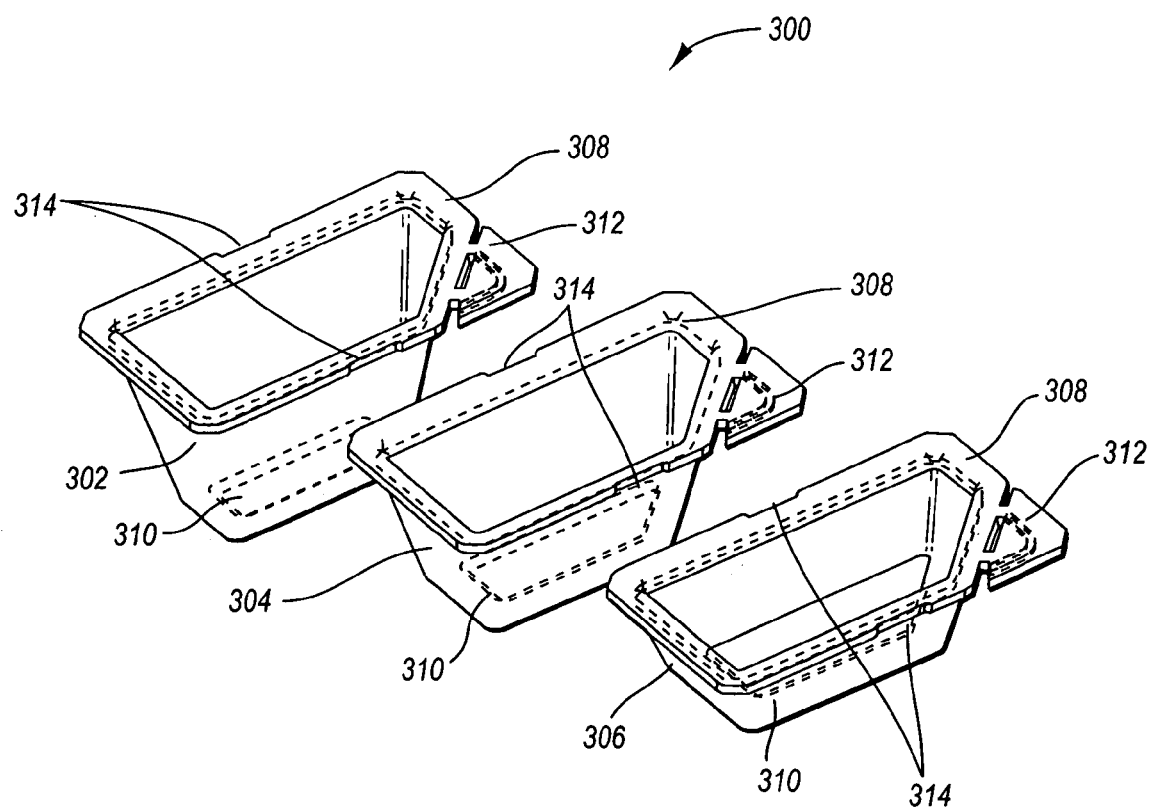
FIG. 12 is a diagram showing an illustrative multiple prescription container having various depths.

Referring to FIG. 12 there is shown a first embodiment of a plurality of illustrative containers 300 having various depths that are configured to receive a plurality of tablets. The three individual containers 302, 304, and 306 are identical except for the depth of the cavity of the containers. The flanged top surface 308 and the bottom surface 310 are the same on all three containers shown in FIG. 12, and are configured to make the various sizes of containers stackable. Each of the containers further comprises a breakaway tab 312 on the sealing flange 308. The tab provides a handhold for easy opening and peeling back the lid from the container. Each of the containers also comprises a plurality of indentations 314 on at least one edge of the flanged top surface 308.

Each of the illustrative embodiments 302, 304 and 306 is an element of the multiple prescription container that stores tablets. It should be noted that a "tablet" is a small article which is swallowed. A tablet includes pills, capsules, and caplets. A tablet may also be a solid dose of medication or supplement, i.e. pill, tablet, capsule or a liquid dose of medication, e.g. Vitamin E or (cod liver oil) provided in a capsule. In general, a tablet may be a prescription medication, supplements, or any other such article that is intended to be ingested to improve a user's health or wellbeing. A tablet may also be medication in the form of a suppository, or vitamins, herbal supplements and the like.

Figure 13A:
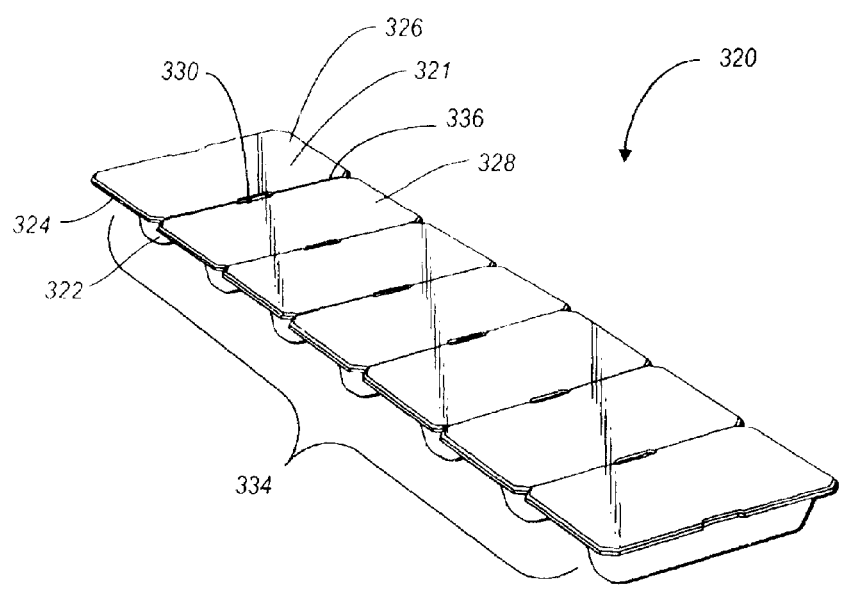
FIG. 13A and FIG. 13B shows a top view and a bottom view of a group of prescription containers.
Figure 13B:
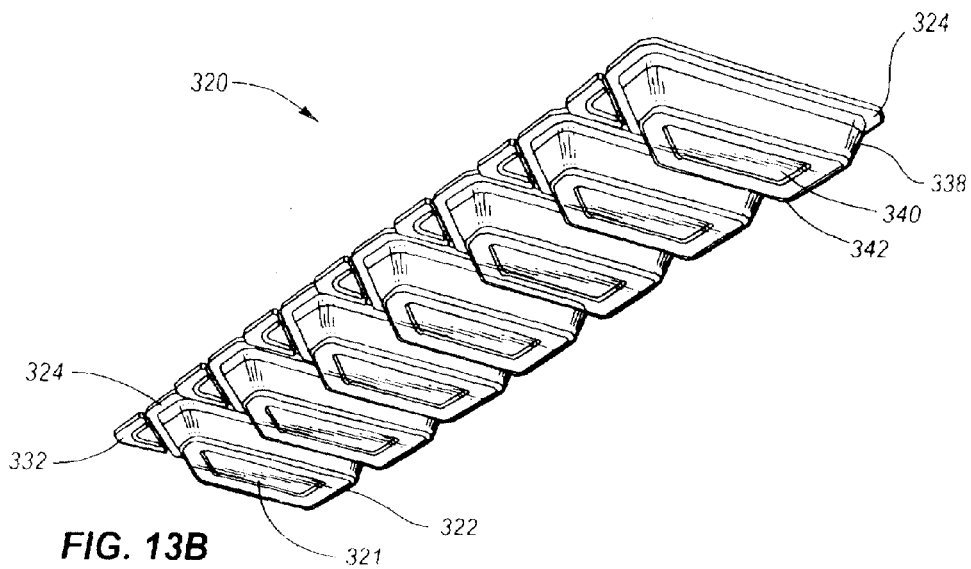

Referring to FIG. 13A and FIG. 13B there is shown a top view and a bottom view of a plurality of illustrative sealed multiple prescription containers 320. Note, the sealed multiple prescription containers may also be referred to as a "primary package." In FIG. 13A and FIG. 13B, both views reflect that one of the containers 321 comprises a tapered body container 322 with a cavity for holding a plurality of tablets. The tapered body container 322 allows a plurality of individual containers to be stacked for storage. Each container 320 has a flanged top surface 324 configured to be sealed with a lid 326. In certain embodiments, the tablet assembly may require individual containers that vary in depth depending on the amount of tablets needed to be dispensed at a specific time. While the depth of the individual containers may vary, the flanged top surface and collar remain constant for processing of different sized individual containers and for commonality with the assembly sleeve.

In one embodiment, the multiple prescription container comprises a plurality of individual containers. In the illustrative embodiment, container 321 adjacent to container 328 and are sealed with lid 326. The lid 326 seals all the containers. The sequential connection between containers provides a linear grouping of the individual containers. However, it should be noted that the quantity of containers in a multiple prescription assembly may vary as well as the interconnection configuration of the containers, e.g. a circular, an elliptical, polyhedral, etc. In this illustrative embodiment, the empty and unsealed containers are made from a single piece of moldable material having indentations 330, which may also be perforations or cuts, that separates container 321 from the other container 328.

At least one of the containers is configured to receive a first tablet associated with a first medication, and a second tablet associated with a second medication that is different from the first medication. The set of containers 334 are separated from one another by frangible connections 336 or perforations positioned within the flanged edge 324 that is proximate to the adjacent container. The frangible connection 336, which is between containers, allows the containers to "break-away" from the set of containers 334 in a sequential manner. Once the lids are attached and/or sealed to the top flanged surface 324, this sequential connection supports a linear configuration for sequential dispensing.

Each container may also comprise a collar 338 below the flanged edge 324 that allows the containers to be stored in a stackable configuration. Each container may also comprise a bottom surface 340 with at least one ridge 342. The ridge is useful in minimizing tablet-to-tablet collisions and avoiding medication sloughing off of a tablet due to collisions with other tablets. By limiting excessive movement of the tablets in each of the containers, the ridge or ridges on the bottom of the container(s) help preserve the integrity of the tablets within. The ridge may protrude outward from the bottom surface of the containers as shown in FIG. 13B, or in other embodiments, may be formed by an indentation of the bottom surface. The ridge(s) may be configured as a square, rectangle, circle, a plurality of parallel lines as well as other geometric shapes.

The illustrative set of containers 334 comprises seven adjacent containers configured for sequential dispensing of the contents of each container. Sequential dispensing refers to individual containers being "dispensed one at a time," which is different from being "cherry picked" from a grid of individual containers. The number of containers in a set of integrated containers may vary due to the prescription prescribed for the user. While the illustrative embodiment describes seven containers, a set of containers may comprise at least two containers to about 20 containers, and more preferably about 5 to about 14 containers. It is expected that most of the containers will be of similar size for ease of filling the containers, but in certain embodiments varying container sizes may be needed. The set of containers 334 may be opaque but in preferred embodiments, the moldable material comprises enough clarity for the user to visualize the contents of the containers.

The illustrative lid 326 of container 321 comprises a printing surface where unique prescription-specific information is displayed for each container. The information displayed on the printing surface may include, but is not be limited to, the patient's name, the date and the day of the week the contained mixed dosage medications are to be taken, as well as the time of day that the tablets are to be taken. The markings on the containers inform the patient and/or caregiver the time in which the contents of the container are to be taken in the proper sequence. In general, the lid stock comes from a roll and the appropriate amount of lidstock is released from the roll to accommodate the designated number of containers to be sealed. For a thermoformed container, using polypropylene for the material for the lid stock, an unsealed area of lid film is generally used to help in the peeling of the lid. The breakaway tab 332 on the illustrative container 321 gives the user something to hold onto and is a useful feature to a container that is manufactured by injection molding with plastics like polyethylene or styrene.

Figure 14:
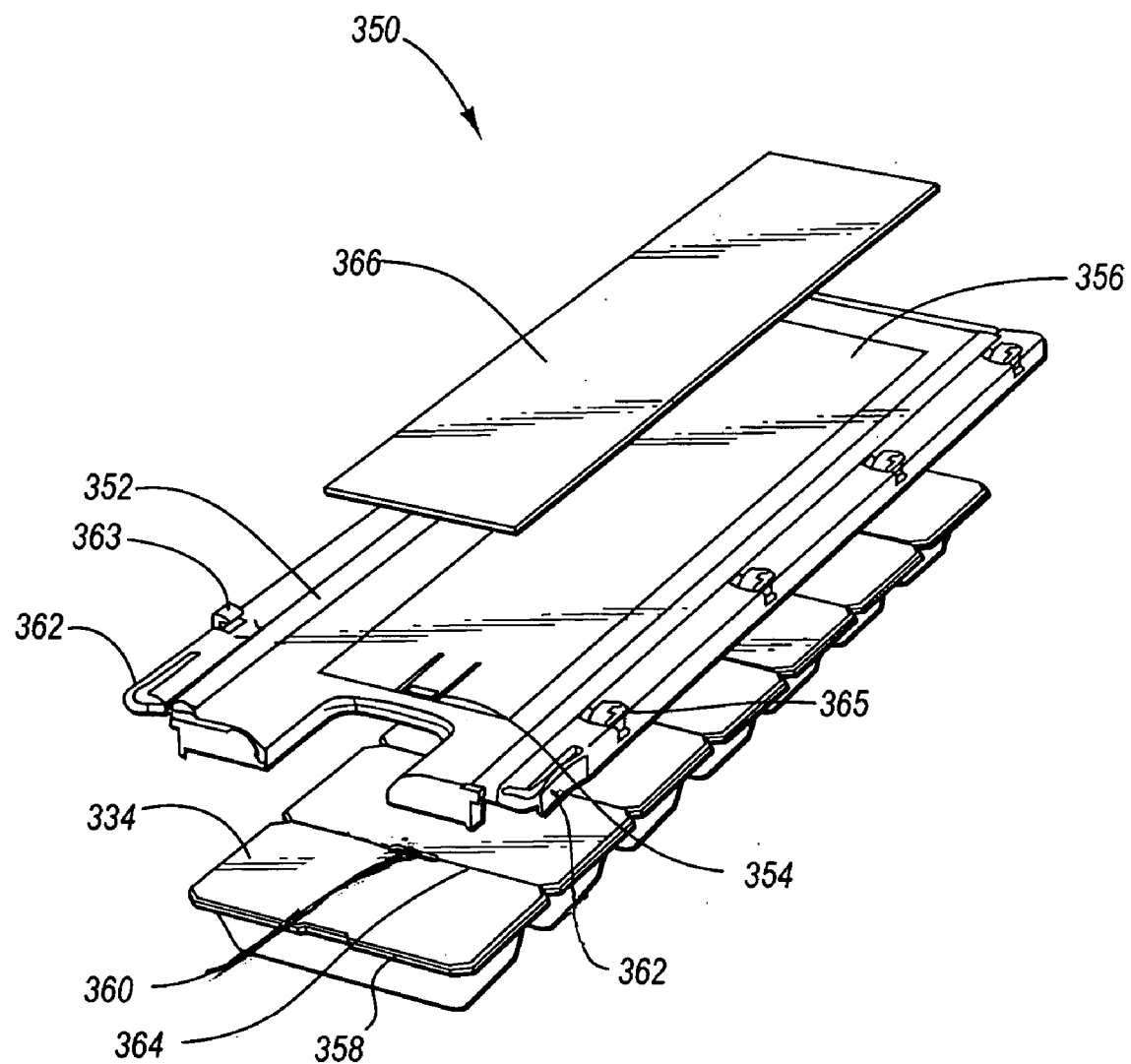
FIG. 14 is an exploded isometric view of the sleeve for the multiple prescription container assembly before it is slidably coupled to the sealed containers.

Referring to FIG. 14 there is shown an exploded isometric view of the multiple prescription container assembly 350 before slidably coupling the set of sealed containers 334 to the dispensing sleeve 352, which is an illustrative secondary package. Recall, the sealed containers are the primary package. The exploded view also shows a top tab 354 on the top surface 356 of the sleeve which holds the end container 358 by catching the rectangular void made by one of the indentations 360. When the user pushes down the sleeve tabs 362, the set of sealed containers are released and the top tab 354 can be disengaged from the containers. The end container 358 can be slid out of the dispensing sleeve 352 if there are no other child protective features, and the top tab 354 latches on to the next indentation (not shown). The user then can break the frangible connection 364 and remove the container. This two-step process of holding tabs 362 and pulling on the end of the sealed containers is a "child safety" feature. It shall be appreciated by those skilled in the art that the child safety feature may be removed to conform to a more senior-friendly solution that is also described herein.

Additionally, there is shown a notch 363 that is configured to be fit into an illustrative cavity that is a square-shaped perimeter 365 and receives a notch similar to notch 363. The notch 363 permits two dispensing sleeves to "snap" together. The square shaped perimeter 365 is located on near the edge of the dispensing sleeve 352 and has a square cut and a lip.

Printed material 366 such as detailed label 160 in FIG. 5, may be attached to the top surface 356 of the dispensing sleeve 352. Additional information about the prescription or other patient data can also be placed on the dispensing sleeve 352. The dispensing sleeve 352 may also comprise a surface for printable indicia on the top surface 356, and the printable indicia may include patient data as well as prescription information.

Figure 15:
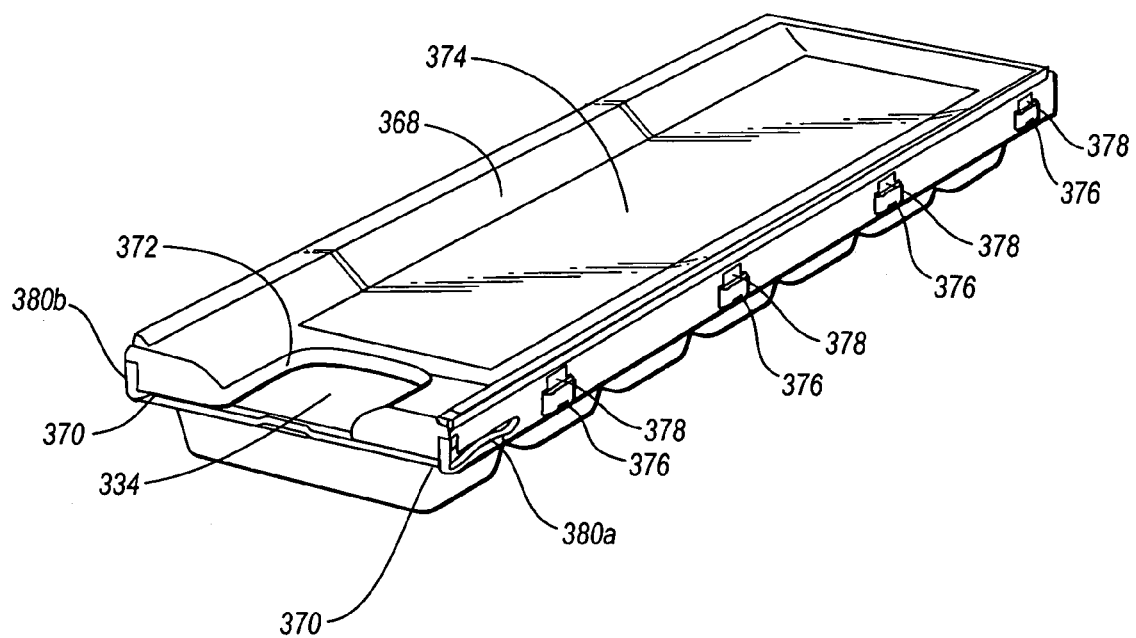
FIG. 15 is an isometric view of the sealed containers slidably coupled to the sleeve for sequential dispensing.

Referring to FIG. 15 there is shown an isometric view of the set of sealed containers slidably coupled to another sleeve for sequential dispensing. In this illustrative embodiment, the sealed multiple prescription containers are operatively coupled to the dispensing sleeve 368. The dispensing sleeve 368 is similar to the dispensing sleeve 352 in that both sleeves comprise grooves or slits 370 configured to allow the flanged top surface 324 in FIG. 13 of each container to slide into the respective dispensing sleeve. Additionally, both sleeves comprise a thumb groove 372, which is configured for a human thumb or finger, allowing a patient or caregiver easy access to the sealed prescription container. The thumb groove 372 also acts as a display window to allow the patient to view the printed markings on the lid of each containers. The dispensing sleeve 368 also contains a printable area 374 large enough to accommodate a detailed label with information about each tablet in each of the containers such as the detailed label in FIG. 5. The dispensing sleeve 368 and 352 may be produced as one piece and is configured to lock onto another sleeve with a "snap and lock" means comprising at least one protruding section 376 that defines a cavity 378 of the dispensing sleeve. The protruding section is configured to receive a notch (not shown) that can interface directly with the protruding section 376. The dispensing sleeve may be injection molded or manufactured from plastics such as polypropylene and ABS.

Additionally, the particular sleeve 368 further comprises integral, mold-in release tabs 380a and 380b configured to allow the sealed containers to slide out of the dispensing sleeve 368 when pressure is applied to release tabs 380a and 380b. The container 350 is then removed by breaking the perforation mark between the containers. The release tabs are configured to "catch" the next container 350 so that one container is released at a time, thereby providing child resistance.

Figure 16:
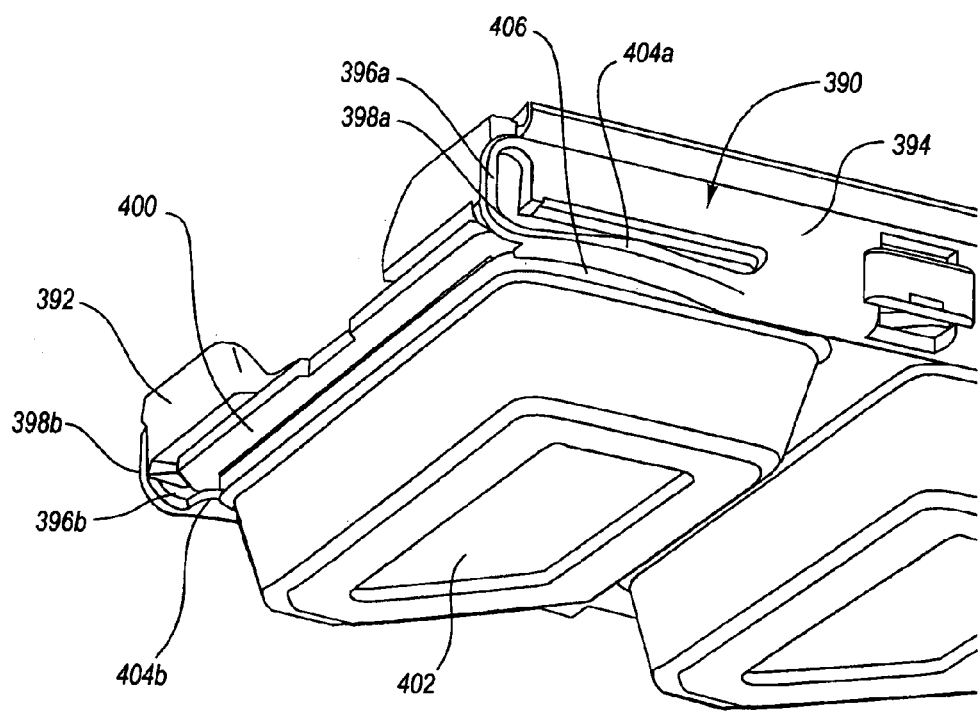
FIG. 16 is an exploded view of an illustrative child protective feature for a multiple prescription container assembly.

Referring to FIG. 16 there is shown an exploded view of an illustrative child protective feature 390 for a multiple prescription container assembly. The first end 392 of the dispensing sleeve 394 comprises release tabs 396a and 396b configured on the sides of the sleeve. The release tabs 396a and 396b each comprise a molded loop 398a and 398b configured to hold the top flanged surface 400 of the end container 402 in the dispensing sleeve 394. The molded loops 398a and 398b have concave sections 404a and 404b which contact the bottom side of the top flanged surface 406. When the end container 402 is to be taken out of the dispensing sleeve, the downward pressure of the user's thumb on the lid of container 402 in the thumb well pushes the concave section 404a and 404b downward, releasing the top flanged surface from the release tabs 396a and 396b, allowing container 402 to exit the dispensing sleeve 394. Other embodiments of the release tab(s) will readily suggest themselves to those of ordinary skill in the art.

Figure 17:
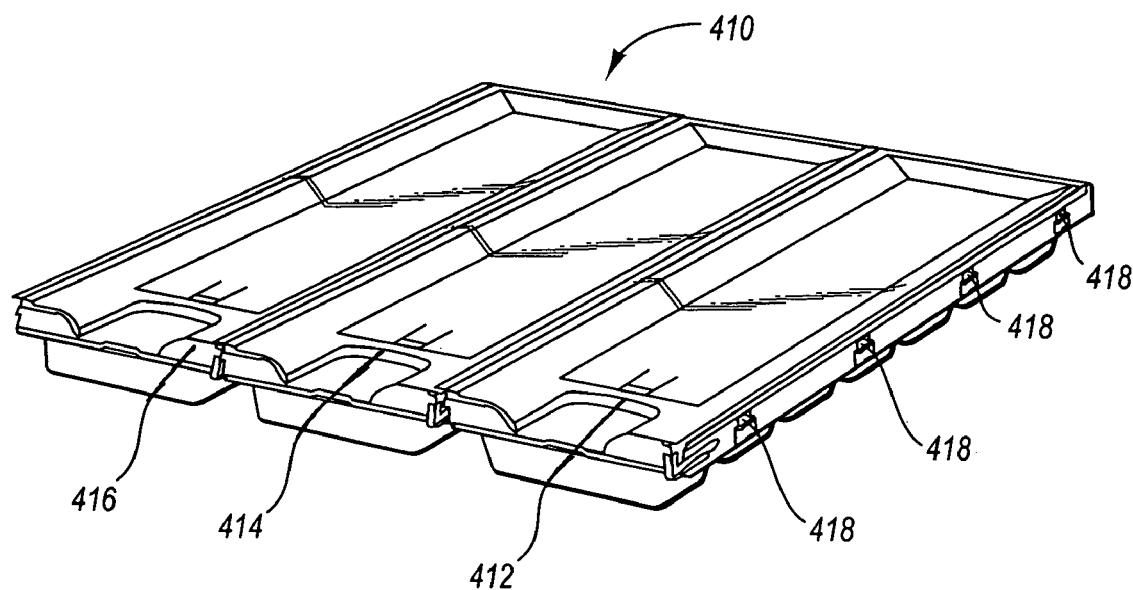
FIG. 17 is an illustrative embodiment of a plurality of dispensing sleeves that are connected to one another.

Referring to FIG. 17 there is shown an illustrative embodiment of a plurality of dispensing sleeves 410 that are configured to interface with at least one other sleeve having a plurality of sealed containers. The dispensing sleeves 410 are similar to dispensing sleeve 368 described above. The first dispensing sleeve 412 is releasably coupled to dispensing sleeve 414, which in turn is releasably coupled to dispensing sleeve 416. Each sleeve comprises a plurality of knobs or hooks on a first side of each sleeve and a plurality of corresponding shaped grooves or knob receptacles 418 on the second side of each sleeve, which enables the sleeves to interlock. In this embodiment, each dispensing sleeves 412, 414, and 416 are grouped together for daily usage on a per week basis for a patient that needs to take medications three times per day, in which the first sleeve 412 is for a prescribed morning dosing, the second sleeve 414 is for a prescribed afternoon dosing, and the third sleeve is for a prescribed evening dosing.

Figure 18:
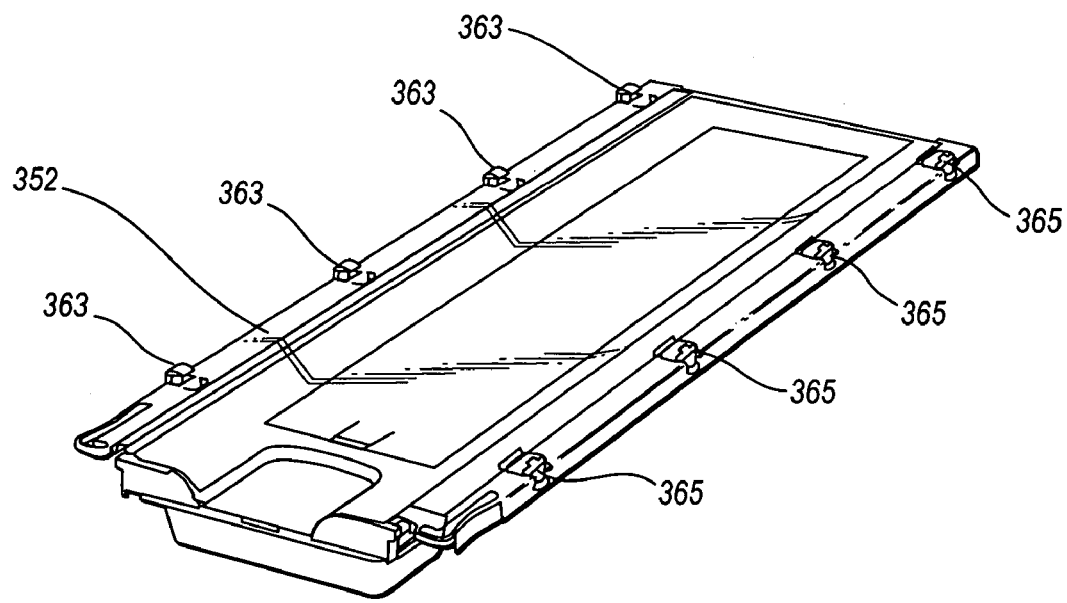
FIG. 18 shows illustrative notches of interlocking elements for an illustrative dispensing sleeve.

Referring to FIG. 18 there is shown illustrative notches of interlocking elements for the illustrative dispensing sleeve 352 shown in FIG. 14. The illustrative notches 363 are configured to be fit into a plurality of square-shaped perimeters 365 that define a cavity. The notches 363 and square shaped perimeters permit two dispensing sleeves 352 to fit together. The square shaped perimeters 365 define a cavity that is located adjacent to the edge of the dispensing sleeve 352. Additionally a small lip is shown that permits the notch to be locked into place.

Figure 19:
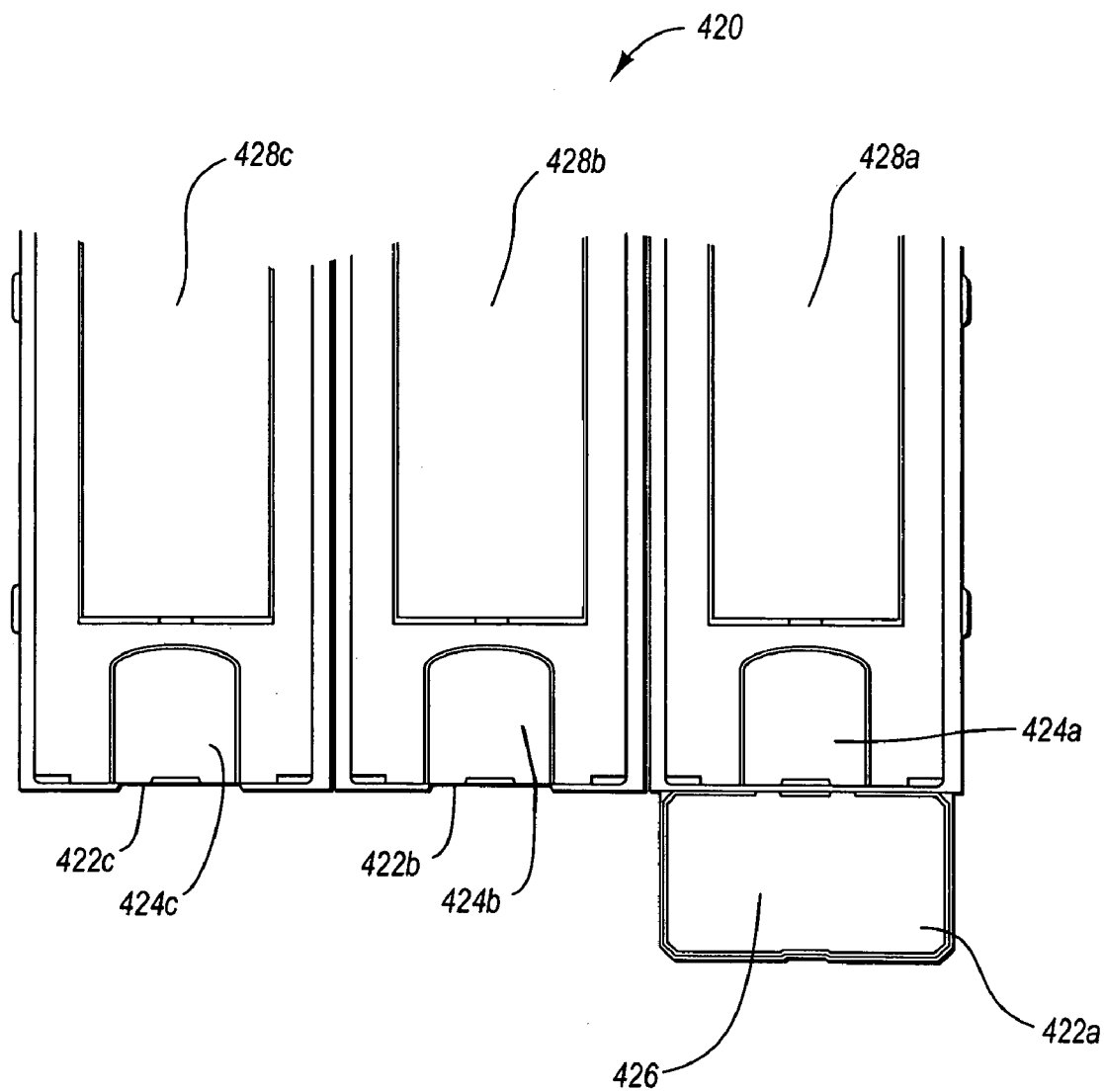
FIG. 19 is an illustrative top view of multiple sleeves coupled to one another and depicting the sequential dispensing of a container.

Referring to FIG. 19 there is shown an illustrative top view of multiple sleeves coupled to one another and depicting the sequential dispensing of a container. In this illustrative example, the multiple prescription container assembly is for patients that must take multiple medications more than once a day. The multiple prescription container assembly 420 comprises a plurality of thermoformed or molded sets of sealed container 422a, 422b, and 422c that are heat sealed with a laminated lid 424a, 424b, and 424c, respectively. Each container within the set of containers 422a, 422b, and 422c contains the required medications that have been prescribed for a particular time. The containers are separated by perforations as described above. In the illustrative embodiment, each container contains printed markings 426 that identify the medications contained therein, and may also indicate the patient's name, and, most importantly for the purposes of this embodiment, the day and the time of day that the medications are to be taken.

In the illustrative embodiment of FIG. 19, each container is dedicated solely to a particular time of day. In the illustrative example, the set of containers 422a are taken in the morning, the set of containers 422b are taken at approximately noon, and the set of containers 422c are taken in the evening. Thus, it is possible to have a plurality of containers for each day of the week so that each container has the proper dosage that is to be taken at a particular time of day. In this illustrative embodiment, the patient is supplied with a complete set of containers for a particular week and for a specific time of day.

Each individual container within each set of containers is to be taken at the correct, prescheduled time each day as marked 426 on each container. The multiple prescription container assembly 420 may be provided to the patient or caregiver as three separate sets of containers enclosed in three separate dispensing sleeves. The patient or caregiver can interlock the three separate dispensing sleeves 428a, 428b, and 428c.

Figure 20A:
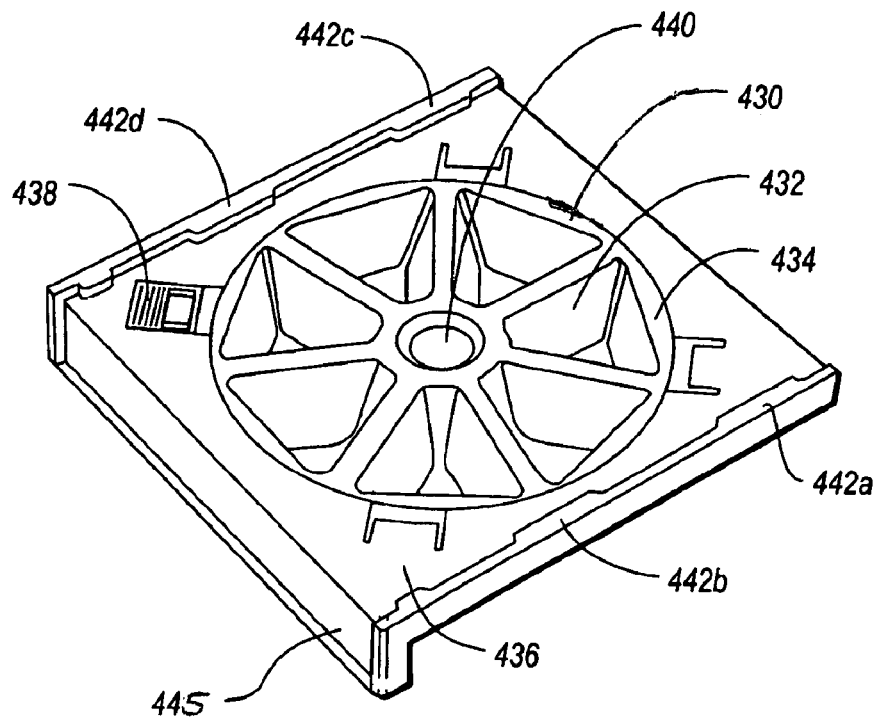
FIG. 20A shows a top view of a second illustrative embodiment of a multiple prescription container assembly.

Referring to FIG. 20A there is shown a top view of a second illustrative multiple prescription container. The illustrative rounded multiple prescription container 430 comprises a plurality of containers 432 that are adjacent to one another. Each container is wedge shaped so that the triangular surface area at the top of each container is greater than the triangular well at the bottom of each container. The illustrative container 432 is surrounded by a flanged edge 434. The dispensing sleeve 436 surrounds the rounded multiple prescription container 430. A release tab 438 on the sleeve 436 permits the rounded multiple prescription container 430 to be rotated within the sleeve 436. The axis of rotation is defined by the well 440 at the center of the plurality of containers. A plurality of ridges 442a, 442b, 442c, and 442d on the sleeve 436 hold cover, lidstock, or any other labels in place.

Figure 20B:
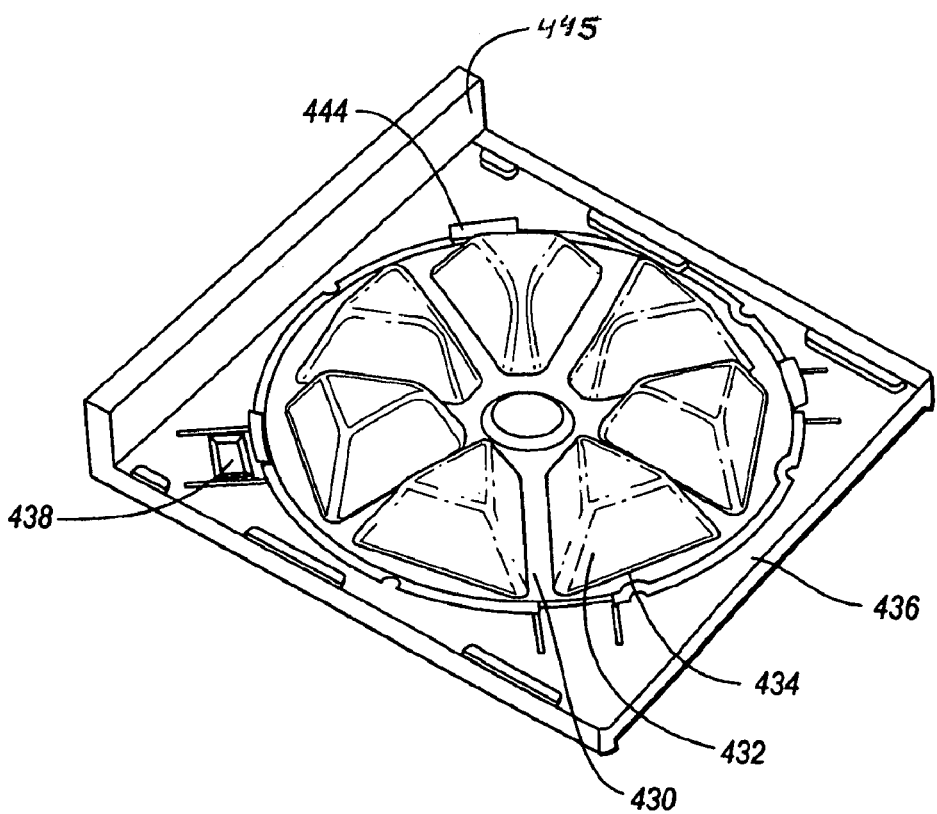
FIG. 20B is a bottom view of the dispensing sleeve housing the rounded containers described in FIG. 20A.

Referring to FIG. 20B there is shown a bottom view of the dispensing sleeve housing the rounded containers described in FIG. 20A. The bottom view shows the rounded multiple prescription containers 430 and the illustrative container 432 with the flanged ends 434 that interface with the sleeve 436. The flanged ends 434 are slidably coupled to the sleeve 436 via a plurality of lips such as lip 444. The bottom view also shows the release tab 438 that permits the rounded containers to rotate around the sleeve. Additionally, a rim 445 is shown that is the approximate depth of the container. The rim 445 receives printed information about the particular patient taking the prescribed medication. The rim 445 also permits the stacking of a plurality of rounded multiple prescription assemblies.

Figure 21A:
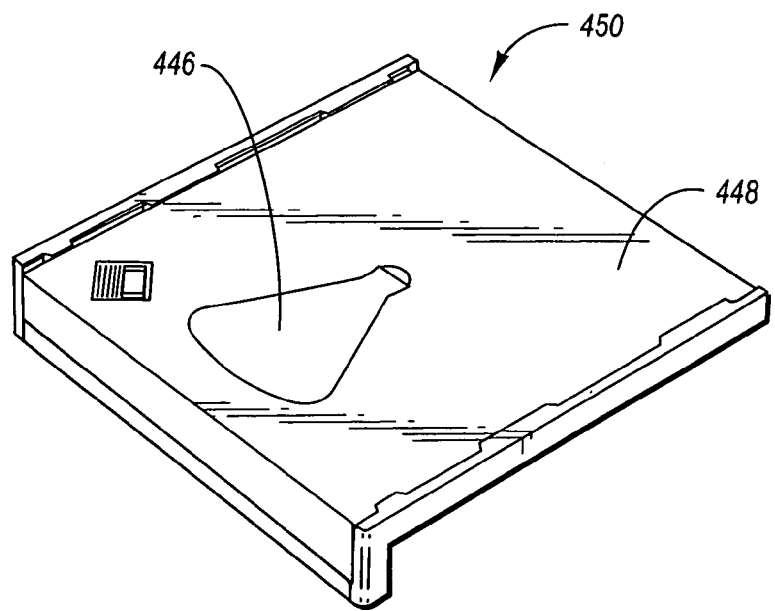
FIG. 21A and FIG. 21B show the dispensing sleeve housing the rounded containers having a first lid and a cover.
Figure 21B:
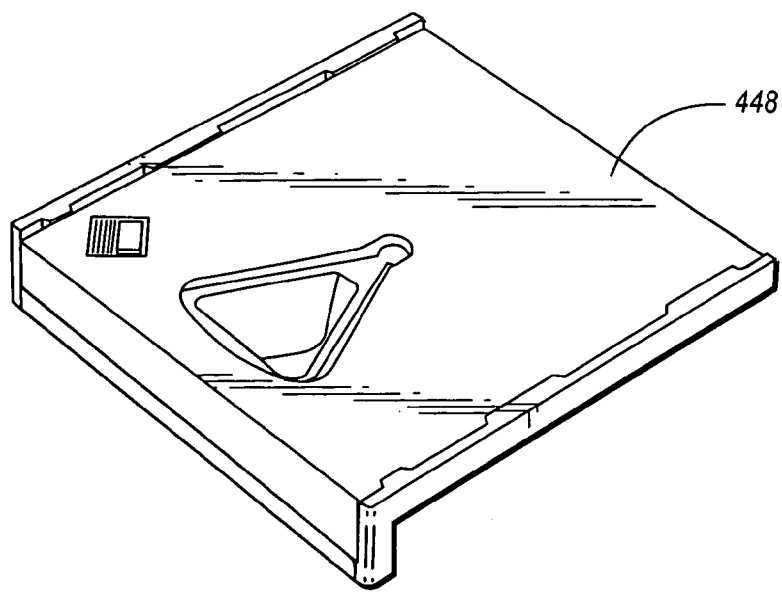

Referring to FIG. 21A there is shown the dispensing sleeve housing the rounded containers having a first lid and a cover. The first lid 446 is visible and is associated with a particular multiple prescription container and is adhesively coupled to the flanged edges of the container. The cover 448 shields the lids and containers within each sleeve. The combination of elements shown in FIG. 21A illustrates a rounded multiple prescription assembly 450. In FIG. 21 B, the first lid 446 is removed, permitting access to the different medications within the container. There may be a variety of printed information on the lid 446 and/or the cover 448.

Figure 22:
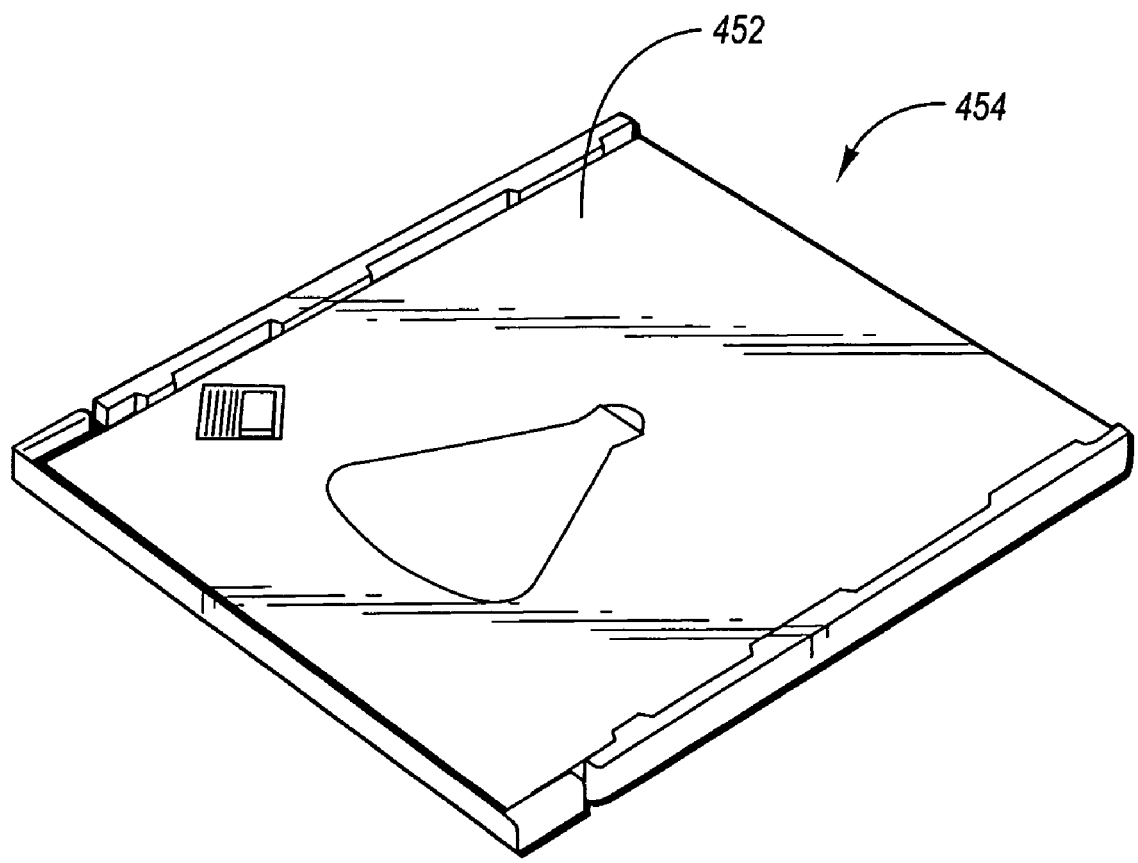
FIG. 22 shows an alternative sleeve that does not include a rim.

Referring to FIG. 22, there is shown an alternative sleeve 452 that does not comprise a rim 445. The sleeve 452 is configured to receive the rounded multiple prescription container 430, and the combination results in an alternative embodiment of the rounded multiple prescription container assembly 454.

Both of the multiple prescription container assemblies 450 and 454 are configured for sequential dispensing. While the illustrative embodiment describes seven containers, a set of containers may comprise at least two containers to about 20 containers, and more preferably about 5 to about 14 containers. It is expected that most of the containers will be of similar size for ease of filling the containers. Additionally, the illustrative moldable material comprises enough clarity for the user to visualize the contents of the containers.

Figure 23A:
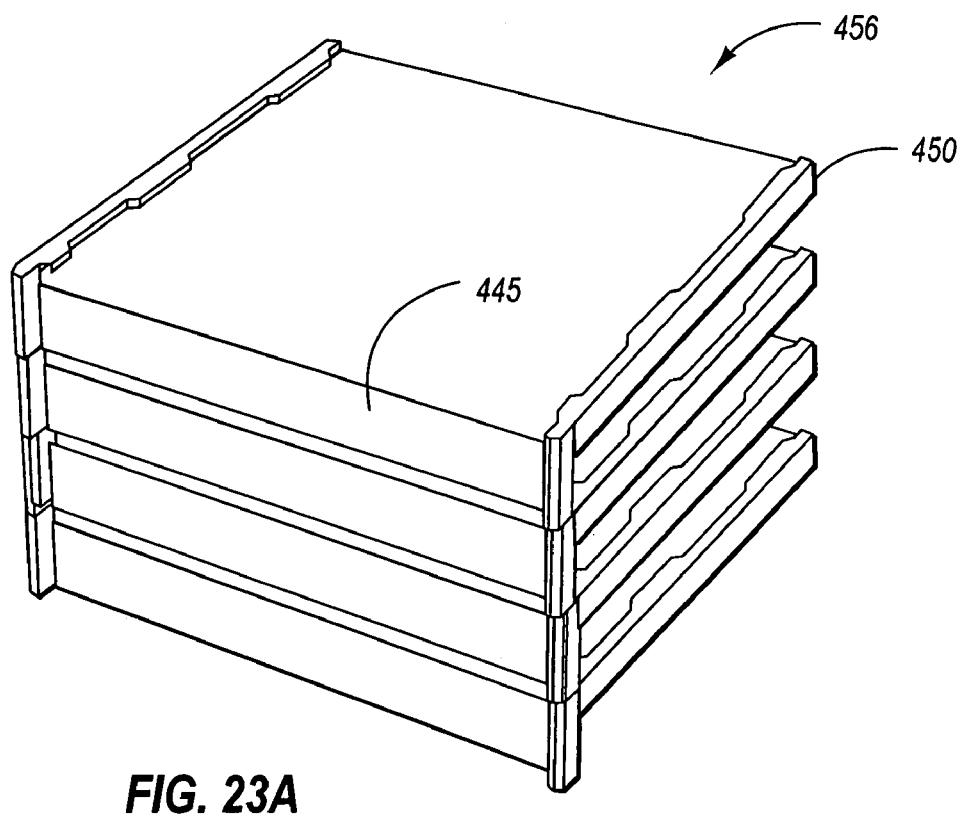
FIGS. 23A and 23B show two separate perspective views of a plurality of stacked rounded multiple prescription container assemblies.
Figure 23B:
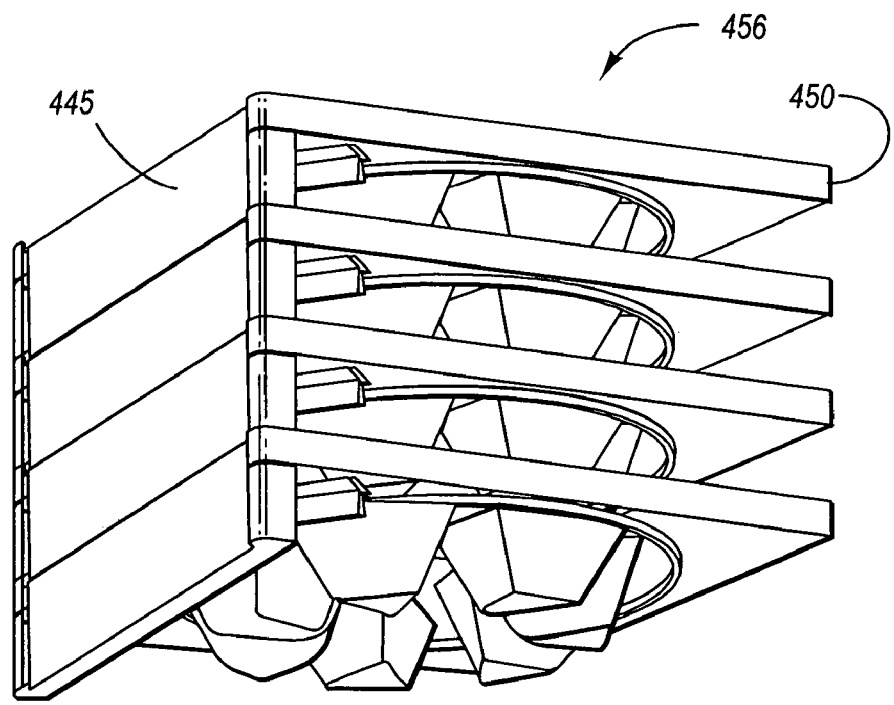

Referring to FIGS. 23A and 23B, there are shown two separate perspective views of a plurality of stacked rounded multiple prescription container assemblies. The stacked rounded multiple prescription assemblies 456 are composed of a plurality of rounded multiple prescription container assemblies 450. Each of the multiple prescription container assemblies 450 are stacked on top of one another with the rim 445, which permits the stacking of rounded multiple prescription container assemblies.

Referring to FIG. 24A there is shown a perspective view of a third embodiment of a multiple prescription assembly that is a circular multiple prescription container assembly. In this illustrative embodiment, the circular multiple prescription container assembly 460 comprises a set of multiple prescription containers 462 having flanged edges similar to the flanged ends 434 (described in FIG. 20A), a lid 464, and a cap 466. The lid 464 seals the multiple prescription containers 462. The cap 466 fits over the flanged ends (not shown) and has a triangular opening 468 cut into the cap 466. The cap 466 is configured to snap fit with the sealed multiple prescription containers. The triangular opening 468 permits the patient and/or caregiver to view writing on the lid 464 and to have access to the lid 464. Referring to FIG. 24B, there is shown an illustrative embodiment in which the lid 470 has printed information that identifies the patient, the date, and the time that the prescribed medications are to be taken.

Additionally, the illustrative lid 464 is cut to permit a patient to remove the lid by placing a finger underneath a cut 472. A ridge 474 permits the lid 464 to be more easily removed from the container. A more detailed view of a patient or caregiver removing the lid 464 is provided in FIG. 25. Once the contents of a particular container have been removed, the cap 466 is rotated, and provides access to the next sealed container.

Referring to FIG. 26 there is shown a flowchart of an illustrative method for dispensing tablets which utilizes a secondary package or sleeve for housing a primary package or a multiple prescription container 500. This illustrative method for dispensing tablets comprises providing a set of integrated containers 502, the containers adjacent to one another and filling each container with at least one tablet previously specified for each container. The method also comprises the set of integrated containers having a flanged edge and at least one frangible connection, e.g. perforated line, configured within the flanged edge between each of the plurality of containers 504. The method may also comprise providing a lidstock with a plurality of lids that may be adjacent to one another in a linear arrangement 506. The configuration of the lids is not limited to a linear arrangement and may be configured in any manner as to be capable of sealing the set of integrated containers. The method further comprises providing a frangible connection between each of the plurality of lids 508. The frangible connection may be a thinned region of plastic that is easily breakable, perforations in the film and the like.

The method comprises sealing the plurality of containers of the set of integrated containers with the corresponding plurality of lids 510 of the lidstock. The quantity of the containers in the tablet assembly is variable, depending on the prescription of the patient. The number of lids will correspond to the number of containers utilized in the tablet assembly. A printable surface is provided on each of the plurality of lids 512 in which specific printing indicia or information is placed 514 relating to the administration of the tablets held in the container sealed by the corresponding lid.

This method may also comprise providing a sleeve or secondary package for receiving the set of sealed containers 516 and placing the set of sealed containers or primary package into the sleeve 518 or secondary package. The patient completes the process of dispensing the tablets by expelling or manually moving one of the plurality of sealed containers out of the sleeve at the time printed on the corresponding lid 520. Once the container has been slid out from the secondary package, the container is removed from the set of containers as well as the secondary package and/or sleeve by tearing the frangible connection between the expelled container and the adjacent container remaining in the sleeve 522. The patient can then gain access to the tablets in the expelled container by removing the lid from the container 524. In some alternative embodiments, the method comprises providing extended tabs on the lids, break-away tabs and/or providing chamfered edges on the containers to make removing the lid off of the container more convenient.

In yet another embodiment, the method further comprises providing a child safety release tab on a secondary sleeve as seen on the tablet assembly embodiment shown above, to prevent unwanted tampering of the tablets in the containers by children. In the embodiment described above, at the proper time for dispensing the tablets from a container, the patient holds the dispenser and manually actuates the release tabs while simultaneously manually sliding the strip of containers in a direction "out of the dispenser." When the perforations or frangible connection between the first two containers in the strip reach the outer edge of the dispenser the release tab resets, thus locking the strip from further sliding motion. The patient then tears off, at the perforations, the protruding container that contains the correct medications for the stated time, pulls up on the extended corner of the lid, and opens the container by peeling back the lid, exposing the medications. The dispenser then is left with the correct printed markings showing in the thumb groove display window, ready for the next dosage to be taken. Other embodiments of the methods of dispensing tablets comprise providing a "senior friendly" tablet assembly instead of an assembly with a child safety tab for the convenience of patients with limited dexterity shall be readily identified by those of ordinary skill in the art.

Referring to FIG. 27 there is shown a flowchart of the production facility processes 600 used by an illustrative production facility to fill a prescription order. After receiving the prescription order in one of the illustrative system and/or methods described above, the order processing system 602 begins controlling the filling of the prescription order. By way of example and not of limitation, the ordering processing system 602 interfaces with an online server, production server, or both, and receives data that relates to the type of medication or tablet, and the type of multiple prescription container assembly that needs to be filled with the appropriate medications and/or tablets. Those with ordinary skill in the art of manufacturing processes and robotic processes shall appreciate that the systems or methods for controlling production can be performed using a centralized control system or a distributed control system. For purposes of this patent, those with ordinary skill in the art shall appreciate that there will even be instances where a combination of centralized and distributed control are optimal, and depend on design requirements and design expectations.

The order processing system 602 is in communication with a tablet management system 608. The tablet management system 608 controls the tablets that fill the pill refill modules, which in turn fill up the appropriate multiple prescription containers. The tablet management system 608 also communicates when a refill module is not properly being filled. The order processing system 602 also communicates with a container selection process 604. The container selection process 604 may receive an order for a particular container assembly from the user placing the order, e.g. pharmacist, caregiver, patient, etc. Alternatively, the container selection process 604 may simply receive a multiple prescription order, and may have to select the appropriate container for filling the order, e.g. less than 5 tablets require a small container, 6-10 tablets require a mid-size container, and 10-20 tablets require a large container.

After the container selection process 604, there is a container inspection process 606 during which inspection of the appropriate container is performed, to ensure that the appropriate container or substitute container has been selected. Additionally, the inspection process 606 may include identifying whether the container is broken or has some obstruction that may cause some difficulty to downstream systems and/or processes.

After the container inspection 606, the container filling process 610 is initiated. In an illustrative example, the container filling process 610 occurs by placing the selected container on a pallet or tote and moving the pallet or tote on a conveyer, which moves the pallet to the appropriate filling location so that the appropriate tablets may fill the container.

After filling the appropriate container with a plurality of medications and/or tablets, an inspection of the filled containers is performed at block 612. The inspection may be conducted by using X-ray detection, near infrared detection, robotic detection at visual wavelengths, or any other such technique that looks at color, shape, weight, density, or other such parameter to determine if the appropriate container has been filled with the correct prescription. In certain instances, a visual inspection by a pharmacist may also be performed.

After inspection, the method proceeds to the lid assembly process 614 during which the lid is applied to the multiple prescription container producing the primary package. The sleeve is then applied at the sleeve assembly process in block 616. Alternatively, a cap may be placed on the sealed multiple prescription container, as described above. For purposes of this patent, the term "sleeved container" or secondary package includes a multiple prescription container having a cap, unless otherwise indicated.

At block 618, the inspection of the sleeved sealed containers is conducted. This inspection at block 618 is performed after the multiple prescription container has been sealed. Note, the inspection at block 612 was conducted before sealing. The need for the second inspection described in block 618 is in case a tablet or medication fell out of the container or was mislabeled. Additionally, one of the tablets or medications may also have been broken or otherwise compromised. As stated above, the inspection may be conducted using a variety of different instruments including, but not limited to, robotic inspections at a visual wavelength, near IR, X-ray and any other detection means that can identify the type of tablets or medication in each container.

The method then proceeds to block 620 where the sleeved sealed container(s) are combined with printed materials in the tote. The printed materials may include detailed labels as described in FIG. 5-7 above. Additional materials may also be provided such as printed materials from pharmaceutical companies, medical providers, pharmacists, and other such entities. The printed materials are controlled by the tote assembly system 622. The printed materials may be generated at the production facility by a detailed labeling component or may be shipped to the production facility or any combination thereof.

After combining the printed materials and the sleeved sealed multiple prescription containers at a distribution element, the combination is shipped to a pharmacy, customer, or sent to a pick-up window as represented by block 624. As stated above, the customer may be a patient, a caregiver, a medical health professional, or any other such person Referring to FIG. 28, there is shown an illustrative large-scale production facility 628 that may occupy a warehouse. A plurality of container 630 are fed in a container feeding section by an operator 632 that places the containers on a pallet or tote that are carried by a conveyor belt 634 around the facility. The operator 632 is charged with container selection based on the information provided by the order processing system. Additionally, the operator 632 is charged with performing a visual inspection of the containers that are placed on the pallet or tote.

The powered conveyor then transports the tote having the empty containers to filler cells that have a particular medication or tablet. As the empty container passes under each filler cell 635, the tablet management system determines whether a tablet is to be dispensed. The container filling process requires a variety of different filling cells that have to be refilled by illustrative operators 636 and 638. The conveyor belts and filler cells are grouped into units for easier operation and maintenance. In the illustrative embodiment, the powered conveyers can travel to the appropriate filler cell in an efficient manner that permits a particular pallet to bypass traveling along the perimeter of the conveyor assembly. For example, a particular pallet may bypass traveling along the length of a conveyor via a bypass 640 or 642.

The filled containers are then inspected to determine if the container has been properly filled. An operator 644 mans the inspection equipment. If order adjustments are needed, another operator 646 is charged with resolving any problems with one or more orders. The operator 644 determines that the prescription has been properly filled after having visually inspected the multiple prescription or using other inspection means are described herein. The appropriate lid is then placed on the containers. A lidstock sealer 648 seals the lid on the multiple prescription container. The sleeve is then selected at the sleeve assembly 650 and then applied. The operator 652 inspects the sleeve. Additionally, the operator 652 may be charged with combining the sleeved and sealed prescription container. A separate tote filling system 654 or detailed labeling component generates the detailed label that is combined with the sleeved and sealed multiple prescription containers. The conveyor 656 then transports the filled prescription order to a predetermined location so that the filled prescription order may be shipped to the pharmacy or customer.

Referring to FIG. 29 there is shown a perspective view of a small-scale illustrative tabletop system that can be used to have a local pharmacist to fill the multiple prescription order. Although the warehouse size production facility is described above in FIG. 28, the tabletop system is much smaller and can also be used to fill a multiple prescription order. The illustrative table top system 660 receives a prescription order at station 662. The appropriate containers 664 are selected and placed on a conveyor (not shown) that are fed under fill cells 666. At workstation 668 the multiple prescription order is inspected by the pharmacist. A lid is generated at station 670 and sealed at station 672. The sleeve located at sleeve dispenser 674 is then applied. The sealed sleeve assembly is then inspected by the pharmacist. The detailed label is generated by printer 676, and all the printed materials are combined with the sealed and sleeved multiple prescription container. The filled multiple prescription may then be picked up at a "pick-up" window 678. A pharmacist at station can then explain to the customer about the multiple prescription packaging.

Referring to FIG. 30 there is shown a block diagram of an illustrative order processing system 602. The order processing system 602 is configured to control the filling of the prescription order. The order processing system comprises a block 690 in which a multiple prescription order is received. The multiple prescription order may be received electronically or at a pharmacist's window. The system 602 then proceeds to check an inventory management system 692 and determines if the appropriate medication or tablets are available. At decision diamond 694, a decision to order additional inventory is made if the inventory of tablets or medication are running low. If inventories are running low, then at block 696 an order is placed for additional tablet inventory. However, if there is a satisfactory inventory, block 698 communicates tablet type, size, quantity, frequency, packaging, and time for taking the prescribed medications in the container selection process 604 and the pill management system 608.

The order processing system 602 also accommodates receiving the tablet received in block 700, after having placed the order for additional inventory in block 696. After receiving the ordered tablets, the inventory management system is updated as indicated in block 702. The updated inventory is then communicated to the pill management system 608. The order processing system 602 is intended to make it more efficient for a production facility and/or pharmacist to manage the tablet or medication inventory stored at the local facility. By creating a system and method for automated ordering, the order processing system can provide a more efficient means for controlling inventory and thereby more efficiently control the filling of multiple prescription orders in multiple prescription containers.

Referring to FIG. 31 there is shown a flowchart of an illustrative container selection process 604. The container selection process 604 may receive an order for a particular container assembly from the user placing the order, e.g. pharmacist, caregiver, patient, etc. Alternatively, the container selection process 604 may simply receive a multiple prescription order, and may have to select the appropriate container for filling the order, e.g. less than 5 tablets require a small container, 6-10 tablets require a mid-size container, and 10-20 tablets require a large container. For either embodiment, the container selection process 604 is initiated by receiving the appropriate tablet and/or container information. For example in block 704, tablet data and/or container selection data is received that may comprise type of tablet or medication, size of the tablet or medication and the frequency with which the tablet or medication needs to be consumed.

At block 706, the method may determine the type of container to use based on the types of medications, size, and frequency. The determination of the type of container may be performed without receiving a user's request for a particular multiple prescription container assembly as described above. The determination of container availability is then made at decision diamond 708. If a particular container is not available, the method may return to block 706 to select an alternative container. Issues associated with container availability are reported to the inventory management system 702. If the containers are available, the method proceeds to block 710 where the containers are de-nested and then placed on the appropriate pallet, at block 712. The method then proceeds to container inspection at block 606.

Referring to FIG. 32, there is shown an illustrative block diagram of an illustrative tablet management system 608. The illustrative tablet management system 608 controls the tablets that fill the pill refill modules described above. The tablet management system 608 also communicates when a refill module is not properly being filled. Bulk tablets are received at block 720 and then are fed into an illustrative hopper 722. The tablets are then separated by a separator 724 and are then inspected 726 to determine if they have been placed in the appropriate refill module.

A tablet refill control system 728 manages the tablet being distributed to the appropriate refill module 730. Additionally, the tablet refill control system receives tablet information 732, and this tablet information is stored on the tablet refill control system 728. The additional tablet inventory and is then communicated to the inventory management system 702.

Referring to FIG. 33 there is shown an illustrative refill module 730. The illustrative refill module includes a hopper 734, separator 736, and sensor 738 that counts the tablets. The tablet refill control system 728 communicates with the illustrative refill module 730. A plurality of feeding tubes 740 distributes one or more tablets to the illustrative containers 742. Broken tablets are collected in bottle 744 after being inspected by sensor 738.

Referring to FIG. 34 there is shown a flowchart of an illustrative multiple prescription container filling process 610. Recall, the container filling process 610 occurs by placing the selected container on a pallet or tote and moving the pallet or tote on a conveyer that moves the tote or pallet to the appropriate filling location so that the appropriate tablets may fill the container. In the illustrative production facility described in FIG. 28 or the illustrative bench system in FIG. 29, an operational conveyor system is used to transport the containers. Thus, in the illustrative examples an operation conveyer system 750 is required. However, those skilled in the art shall appreciate that a conveyer system may not be required and may instead rely on being gravity fed and placed into a particular container configured to hold a plurality of medications or tablets.

The illustrative conveyer system receives a container pallet or tote at block 752. The containers then stop at the appropriate refill module and are filled with tablets as described in block 754. Additionally, each refill module may comprise a sensor 738 that counts the number of tablets that are distributed by the refill module, and this count may be communicated to the tablet refill control system 728. A container tracking system 756 tracks the location of each container so that the appropriate medications or tablets are filled by the appropriate filling modules. By way of example and not of limitation, the container tracking system 756 and the refill module are communicatively coupled to the tablet refill control system 728. After the containers are filled by the plurality of refill modules, the illustrative unsealed containers are inspected at block 612.

Referring to FIG. 35 there is shown an exploded perspective view of the illustrative tabletop system 660 that comprises order processing, pill management, container selection, container inspection, container filling, lid generation and lid placement. As described above, the illustrative table top system 660 receives a prescription order at station 662. The appropriate containers 664 are selected. By way of example and not of limitation, there are three different size containers, e.g. small, medium, and large. The appropriate containers are selected by the pharmacist and are then placed on a conveyor 665, which feeds these multiple prescription containers to refill cells 666. The refill cells 666 are configured to deposit the appropriate tablets and/or medications into the containers. At workstation 668 the filled multiple prescription order are visually inspected by the pharmacist. Alternatively, there may be other means of inspecting the filled, yet unsealed, multiple prescription containers such as near infrared, X-ray, or such means for inspection. A lid is then generated at station 670.

Referring to FIG. 36 there is shown a flowchart with a more detailed flow of the inspection of filled multiple prescription containers that have not been sealed. After filling the appropriate container with a plurality of medications and/or tablets, an inspection of the filled containers is performed at block 612. The inspection may be conducted by simply providing an image to the pharmacist so that the pharmacist can see if the appropriate tablet or medication is in each container, as represented by block 760. Additionally, precision weighing 762 may be used to make sure that the appropriate tablets or medications are deposited in the appropriate multiple prescription container. The inspection may also be conducted by using X-ray detection 764 or some other form of detecting such as near infrared detection, robotic detection at visual wavelengths, or any other such technique that looks at color, shape, density, or other such parameter to determine if the appropriate container has been filled with the correct prescription. If a determination is made that the multiple prescription container has not been properly filled, then order adjustment 766 may be performed. After inspection, the process continues to lid assembly processing.

Referring to FIG. 37 there is shown a flowchart describing an illustrative lid assembly process 614. After inspection, the method proceeds to the lid assembly process 614 during which the lid is applied to the multiple prescription container. The lid assembly process 614 comprises receiving blank lidstock 770, and placing the lidstock 772 in a position so that lidstock printing 774 can take place. To perform the printing on the lidstock, a printing ink, toner, or ribbon is needed.

In the illustrative production facility 628, a pallet is used to transport the multiple prescription container to the appropriate lid assembly section, as described by block 778. In another embodiment 660, a pallet is not needed and the container simply travels along the conveyer. In yet another embodiment, a conveyer is not needed. However, regardless of the system and method used to transfer the filled multiple prescription container, a label needs to be applied. In this illustrative embodiment, the appropriate label is generated as described above and placed on the filled multiple prescription container as represented by block 780. The method then proceeds to block 782 where the lidstock is heat sealed to the filled multiple prescription container. The sleeve is then applied at the sleeve assembly process 616.

Referring to FIG. 38 there is shown a flowchart of an illustrative sleeve assembly process 616 where the sleeve is applied to the sealed multiple prescription container. By way of example and not of limitation, the sealed multiple prescription container is communicated using a pallet, as represented by block 790. The sleeve is then combined with the sealed multiple prescription container at block 792.

The illustrative sleeve is generated by receiving a blank sleeve 794 and placing the sleeve 796 in the appropriate position so that a printed label 798 can be placed on the sleeve. The printed label 798 may be generated locally with printing ink, toner, or a ribbon 802. The complete sleeve assembly 804 is then ready to be coupled to the sealed multiple prescription container. As described above, a cap may also be placed on the sealed multiple prescription container, instead of a sleeve.

Refer to FIG. 39 there is shown a more detailed flowchart of the inspection of the sleeved containers conducted at block 618. This inspection at block 618 is performed after the multiple prescription container has been sealed. The need for this second inspection is to maintain a high degree of quality assurance and quality control (QA/QC). For example, a tablet or medication may have fallen out of the multiple prescription container during the lid sealing process described above. Additionally, the wrong printed information may have been placed on the lidstock, sleeve, or cap. In the illustrative production facility embodiment, the sleeved sealed containers are received in block 806. At block 808, the printed information on the sleeve and/or lid is verified. If the label is incorrect then the label is rejected at decision diamond 810, and a new label is placed on the sleeve 812. If the label is accurate, then the method proceeds to block 620 where tote printed materials are combined with the sleeved multiple prescription containers.

Note, that other problems that may also be identified during the inspection process 618 include identifying tablets or medication being broken, compromised, or too many tablets being dispensed at one particular time. Additionally, the inspection may not be limited to simply checking the label, and a more exhaustive secondary inspection may be conducted using a variety of different instruments including, but not limited to, robotic inspections at a visual wavelength, near IR, X-ray, precision weighing and any other detection means that can identify the type of tablets or medication in each container.

Referring to FIG. 40 there is shown an exploded perspective view of the illustrative tabletop system with the lid assembly process, sleeve assembly process, and inspection. The illustrative table top system includes generating a lid at station 670, and sealing the lid at station 672. The container travels along conveyor 665. The sleeve located at sleeve dispenser 674 is then applied. The sleeve label is generated at sleeve label station 675. The pharmacist then proceeds to combine the sleeve and the sealed multiple prescription container. The pharmacist then may perform a visual inspection. Printed materials are generated by printer 676, and the printed materials are combined with the multiple prescription container assembly.

Referring to FIG. 41 there is shown a block diagram of the tote assembly system 622 that controls the printed materials. Prior to generating the printed materials the illustrative tote assembly system performs an order consolidation process 820. The order consolidation process comprises accessing a database with patient prescriptions and orders and consolidating various prescriptions or orders. For example, a patient may request vitamin supplements with prescribed medications, and so order consolidation may be necessary. Additionally, there may be two separate prescriptions from two different doctors that need to be combined. The method then proceeds to block 822 where the patient-specific information is printed. This patient-specific information may include the detailed labels described above in FIG. 5-7 above. At block 824, prescription literature that is provided by a pharmaceutical company, medical provider, insurance company, or other such health professional may be included. These printed materials may be generated at the production facility or may be shipped to the production facility or any combination thereof. In the illustrative tote assembly system, shipper packaging information may also be processed at block 826, so that the illustrative production facility may accommodate shipping using a variety of different carriers, e.g. FedEx, UPS, USPS, DHL, etc. The appropriate shipping label is then generated at block 828. The method then proceeds to block 620 where the sleeved sealed container(s) are combined with printed materials in the tote or pallet.

Referring to FIG. 42 there is shown a block diagram describing the combining of the tote and sealed multiple prescription containers at block 620. At block 830, the illustrative production facility conveys the pallet or tote with the multiple prescription container assembly. At block 832, the multiple prescription container assembly is then combined with the printed materials generated by the tote assembly system 622 including the detailed label. After the prescription order is filled, a record of the filled prescription is recorded and communicated to the appropriate entities as represented by block 834. The multiple prescription container assembly and associated materials are combined and then distributed or shipped to the pharmacy or customer as reflected by block 624.

It is to be understood that the foregoing is a detailed description of illustrative embodiments. The scope of the claims is not limited to these specific embodiments. Various elements, details, execution of any methods, and uses can differ from those just described, or be expanded on or implemented using technologies not yet commercially viable, and yet still be within the inventive scope of the present disclosure. The scope of the invention is determined by the following claims and their legal equivalents.

What is claimed is:

1. A production facility configured to fill a multiple prescription order having different medications, the production facility comprising:
    a means for processing a multiple prescription order that is associated with a particular patient, the multiple prescription order comprising at least two different tablets that are consumed at prescribed intervals determined by a prescription;
    a set of containers that includes a plurality of open multiple prescription containers, in which each of the multiple prescription containers is separated by a frangible connection and the multiple prescription containers include a flange on the top surface of the set of containers, wherein each of the multiple prescription containers being associated with a prescribed time interval determined by the multiple prescription order, and each multiple prescription container configured to receive the different medications that are consumed at the prescribed time interval;
    a sleeve configured to interface with the flange on the top surface of the set of multiple prescription containers, wherein the sleeve includes a sleeve top face that extends over a plurality of multiple prescription containers;
    a first labeling component configured to generate a detailed label that is coupled to the sleeve top face, wherein the detailed label provides a plurality of medical information regarding the different tablets including,
        a drug interaction label component that provides information about various drug interactions associated with each medication,
        a summary medication label component that describes each medication;
    a first inspection component configured to inspect each open multiple prescription container having the different tablets, wherein the open multiple prescription containers are separated by the frangible connection and include the flange on the top surface of the set of containers;
    a second labeling component within the production facility, the second labeling component configured to print on a lidstock a date and a time for the patient to consume the tablets, the second labeling component configured to fixedly couple the lidstock to each multiple prescription container thereby sealing the multiple prescription container after the inspection by the first inspection component; and
    a second inspection component configured to inspect the set of containers and each of the associated sealed multiple prescription containers.

2. The production facility of claim 1 wherein the means for processing the multiple prescription order comprises a computer at the production facility that communicates the multiple prescription order to the first labeling component.

3. The production facility of claim 1 wherein the means for processing the multiple prescription order comprises a computer at the production facility that communicates the multiple prescription order to the first inspection component.

4. The production facility of claim 1 wherein the means for processing the multiple prescription order comprises a computer at the production facility that communicates the multiple prescription order to the second labeling component.

5. The production facility of claim 1 wherein the means for processing the multiple prescription order comprises a computer at the production facility that communicates the multiple prescription order to the second inspection component.

6. The production facility of claim 1 wherein the means for processing the multiple prescription order comprises analyzing the multiple prescription order.

7. The production facility of claim 1 wherein the production facility is configured to operatively communicate with an insurance company server having the particular patient's insurance information.

8. The production facility of claim 1 wherein the detailed label comprises the name of the patient.

9. A method for operating a production facility configured to fill a multiple prescription order having different medications, the method comprising:
    processing a multiple prescription order that is associated with a particular patient, the multiple prescription order comprising at least two different tablets that are consumed at prescribed intervals determined by a prescription;
    retrieving a set of containers that includes a plurality of open multiple prescription containers, in which each of the multiple prescription containers is separated by a frangible connection and the multiple prescription containers include a flange on the top surface of the set of containers, wherein each of the multiple prescription containers being associated with a prescribed time interval determined by the multiple prescription order, and each multiple prescription container configured to receive the different medications that are consumed at the prescribed time interval;

filling each open multiple prescription container with the different tablets;

inspecting each open multiple prescription container having the different tablets, wherein the open multiple prescription containers are separated by the frangible connection and include the flange on the top of the set of the containers;

labeling a lidstock with a date and a time for having the particular patient consume the different tablets;

sealing the open multiple prescription container with the lidstock after inspecting each open multiple prescription container;

inspecting the set of containers and each associated sealed multiple prescription container having the tablets;

enabling a sleeve to interface with the flange on the top surface of the set of multiple prescription containers, wherein the sleeve includes a sleeve top surface that extends over a plurality of multiple prescription containers; and generating a detailed label that is coupled to the sleeve top surface, wherein the detailed label provides a plurality of medical information regarding the tablets for the patient including, a drug interaction label component that provides information about various drug interactions associated with each medication, and a summary medication label component that describes each medication.

10. The method of claim 9 wherein the processing of the multiple prescription order comprises communicating the multiple prescription order to a first labeling component that labels the lidstock.

11. The method of claim 9 wherein the processing of the multiple prescription order comprises communicating the multiple prescription order to a first inspection module that inspects each open multiple prescription container.

12. The method of claim 9 wherein the processing of the multiple prescription order comprises communicating the multiple prescription order to a second labeling component that generates said detailed label that provides a plurality of medical information.

13. The method of claim 9 wherein the processing of the multiple prescription order comprises communicating the multiple prescription order to a second inspection module that inspects each sealed multiple prescription container.

14. The method of claim 9 wherein the processing of the multiple prescription order comprises analyzing the multiple prescription order.

15. The method of claim 9 further comprising communicating with an insurance company server having the particular patient's insurance information.

16. The method of claim 9 wherein the detailed label comprises the name of the patient.

* * * * *